(12) United States Patent
Scheibel et al.

(10) Patent No.: US 8,883,698 B2
(45) Date of Patent: *Nov. 11, 2014

(54) COMPOSITIONS COMPRISING A NEAR TERMINAL-BRANCHED COMPOUND AND METHODS OF MAKING THE SAME

(75) Inventors: Jeffrey John Scheibel, Glendale, OH (US); David Johnathan Kitko, Cincinnati, OH (US); Jun Xu, Mason, OH (US); Charles Winston Saunders, Fairfield, OH (US); Kenneth Nathan Price, Cincinnati, OH (US); Stephanie Ann Urbin, Liberty Township, OH (US); Phillip Richard Green, Wyoming, OH (US)

(73) Assignee: The Procter & Gamble Co, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/182,990

(22) Filed: Jul. 14, 2011

(65) Prior Publication Data

US 2013/0053300 A1 Feb. 28, 2013

Related U.S. Application Data

(60) Provisional application No. 61/364,519, filed on Jul. 15, 2010.

(51) Int. Cl.
| | | |
|---|---|---|
| *A61K 8/00* | (2006.01) | |
| *A61K 8/34* | (2006.01) | |
| *A61K 8/41* | (2006.01) | |
| *A61K 8/46* | (2006.01) | |
| *A61Q 5/02* | (2006.01) | |
| *A61K 8/37* | (2006.01) | |
| *A61K 8/39* | (2006.01) | |
| *A61Q 5/12* | (2006.01) | |

(52) U.S. Cl.
CPC ............... *A61K 8/342* (2013.01); *A61K 8/416* (2013.01); *A61K 8/463* (2013.01); *A61Q 5/02* (2013.01); *A61K 8/37* (2013.01); *A61K 8/39* (2013.01); *A61Q 5/12* (2013.01); *A61K 2800/34* (2013.01)
USPC .......................... 510/130; 510/136; 424/70.1

(58) Field of Classification Search
None
See application file for complete search history.

(56) References Cited

U.S. PATENT DOCUMENTS

| | | | |
|---|---|---|---|
| 4,985,466 A | | 1/1991 | Deguchi |
| 5,476,649 A | | 12/1995 | Naito et al. |
| 6,335,312 B1 | * | 1/2002 | Coffindaffer et al. ......... 510/159 |
| 6,395,701 B1 | | 5/2002 | Connor et al. |
| 6,531,143 B1 | | 3/2003 | Yakumaru et al. |
| 6,562,328 B2 | | 5/2003 | Pereira et al. |
| 6,986,886 B2 | | 1/2006 | Hammond et al. |
| 7,422,756 B2 | | 9/2008 | Haadem |
| 7,740,873 B2 | | 6/2010 | Decoster et al. |
| 8,147,813 B2 | | 4/2012 | Beauquey et al. |
| 8,338,348 B2 | | 12/2012 | Anim-Danso et al. |
| 8,349,301 B2 | | 1/2013 | Wells et al. |
| 8,349,302 B2 | | 1/2013 | Johnson et al. |
| 8,361,448 B2 | | 1/2013 | Johnson et al. |
| 8,361,449 B2 | | 1/2013 | Wells et al. |
| 2003/0091526 A1 | | 5/2003 | Kaba et al. |
| 2003/0100469 A1 | | 5/2003 | Connor et al. |
| 2003/0202954 A1 | | 10/2003 | Pereira et al. |
| 2003/0236180 A1 | | 12/2003 | Connor et al. |
| 2004/0076654 A1 | | 4/2004 | Vinson et al. |
| 2004/0087461 A1 | | 5/2004 | Connor et al. |
| 2004/0097392 A1 | | 5/2004 | Connor et al. |
| 2007/0298004 A1 | | 12/2007 | Li |
| 2009/0221463 A1 | * | 9/2009 | Kitko et al. ................ 510/120 |
| 2011/0212043 A1 | | 9/2011 | Pham et al. |
| 2011/0260101 A1 | | 10/2011 | Rittig et al. |
| 2012/0012130 A1 | | 1/2012 | Hutton, III et al. |
| 2012/0014900 A1 | | 1/2012 | Carter et al. |
| 2012/0014901 A1 | | 1/2012 | Sunkel et al. |

FOREIGN PATENT DOCUMENTS

| | | |
|---|---|---|
| DE | 19944544 A1 | 3/2001 |
| EP | 1378226 A1 | 1/2004 |
| GB | 2 185 488 A | 7/1987 |
| JP | 2000-344697 | 12/2000 |
| JP | 2001302465 | 10/2001 |
| JP | 2003055699 | 2/2003 |
| JP | 2008297218 | 12/2008 |
| WO | WO 99/18929 A1 | 4/1999 |
| WO | WO0172269 A1 | 10/2001 |
| WO | WO02100373 A1 | 12/2002 |
| WO | WO 2005/009385 A2 | 2/2005 |

OTHER PUBLICATIONS

International Search Report for PCT/US2011/044012 with written opinion, dated Jul. 14, 2011; 12 pages.
International Search report for PCT/US2011/043989 with written opinion, dated Mar. 14, 2013; 10 pages.
International Search Report for PCT/US2011/043990 with written opinion, dated Mar. 8, 2013; 10 pages.
International Search Report for PCT/US2011/043993 with written opinion; dated Mar. 14, 2013; 11 pages.

* cited by examiner

*Primary Examiner* — Necholus Ogden, Jr.
(74) *Attorney, Agent, or Firm* — Brent Matthew Peebles; Kim William Zerby

(57) ABSTRACT

Disclosed herein are novel mixtures of near terminal-branched compounds and derivatives thereof. Further disclosed are methods of making these mixtures, and uses of these mixtures in cleaning compositions (e.g., dishcare, laundry, hard surface cleaners,) and/or personal care compositions (e.g., skin cleansers, shampoo, hair conditioners).

9 Claims, 1 Drawing Sheet

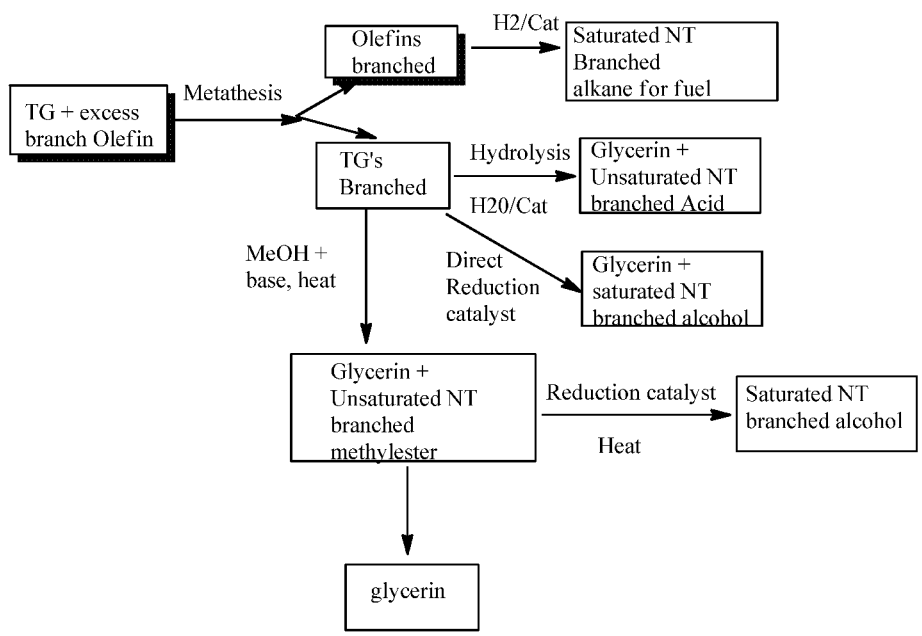

COMPOSITIONS COMPRISING A NEAR TERMINAL-BRANCHED COMPOUND AND METHODS OF MAKING THE SAME

CROSS REFERENCE TO RELATED APPLICATIONS

This application claims the benefit of U.S. Provisional Application No. 61/315,594, filed Mar. 19, 2010; and U.S. Provisional Application No. 61/364,519, filed Jul. 15, 2010.

FIELD OF THE INVENTION

This present invention relates to near terminal-branched compounds, derivatives thereof, and methods of making such compounds. This invention further relates to cleaning and personal care compositions containing such compounds.

BACKGROUND OF THE INVENTION

Surfactants are the single most important cleaning ingredient in household and personal care cleaning products. Environmental regulations, consumer habits, and consumer practices have forced new developments in the surfactant industry to produce lower-cost, higher-performing, and environmentally friendly products. Examples of developments in the surfactant industry are described by Scheibel, *Journal of Surfactants and Detergents*, "The Evolution of Anionic Surfactant Technology to Meet the Requirements of the Laundry Detergent Industry," Volume 7, No. 4, October, 2004 (hereinafter, "Scheibel JSD Article"). Today, challenges facing the surfactant industry include colder wash temperatures, less efficient builders, liquid products without calcium control, and a push for reduced surfactant use overall because of the perceived environmental impact of surfactants.

Alkylbenzene sulfonates (ABS) are surfactants derived from tetrapropylene that have very complex branching structures (e.g., 3 or 4 branches per molecule). The structure below illustrates one example of a hard ABS molecule, which has branching near the polar head group and in the middle of the surfactant.

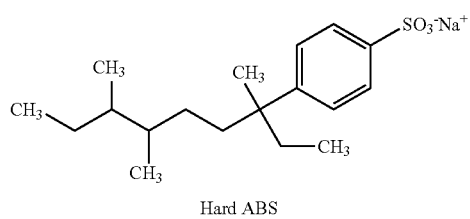

Hard ABS

ABS surfactants were prominent until the early 1960s when they were subjected to environmental regulations for being poorly biodegradable. ABS surfactants were then replaced with the readily biodegradable linear alkylbenzene sulfonate (LAS) surfactants, which are easily obtainable and currently in use today. Use of LAS surfactants and other similar linear surfactants is limited because they have poor solubility in cold- and hard-water conditions. In fact, more than half of the LAS detergent in products may be lost during use due to the formation of multilayered vesicles that resemble large onion-like structures. Formulators can increase the solubility of linear surfactants by, for example, introducing co-surfactants or by using linear alcohol ethoxylated sulfates (AES). ABS, LAS, and AES surfactants are described in detail in the Scheibel JSD Article.

Surfactants with light, mid-chain branching, such as highly soluble alcohol sulfate (HSAS) surfactants derived from petroleum feedstocks, were then developed for use in consumer products. HSAS surfactants are illustrated in the Scheibel JSD Article, as well as U.S. Pat. Nos. 6,020,303; 6,060,443; and 6,335,312; and U.S. Patent Application Publication No. 2010/0137649.

Although certain known surfactants provide good cleaning ability in cold, hard water, have high solubility, good grease removal properties, and good biodegradability, further modifications to the chemical structure of the surfactants may be desirable to improve various properties. For example, in some cases, foamability and stability of foam are critical to consumer goods applications, such as in dishwashing liquids, hand wash detergents, and shampoos. The present invention is directed to novel surfactants having a low interfacial tension that deliver good cleaning with grease removal properties in cold, hard water.

SUMMARY OF THE INVENTION

In one aspect, the invention relates to a composition that includes at least about 50 wt %, preferably at least about 75 wt %, more preferably at least about 90 wt %, even more preferably at least about 95 wt %, by weight, of a mixture of at least two compounds of Formula I:

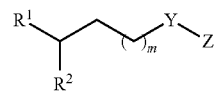

In this mixture, $R^1$ is hydrogen, methyl, or ethyl;
$R^2$ is $(C_1\text{-}C_n)$alkyl or $(C_1\text{-}C_n)$alkenyl having 0, 1, 2, or 3 $(C_1\text{-}C_3)$alkyl branches;
m is 5-37 and n is 1-33, wherein m+n is 6-38; preferably m is 7-27 and n is 1-23, wherein m+n is 8-28;
Y is null or $W_p$;
W is selected from the group consisting of ethylenoxy, propylenoxy, butylenoxy, and mixtures thereof;
p is 1 to 30; and
Z is a hydrophilic moiety such as, for example, hydroxy, carboxylate, sulfate, disulfate, sulfonate, disulfonate, glycerol ester sulfonate, amine, monoalkylamine, dialkylamine, amine oxide, a polyhydroxy moiety, a phosphate ester, glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether, a glycerol ether sulfate, a polyglycerol ether, a polyglycerol ether sulfate, sorbitan ester, an alkylpolyglycoside (APG), alkylpolyxyloside, urea, ammonioalkanesulfonate, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, a sulfonated alkyl ester, and a sulfonated fatty acid. Preferably, Z is selected from the group consisting of hydroxy, glycerol ether, polyglycerol ether, polyglycoside, polyxyloside, carboxylate, sulfate, sulfonate, glycerol ether sulfonate, amine, monoalkylamine, dialkylamine, amine oxide, monoalkanolamide, amidopropyl betaine, and an alkylated quat. In one embodiment herein, the foregoing selections for Z do not include carboxylate.

In this composition, with respect to at least one of the compounds, when $R^1$ is H, $R^2$ has 1, 2, or 3 ($C_1$-$C_3$) alkyl branches, and when $R^1$ is methyl or ethyl, $R^2$ has 0, 1, or 2 ($C_1$-$C_3$)alkyl branches. In one embodiment, with respect to the at least two compounds in the mixture, when $R^1$ is H, $R^2$ has 1, 2, or 3 ($C_1$-$C_3$) alkyl branches, and when $R^1$ is methyl or ethyl, $R^2$ has 0, 1, or 2 ($C_1$-$C_3$)alkyl branches. Alternatively or additionally, in yet another embodiment, the branching occurs on carbon atoms that are within 40% of the nonfunctionalized terminus of the longest carbon chain. Alternatively or additionally, in yet another embodiment, the composition is substantially free of secondary hydroxy compounds.

In another aspect, the invention relates to a composition that includes at least about 50 wt %, preferably at least about 75 wt %, more preferably at least about 90 wt %, even more preferably at least about 95 wt %, by weight, of a mixture of at least two compounds selected from the group consisting of:

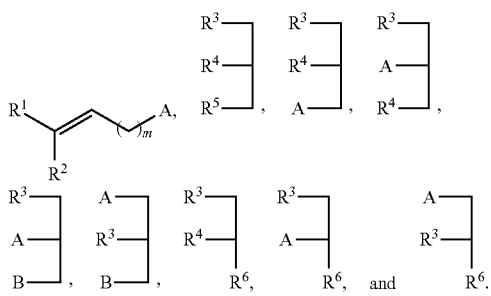

In this mixture, A and B are each independently OH or O(C=O)$R^7$;
$R^1$ is hydrogen, methyl, or ethyl;
$R^2$ is ($C_1$-$C_n$) alkyl or ($C_1$-$C_n$)alkenyl having 0, 1, 2, or 3 ($C_1$-$C_3$)alkyl branches;
$R^3$, $R^4$, and $R^5$ are each independently

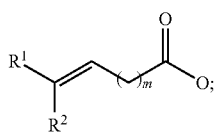

$R^6$ is hydrogen, methyl, or ethyl;
$R^7$ is ($C_1$-$C_{26}$) alkyl; and,
m is 5-37 and n is 1-33, wherein m+n is 6-38; preferably m is 7-27 and n is 1-23, wherein m+n is 8-28.

In one embodiment, when $R^1$ is H, $R^2$ has 1, 2, or 3 ($C_1$-$C_3$) alkyl branches, and when $R^1$ is methyl or ethyl, $R^2$ has 0, 1, or 2 ($C_1$-$C_3$)alkyl branches. Alternatively or additionally, in yet another embodiment, the branching occurs on carbon atoms that are within 40% of the nonfunctionalized terminus of the longest carbon chain. Alternatively or additionally, in yet another embodiment, the composition is substantially free of secondary hydroxy compounds.

In another aspect, the invention relates to a composition that includes the partially saturated versions of the above compounds or fully saturated versions of the above compounds, wherein an above compound is hydrogenated to provide the partially saturated or fully saturated version thereof.

In another aspect, the invention relates to a composition that includes at least about 50 wt %, preferably at least about 75 wt %, more preferably at least about 90 wt %, even more preferably at least about 95 wt %, by weight, of a mixture of at least two compounds of Formula IV:

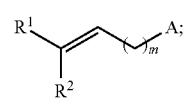

In this mixture, A in each of the at least two compounds is independently COOH, COO$^-$M, O(C=O)$R^7$ or (C=O)O$R^7$;
$R^1$ is hydrogen, methyl, or ethyl;
$R^2$ is ($C_1$-$C_n$)alkyl or ($C_1$-$C_n$)alkenyl having 0, 1, 2, or 3 ($C_1$-$C_3$)alkyl branches, wherein when $R^1$ is H, $R^2$ has 1, 2, or 3 ($C_1$-$C_3$)alkyl branches, and when $R^1$ is methyl or ethyl, $R^2$ has 0, 1, or 2 ($C_1$-$C_3$)alkyl branches, and wherein branching occurs on carbon atoms that are within 40% of the nonfunctionalized terminus of the longest carbon chain;
$R^7$ is ($C_1$-$C_{26}$)alkyl;
M is Li$^+$, Na$^+$, K$^+$, Ca$^{2+}$, Mg$^{2+}$, and

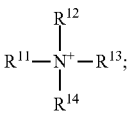

$R^{11}$, $R^{12}$, $R^{13}$, and $R^{14}$ are each independently hydrogen, ($C_1$-$C_{22}$)alkyl, ($C_1$-$C_6$)alkanol, and ($C_1$-$C_{22}$)alkenyl;
m is 5-37 and n is 1-33, wherein m+n is 6-38; preferably m is 7-27 and n is 1-23, wherein m+n is 8-28.

In one embodiment, when $R^1$ is H, $R^2$ has 1, 2, or 3 ($C_1$-$C_3$)alkyl branches, and when $R^1$ is methyl or ethyl, $R^2$ has 0, 1, or 2 ($C_1$-$C_3$)alkyl branches. Alternatively or additionally, in one embodiment, the branching occurs on carbon atoms that are within 40% of the nonfunctionalized terminus of the longest carbon chain. Alternatively or additionally, in yet another embodiment, the composition is substantially free of secondary hydroxy compounds.

In another aspect, the invention relates to a composition that includes the partially saturated version of the above compounds, wherein an above compound is hydrogenated to provide the partially saturated version thereof. In yet another aspect, the invention relates to a cleaning composition that includes (a) about 0.001 wt % to 100 wt % of a mixture of at least two compounds of Formula I, wherein Formula I is defined above, and (b) about 0 wt % to about 99.999 wt %, preferably about 1 wt % to about 80 wt % of an additional cleaning component.

In yet another aspect, the invention relates to a personal care composition that includes (a) about 0.001 wt % to about 100 wt % of a mixture of at least two compounds of Formula I, wherein Formula I is defined above, and (b) about 0 wt % to about 99.999 wt %, preferably about 1 wt % to about 80 wt % of an additional personal care component.

DETAILED DESCRIPTION OF THE INVENTION

It has now unexpectedly been found that compositions containing mixtures of least two fatty acids, fatty alcohols, derivatives of fatty acids or alcohols, and mixtures thereof, having near terminal-branches, provide superior properties and performance when used as surfactants in cleaning compositions such as, for example, granular, bar-form, and liquid laundry detergents; liquid hand dishwashing compositions; liquid, gel, and bar-form personal cleansing products; shampoos; dentifrices; hard surface cleaners, and the like. Also included are a sachet, a two in one pouch containing both solid and liquid compartments, a tablet, a disinfectant for hospitals, an industrial cleaner, a decontaminant for biological or chemical warfare agents and the like.

International Patent Application Publication No. WO/1999/020722 (the '722 publication) describes the use of branched fatty acids, salts of branched fatty acids, and lower esters as useful in formulations, such as for laundry products, personal care products, pharmaceutical compositions, industrial cleaners, and the like. However, the '722 publication does not teach the utility of near terminal-branched fatty acids, salts of near terminal-branched fatty acids or lower esters excluding other types of branches (e.g., mid-chain branched compounds). The '722 publication also does not teach the utility of near terminal-branched alcohols and their derivatives, excluding other types of branches (e.g., mid-chain branched compounds).

As used herein, "near terminal-branched" fatty acids, fatty alcohols, and derivatives of fatty acids and alcohols (i.e., "near terminal-branched compounds") contain one, two, or three ($C_1$-$C_3$)alkyl branches on a carbon atom within 40% of the nonfunctionalized end of the longest chain. The functionalized end of the near terminal branched fatty acids, fatty alcohols, and derivatives of fatty acids and alcohols is that which contains the acid, alcohol, or derivative moieties. The nonfunctionalized carbon at the end of the longest chain is referred to as the 'omega' position. For example, near terminal-branched surfactants that are 10 carbon atoms in length can have branching up to the omega-3 position, while near terminal-branched surfactants that are 30 carbon atoms in length can have branching up to the omega-11 position. The near terminal-branched compounds of the invention typically have branching at the omega-1, omega-2, omega-3, omega-4, omega-5, and/or omega-6 positions of the compound (illustrated in the structure below), depending on the length of the compound, preferably at the omega-1, omega-2, and/or omega-3 positions, more preferably at the omega-1 and/or omega-2 positions.

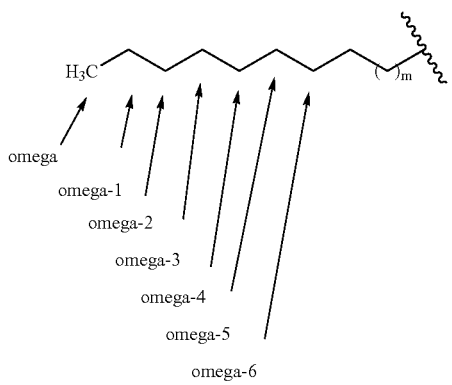

Near terminal-branched compounds with branching at the omega-1 position are referred to as "iso," as illustrated in the below structure.

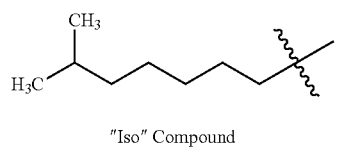 [SMILES: *CCCCCC(C)C]

"Iso" Compound

Near terminal-branched compounds with branching at the omega-2 position are referred to as "anteiso," as illustrated in the below structure.

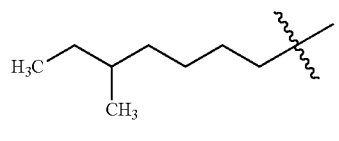

"Anteiso" Compound

For example, the below compound has 10 carbon atoms in its longest carbon chain with a methyl branch on the second carbon from the nonfunctionalized end of the chain (the omega-1 position). Thus, the branch is within 40% of the nonfunctionalized end of the carbon chain (e.g., 2/10× 100%=20%) and the below compound is referred to as near terminal-branched.

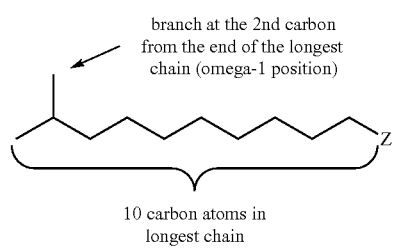

The below compound is also referred to as "near terminal-branched" because the methyl substituent is at the fourth carbon from the nonfunctionalized end of the chain (the omega-3 position) and within 40% of the nonfunctionalized end of the carbon chain (e.g., 4/10×100%=40%).

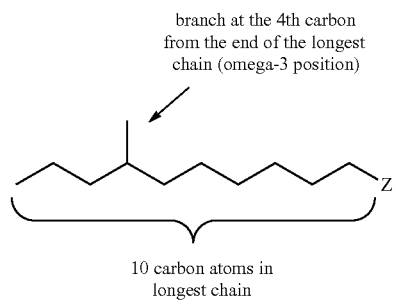

In contrast, the methyl branch is on the fifth carbon from the nonfunctionalized end of the chain (the omega-4 position) in the below structure. Thus the branch is not within 40% of the nonfunctionalized end of the carbon chain (e.g., 5/10× 100%=50%) and the below compound is not referred to as "near terminal-branched."

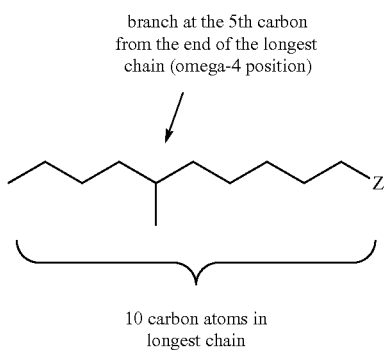

branch at the 5th carbon from the end of the longest chain (omega-4 position)

10 carbon atoms in longest chain

As used herein, the term "alkyl" refers to straight chained and branched saturated hydrocarbon groups, nonlimiting examples of which include methyl, ethyl, and straight and branched propyl, butyl, pentyl, hexyl, heptyl, and octyl groups containing the indicated number of carbon atoms. The term $C_n$ means the alkyl group has "n" carbon atoms. For example, $(C_1-C_7)$alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms).

As used herein, the term "alkenyl" is defined identically as "alkyl" except for containing a carbon-carbon double bond, e.g., ethenyl, propenyl, and butenyl.

As used herein, "linear" fatty acids, fatty alcohols, and derivatives of fatty acids and alcohols (i.e., "linear compounds") are free of branches on the carbon chain.

As used herein, "mid-chain" branched fatty acids, fatty alcohols, and derivatives of fatty acids and alcohols (i.e., "mid-chain branched compounds") contain alkyl branches on a carbon atom that is between about 40% to about 60% of the nonfunctionalized end of the longest carbon chain. For example, a mid-chain branched compound that is 12 carbon atoms in length can have branching on the omega-5 and/or omega-6 position. A mid-chain branched compound that is 30 carbon atoms in length can have branching on the omega-12 to the omega-17 position.

The compositions containing mixtures of surfactants with near terminal-branching provide at a minimum comparable cleaning ability in cold, hard water, solubility, and grease removal properties as compositions comprising surfactants having mid-chain branching. Advantageously, however, the absence of mid-chain branching of the surfactants in the mixtures of the invention allows them to have some of the advantageous properties of linear surfactants in some respects. For example, they achieve a maximum air/water interfacial packing. Thus, they have improved compaction, high sudsing ability in the absence of hard water, and should exhibit better biodegradability than surfactants with mid-chain branching. Further the mixtures of near terminal-branched compounds of the cationic type can form unique ionic crystal liquid concentrates when combined with certain anionic surfactants. These concentrates can be stored and shipped at low cost, and added to a personal care or cleaning composition at will.

It has also been found that compositions that contain mixtures of at least two fatty acids, fatty alcohols, derivatives of fatty acids or alcohols, and mixtures thereof, wherein at least one compound of the mixture comprises a near terminal-branch, provide superior performance when used in conditioning applications, such as, for example, hair conditioners. These compositions are stable at low temperatures, dilute quickly and easily, and tolerate hard water conditions, avoiding the precipitation of calcium salts and anionic surfactants, which results in improved performance and desirable hair feel. In fact, the biodegradable mixture of the invention can act as a sustainable alternative to silicones in some applications.

In the past, use of near terminal-branched compounds in cleaning and conditioning applications was not pursued because these compounds were only found as very low concentration materials in biological systems and thus too expensive to produce in commercial quantities via isolation and purification techniques. Some organisms do produce substantial quantities of specific materials such as iso and anteiso fatty acids of certain chain lengths such as in lanolin coming from sheep wool. Even today purification and processing of this available source of iso and anteiso fatty acids may be cost prohibitive and would not provide good value for the consumer for daily use. Furthermore, even with current state of the art industrial purification methods impurities from the lanolin prohibit use in some applications even if cost were not an issue. It was also thought that these branched types would destroy gel networks required for appropriate physical properties in some formulations. Unexpectedly, it is found that using mixtures of near terminal-branched compounds actually allows the phase of the gel networks to be controlled and provides more formulation flexibility for the manufacturer of the consumer goods products containing the near terminal-branched compounds.

Mixtures Comprising a Terminal-Branched Compound

In one aspect, the invention relates to compositions containing mixtures of compounds wherein at least one of the compounds, and in another embodiment, two of the compounds, is near terminal-branched compound. The mixtures are useful in cleaning and personal care applications.

Most mixtures of fatty acids and alcohols that exist in nature are linear saturated and unsaturated compounds. For example, jojoba oil is the triglyceride version of a mixture of eicosenoic acid (66-71 wt %), docosenoic acid (14-20 wt %) and oleic acid (10-13 wt %). Examples of various plant and animal sources of fats and oils that are isolated in bulk today are Jatropha, rapeseed, canola, soybean, palm, algae, tallow, fish, sweet sorghum, corn as references to oils and fats. All of these contain at best trace levels of the desired material, if at all. Some of the branched fatty acids that exist in nature, but are not easy to obtain or isolate, have 10 to 30 or more, most often 14 to 18 carbon atoms, are saturated or unsaturated, and have one or more methyl branches (e.g., 18-methyl-eicosanoic acid, 13-methyltetradecanoic acid, 14-methyl-hexadecanoic acid, 13,13-dimethyltetradecanoic acid). These types of compounds are found in, for example, marine animals, microbial lipids, animals, plants, and bacteria. (see e.g., Christie, "Fatty Acids: Branched-Chain," The Lipid Library, updated Jun. 28, 2010 from www.lipidlibrary.aocs.org).

Although some fatty acid/alcohol mixtures exist in nature that contain anteiso and iso compounds, the concentrations of anteiso and iso compounds in these mixtures is low. For example, in most mammalian tissues, branched-chain fatty acids rarely make up more than 1-2 wt % of the total amount of fatty acids. In fish oils, iso and anteiso branched-chain fatty acids are also typically present at only 1-2 wt %, and only iso and anteiso compounds with a chain length of 14-18 carbon atoms. Isolation of these materials is considered cost prohibitive.

In addition, isolation of the anteiso and iso compounds from linear and other branched components in these mixtures is traditionally difficult to accomplish in useful quantities. For example, lanolin contains about 49.1 wt % of anteiso and iso compounds, about 12.87 wt % of linear fatty acids, and about 35.29 wt % of hydroxy and iso-hydroxy fatty acids, based on the total weight of lanolin (see e.g., Schlossman et al., "Lanolin and Its Derivatives," Journal of the American Oil-Chemists' Society, 55, 447-450, 1978). To obtain enhanced cleaning performance, the anteiso and iso compounds should be isolated from the hydroxy and iso-hydroxy fatty acids because these hydroxy fatty acids adversely affect cleaning performance. Another issue with lanolin or derivatives of lanolin is contact dermatitis as discussed in: *Contact Dermatitis*, 1979, 5, 65-72.

For superior cleaning performance, the distribution of chain lengths in compositions containing a near terminal-branched surfactant should maximally span a difference in the number of carbon atoms in the longest vs. shortest carbon chain of no more than 5 carbon atoms, preferably 4 carbon atoms, more preferably 3 carbon atoms, for example, 2 carbon atoms. For example, mixtures containing near terminal-branched compounds with 12, 13, and 14 carbon atoms, or 12 and 13 carbon atoms, or 12 and 15, or 13 and 16, in the longest carbon chain provide desirable sudsing performance. Furthermore, compositions containing a terminal-branched compound within a range of 10 to 13 carbon atoms in the longest carbon chain are desirable for dishcare compositions. Mixtures containing near terminal-branched compounds within a range of 12 to 15 carbon atoms in the longest carbon chain are desirable for laundry compositions. Mixtures containing near terminal-branched compounds within a range of 8 to 12 carbon atoms in the longest carbon chain are desirable for hard surface cleaning compositions. If surfactants with longer carbon chains are used for a hard surface cleaning composition, for example, the surfactants tend to crystallize on surfaces to form a residue, which is a negative performance signal to customers.

Further still, the mixtures that exist in nature cannot be manufactured to contain shorter chain compounds, to contain mixtures of two or more branches near terminal, to exclude iso compounds, or to exclude linear compounds due to the biochemical processes involved. Obtaining mixtures that do not contain iso compounds and linear compounds, such as some embodiments of mixtures of the invention, is highly desirable because these mixtures provide superior cleaning in laundry products, sudsing performance in dishwashing products, while minimizing of crystallinity, improving compaction of formulations which minimizes the environmental impact (use and ship less water and use less packaging materials), and lowers cost to the consumer. However, if it is desired by the formulator to use single chain components of anteiso then some iso of the same chain length can be desirable to disrupt the crystallinity of the single component material.

The mixtures of near terminal-branched fatty acids, fatty alcohols, and derivatives of fatty acids and alcohols of the invention can overcome the aforementioned disadvantages. A composition of the invention typically contains mixtures of near terminal-branched compounds in useful concentrations. For example, the compositions of the invention contain at least about 50 wt %, preferably at least about 75 wt %, more preferably at least about 90 wt %, for example, about 95 wt %, up to and including about 100 wt % of the mixtures of near terminal-branched fatty acids, fatty alcohols, and derivatives of fatty acids and alcohols, based on the total weight of the composition. Further, the compositions of the invention are free of a substantial amount of hydroxy fatty acids/alcohols and iso-hydroxy fatty acids/alcohols (i.e. "secondary hydroxy compounds"). For example, the compositions of the invention contain no more than about 2 wt % of secondary hydroxy compounds, preferably no more than about 1 wt % of secondary hydroxy compounds, even more preferably 0 wt % of secondary hydroxy compounds, based on the total weight of the composition.

Further, the types of near terminal-branched compounds can be chosen based on the desired properties of the composition. For example, iso compounds behave more like linear compounds than anteiso and omega-3 compounds; and anteiso and omega-3 compounds are less crystalline than iso compounds. The mixtures of the invention can include from 0 wt % to 100 wt % of iso compounds based on the total weight of near terminal-branched compounds. In some embodiments, the mixtures of the invention include about 10 wt %, about 20 wt %, about 30 wt %, about 40 wt %, about 50 wt %, about 60 wt %, about 70 wt %, about 80 wt % and about 90 wt % of iso compounds, based on the total weight of near terminal-branched compounds. In some preferred embodiments, the mixture of the invention includes less than 50 wt % of the iso compound. For example, the mixture can include about 1 wt % to about 40 wt %, or about 10 wt % to about 30 wt % of iso compounds, based on the total weight of near terminal-branched compounds. In other embodiments, the mixtures of the invention include about 20 wt % or about 40 wt % of the iso compound, based on the total weight of near terminal-branched compounds.

The compositions of the invention can also be tuned to include mixtures of near terminal-branched compounds that have specific carbon chain lengths to meet the maximum chain-length range requirements previously discussed, or to inexpensively provide unique, previously unobtainable mixtures. For example, the mixtures of the invention can contain near terminal-branched compounds with 12 and 15 total carbon atoms; 12, 13, and 14 total carbon atoms; or 11, 13, and 17 total carbon atoms, e.g., mixtures that could not previously be obtained without excessive cost. Further still, the mixtures of the invention can include specific near terminal-branched fatty acids, fatty alcohols, and derivatives of fatty acids and alcohols that provide the mixture with multiple functions. For example, the mixtures of the invention can include near terminal-branched compounds with 12 and 18 total carbon atoms, making it useful for both surfactant performance and fabric softening.

The compositions of the invention can optionally include a specific amount of one more linear compounds or mid-chain branched compounds, each having a specific chain length (e.g., linear compounds or mid-chain branched compounds with 12, 13, 14, 15, and/or 16 total carbon atoms). The linear content can be adjusted according to the process conditions and/or starting materials used to provide desired compounds, or post added to provide a blend. The amount and identity of a linear compound and/or a mid-chain branched compound in the composition depends on the particular application. For example, the amount of linear surfactant in compositions used for sudsing applications can be up to 50 wt %, based on the total weight of the mixture, while the amount of linear surfactant used for laundry applications can be up to about 10 wt %, based on the total weight of the composition. In some embodiments, the linear surfactant is less than about 2 wt % based on the total weight of the composition.

In one embodiment, the composition of the invention contains a mixture of at least two compounds of Formula I:

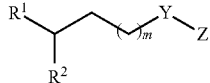

wherein $R^1$ is hydrogen, methyl, or ethyl;

$R^2$ is $(C_1-C_n)$alkyl or $(C_1-C_n)$alkenyl having 0, 1, 2, or 3 $(C_1-C_3)$alkyl branches, m is 5-37 and n is 1-33, wherein m+n is 6-38; preferably m is 7-27 and n is 1-23, wherein m+n is 8-28; for example, when m is 7, n is 9, and when m is 11, n is 17;

Y is null or $W_p$;

W is selected from the group consisting of ethylenoxy, propylenoxy, butylenoxy, and mixtures thereof;

p is 1 to 30;

Z is a hydrophilic moiety selected from the group consisting of hydroxy, carboxylate, sulfate, disulfate, sulfonate, disulfonate, glycerol ester sulfonate, amine, monoalkylamine, dialkylamine, amine oxide, a polyhydroxy moiety, a phosphate ester (i.e., monophosphate ester, diphosphate ester, triphosphate esters, and mixtures thereof), glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether, a glycerol ether sulfate, a polyglycerol ether, a polyglycerol ether sulfate, alkylpolyglycoside, alkylpolyxyloside, urea, sorbitan ester, ammonioalkanesulfonate, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, a sulfonated alkyl ester, and a sulfonated fatty acid.

wherein with respect to at least one of the compounds, when $R^1$ is H, then $R^2$ has 1, 2, or 3 $(C_1-C_3)$ alkyl branches, and when $R^1$ is methyl or ethyl, then $R^2$ has 0, 1, or 2 $(C_1-C_3)$alkyl branches. In one embodiment, with respect to the at least two compounds, when $R^1$ is H, then $R^2$ has 1, 2, or 3 $(C_1-C_3)$ alkyl branches, and when $R^1$ is methyl or ethyl, then $R^2$ has 0, 1, or 2 $(C_1-C_3)$alkyl branches.

In one embodiment herein, Z is selected from the group consisting of hydroxy, glycerol ether, polyglycerol ether, polyglycoside, carboxylate, sulfate, sulfonate, amine oxide, glycerol ether sulfonate, amine, monoalkylamine, dialkylamine, monoalkanolamide, amidopropyl betaine, and an alkylated quat.

In one embodiment herein, the foregoing selections for Z do not include carboxylate.

In some embodiments, the at least two compounds of Formula I require a counterion. In embodiments when the counterion is an anion, the anion can include bromide, chloride, and methylsulfates. In embodiments when the counterion is a cation, the cation can include, for example, $Li^+$, $Na^+$, $K^+$, $Ca^{2+}$, $Mg^{2+}$, and

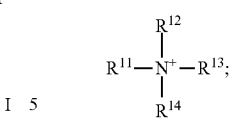

wherein $R^{11}$, $R^{12}$, $R^{13}$, and $R^{14}$ are each independently hydrogen, $(C_1-C_{22})$ alkyl, $(C_1-C_6)$ alkanol, $(C_1-C_{22})$ alkenyl, and mixtures thereof. In some embodiments, the cation is selected from the group consisting of $NH_4^+$, $Na^+$, $K^+$, mono-, di-, or tri-alkyl ammonium, mono-, di, or tri-alkanol ammonium, and mixtures thereof. The monoalkanol ammonium compounds of the present invention can include compounds where $R^{11}$ is $(C_1-C_6)$ alkanol and $R^{12}$, $R^{13}$, and $R^{14}$ are hydrogen; dialkanol ammonium compounds of the present invention can include, for example, compounds where $R^{11}$ and $R^{12}$ each independently $(C_{1-6})$alkanol, and $R^{13}$ and $R^{14}$ are hydrogen; trialkanol ammonium compounds of the present invention can include, for example, compounds where each $R^{11}$, $R^{12}$ and $R^{13}$ are independently $(C_{1-6})$alkanol and $R^{14}$ is hydrogen. Preferred alkanol ammonium salts of the present invention are the mono-, di- and tri-quaternary ammonium compounds having the formulas: $H_3N^+(C_2H_4OH)$, $H_2N^+(C_2H_4OH)_2$, and $HN^+(C_2H_4OH)_3$. The cation is preferably $Na^+$, $K^+$, and the C2 alkanol ammonium salts listed above, most preferably sodium.

It is further understood that the term "sulfate", unless otherwise specified, includes any positively charged counterion or positively charged multivalent counterion form of the sulfate including hydrogen. As such, salts are also included, and may include for example, sodium, magnesium and calcium salts, with sodium salts being preferred. Furthermore, if a multivalent counterion is used the anion group must be multiplied to form the compound. Thus, as a nonlimiting example, 14-methylhexadecyl sulfate can be calcium bis(14-methylhexadecyl sulfate).

In accordance with the present invention, a compound of Formula I can be converted to a compound having more than one hydrophobic moiety, as shown below, by processes well known in the art:

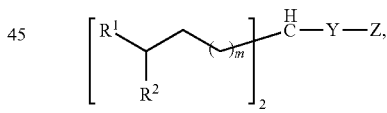

wherein all variables are as previously described.

The at least two compounds of Formula I have different chemical structures and are present in the composition in at least about 50 wt %, preferably at least about 75 wt %, more preferably at least about 90 wt %, for example, about 95 wt %, up to and including 100 wt %, based on the total weight of the composition.

The at least two compounds of Formula I can independently have about 8 total carbon atoms to about 40 total carbon atoms, preferably of about 10 total carbon atoms to about 30 total carbon atoms. Preferably, the at least two compounds include some degree of mixed chain lengths to minimize crystallinity, as previously described herein. The exact length of the at least two compounds depends on their desired use. Compounds useful in sudsing applications generally have about 10 to about 16 total carbon atoms, preferably about 12 to about 14 total carbon atoms. Compounds useful in dishcare applications generally have about 10 to about 13 total carbon atoms. Compounds useful in laundry applications generally have about 8 to about 18 total carbon atoms. Compounds useful in hard surface cleaning applications generally have about 8 to about 12 total carbon atoms. Compounds useful in fabric softening applications generally have about 17 to about 40 total carbon atoms. Compounds useful in shampoo applications generally have about 12 to about 22 total carbon atoms. Compounds useful in conditioning applications generally have about 16 to about 36 total carbon atoms.

The branching on the at least two compounds of Formula I occurs within 40% of the nonfunctionalized terminus of the longest carbon chain. For example, the branching occurs up to the omega-6 position, preferably up to the omega-5 position, more preferably up to the omega-4 position, even more preferably up to the omega-3 position, provided that the position of the branch is within 40% of the nonfunctionalized terminus of the longest carbon chain. For example, omega-2 branching can occur only on compounds that have at least 8 carbon atoms in their longest chain. Omega-3 branching can occur only on compounds that have at least 10 carbon atoms in their longest chain. Omega-4 branching can occur only on compounds that have at least 13 carbon atoms in their longest chain. Omega-5 branching can occur only compounds that have at least 15 carbon atoms in their longest chain. Omega-6 branching can occur only on compounds that have at least 18 carbon atoms in their longest chain. In some preferred embodiments, branching occurs at the omega-1 position, the omega-2 position, or on both the omega-1 and omega-2 positions. Thus, in some embodiments, when $R^2$ has 5 or less carbon atoms in its longest chain, $R^1$ can be hydrogen, methyl, or ethyl. In other embodiments, when $R^2$ has 6 or more carbon atoms in its longest chain, $R^1$ is hydrogen.

The near terminal-branching on the at least two compounds of Formula I is composed of $(C_1-C_3)$alkyl moieties. For example, the branches can include methyl moieties, ethyl moieties, propyl moieties, isopropyl moieties, and mixtures thereof. Preferably, the branches include methyl moieties, ethyl moieties, and mixtures thereof. More preferably, the branches include methyl moieties.

The at least two near terminal-branched compounds of Formula I include one branch, two branches, or three branches. In some preferred embodiments, the at least two near terminal-branched compounds of Formula I each contain one branch. In some embodiments, the at least two compounds of Formula I have two or three branches and two of these branches are at the omega-1 position. In other embodiments, the at least two compounds have two or three branches and none of these branches are geminal. In embodiments when $R^2$ has three branches, $R^1$ is hydrogen.

The mixtures in this embodiment of the invention can include from 0 wt % to about 100 wt % of iso compounds based on the total weight of near terminal-branched compounds. In some embodiments, the mixtures of the invention include about 10 wt %, about 20 wt %, about 30 wt %, about 40 wt %, about 50 wt %, about 60 wt %, about 70 wt %, about 80 wt % and about 90 wt % of iso compounds, based on the total weight of near terminal-branched compounds. In some preferred embodiments, the mixture of the invention includes less than 50 wt % of the iso compound. For example, the mixture can include about 1 wt % to about 40 wt %, or about 10 wt % to about 30 wt % of iso compounds, based on the total weight of near terminal-branched compounds. In other embodiments, the mixtures of the invention include about 20 wt % or about 40 wt % of the iso compound, based on the total weight of near terminal-branched compounds. In some embodiments, the mixtures of the invention include only iso compounds, anteiso compounds, or mixtures thereof.

In some embodiments, the mixture of the invention is free of iso compounds, linear compounds, and/or short chain compounds.

In some embodiments, the compositions containing the mixtures of the at least two compounds of Formula I are substantially free of secondary hydroxy compounds (i.e., hydroxy fatty acids/alcohols and iso-hydroxy fatty acids/alcohols). For example, the compositions of the invention may contain no more than about 2 wt % of secondary hydroxy compounds, preferably no more than about 1 wt % of secondary hydroxy compounds, even more preferably 0 wt % of secondary hydroxy compounds, based on the total weight of the composition.

The compositions containing the mixtures of the at least two compounds of Formula I optionally include a linear compound, a mid-chain branched compound, or mixtures thereof in an amount of no more than about 50 wt %, preferably no more than 10 wt %, for example, no more than about 2 wt %, based on the total weight of the composition, as previously described herein. The linear compound and the mid-chain branched compound can include any end group previously defined by the variables "Y-Z" above. The specific amount of linear compound and/or mid-chain branched compounds depends on the desired application, as previously described.

In one embodiment, at least one of the compounds, or alternatively the at least two compounds, may be selected from 7-methyldecyl sulfate, 8-methyldecyl sulfate, 9-methylundecyl sulfate, 10-methyldodecyl sulfate, 11-methyltridecyl sulfate, 12-methyltetradecyl sulfate, 10-methyltetradecyl sulfate, 10-ethyltetradecyl sulfate, 15-methylheptadecyl sulfate, 16-methyloctadecyl sulfate, 13-methylheptadecyl sulfate, 17-nonadecyl sulfate, 18-methylicosyl sulfate, 18-propylicosanol, 19-methylhenicosyl sulfate, 20-methyldocosyl sulfate, 21-methyltricosyl sulfate, 22-methyltetracosyl sulfate, 11-methyltetradecylsulfate, 12-methyltridecylsulfate, 10-methyltetradecanol sulfate, 12-methyltetradecanol, 12-methyltetradecanol, 12-methyltridecanol, 15-methylhexadecanol, 14-methylhexadecanol, 15-methylheptadecanol, 14-methylhexadecylpalmitate, 13-methylhexadecylpalmitate, 15-methylhexadecylstearate, 16-methylhexadecylstearate, 11-methyldodecylsulfate, 10-methyldodecylsulfate-1-ethoxylated, and 11-methyldodecylsulfate-1-ethoxylated.

In another embodiment, at least one of the compounds, or alternatively the at least two compounds, may be selected from 12-methyltetradecylsulfate, 11-methyltetradecylsulfate, 12-methyltridecylsulfate, 12-methyltetradecanol, 11-methyltetradecanol, 12-methyltridecanol, 15-methylhexadecanol, 14-methylhexadecanol, 15-methylheptadecanol, 14-methylhexadecylpalmitate, 13-methylhexadecylpalmitate, 15-methylhexadecylstearate, 16-methylhexadecylstearate, 10-methyldodecylsulfate, 11-methyldodecylsulfate, 10-methyldodecylsulfate-1-ethoxylated, and 11-methyldodecylsulfate-1-ethoxylated.

Nonlimiting examples of the compounds that may be present in the mixtures are shown in Table A (compounds with 1 methyl branch), Table B (compounds with 2 methyl branches), and Table C (compounds with 3 methyl branches). Any of the methyl branches in Tables A, B, and C can be substituted with ethyl, propyl, or isopropyl branches. Further, an alkyleneoxy group, as previously described, can be present before substituent "Z."

TABLE A

Compounds with 1 Methyl Branch

| Compound # | # Carbon Atoms | Structure |
|---|---|---|
| 1 | 8 | 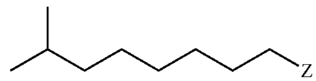 |
| 2 | | 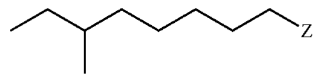 |
| 3 | 9 | 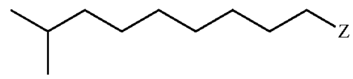 |
| 4 | | 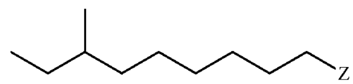 |
| 5 | 10 | 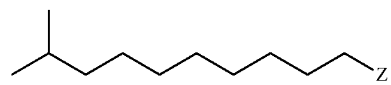 |
| 6 | | 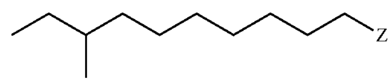 |
| 7 | | 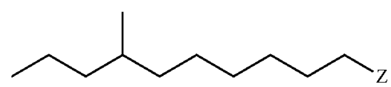 |
| 8 | 11 | 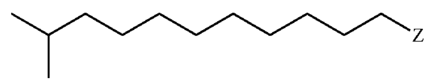 |
| 9 | | 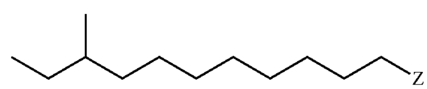 |
| 10 | | 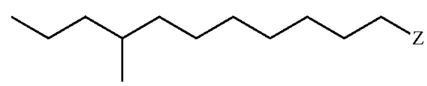 |
| 11 | 12 | 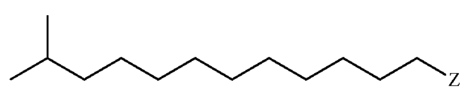 |
| 12 | | 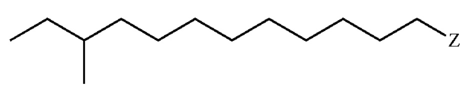 |
| 13 | | 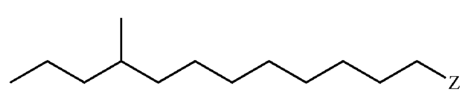 |
| 14 | 13 | 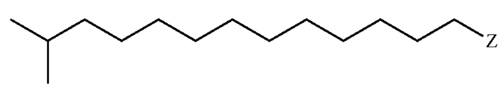 |
| 15 | | 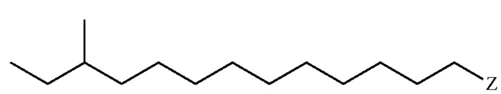 |
| 16 | | 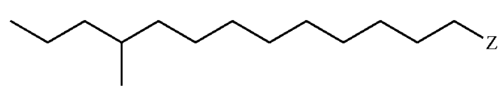 |

TABLE A-continued

Compounds with 1 Methyl Branch

| Compound # | # Carbon Atoms | Structure |
|---|---|---|
| 17 | | 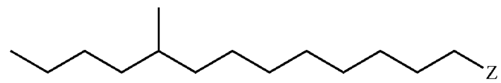 |
| 18 | 14 | 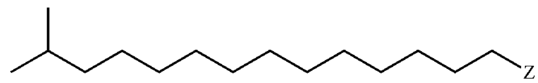 |
| 19 | | 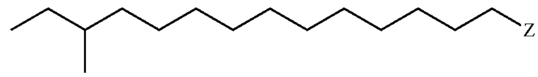 |
| 20 | | 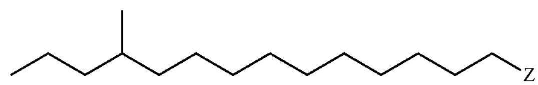 |
| 21 | | 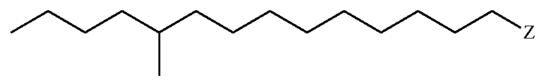 |
| 22 | 15 | 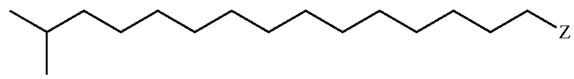 |
| 23 | | 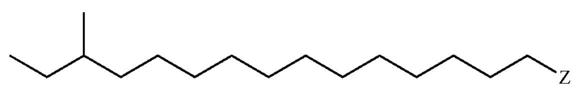 |
| 24 | | 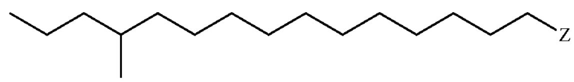 |
| 25 | | 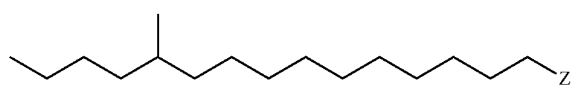 |
| 26 | | 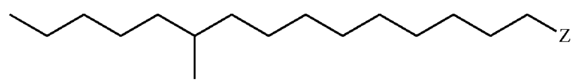 |
| 27 | 16 | 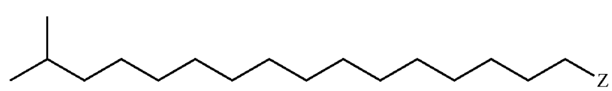 |
| 28 | | 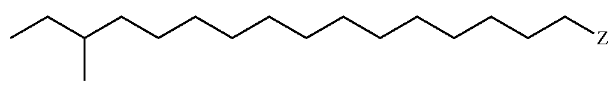 |
| 29 | | 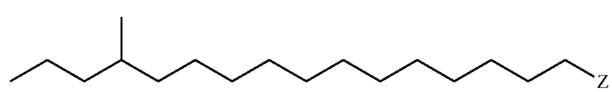 |
| 30 | | 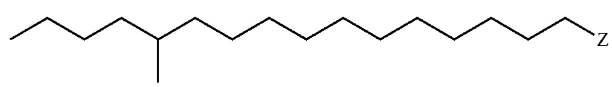 |
| 31 | | 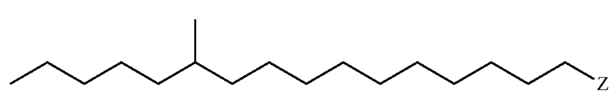 |
| 32 | 17 | 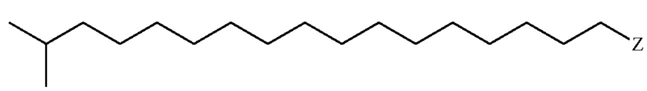 |

TABLE A-continued
Compounds with 1 Methyl Branch
| Compound # | # Carbon Atoms | Structure |
|---|---|---|
| 33 | | 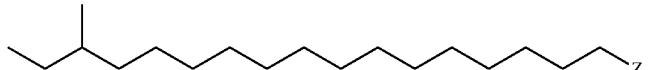 |
| 34 | | 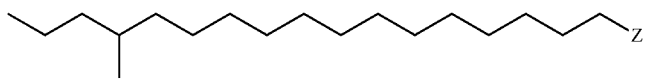 |
| 35 | | 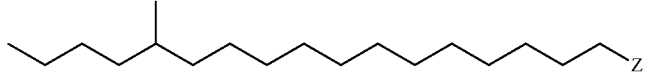 |
| 36 | | 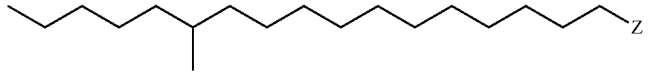 |
| 37 | 18 | 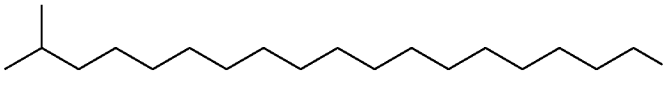 |
| 38 | | 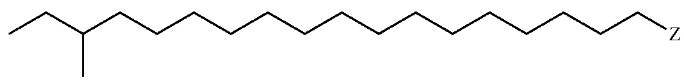 |
| 39 | | 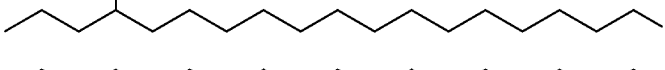 |
| 40 | | 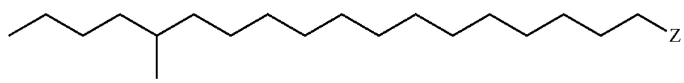 |
| 41 | | 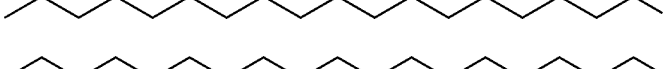 |
| 42 | | 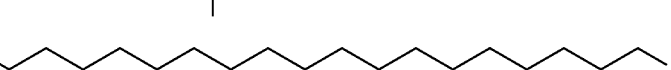 |
| 43 | 19 | 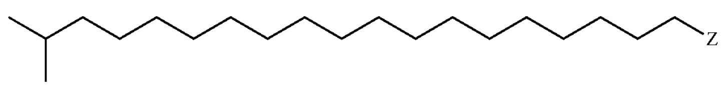 |
| 44 | | 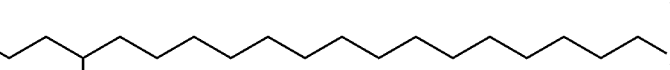 |
| 45 | | 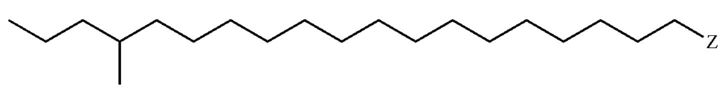 |
| 46 | | 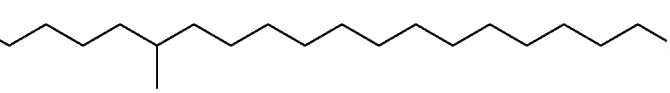 |
| 47 | | 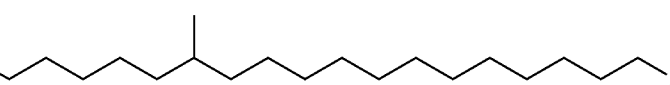 |
| 48 | | 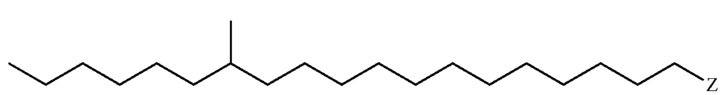 |

TABLE A-continued

Compounds with 1 Methyl Branch

| Compound # | # Carbon Atoms | Structure |
|---|---|---|
| 49 | 20 | 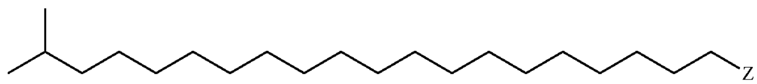 |
| 50 | | 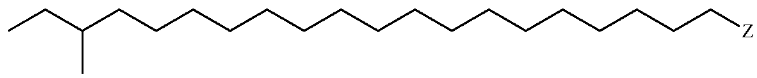 |
| 51 | | 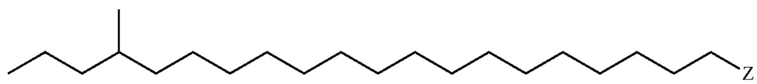 |
| 52 | | 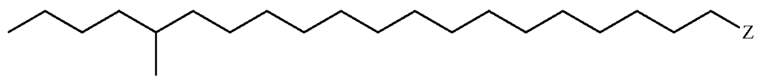 |
| 53 | | 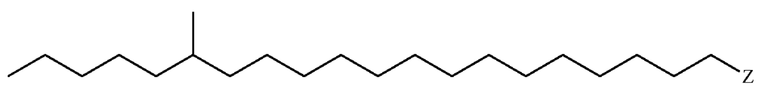 |
| 54 | | 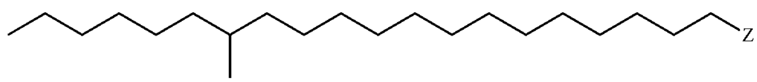 |
| 55 | | 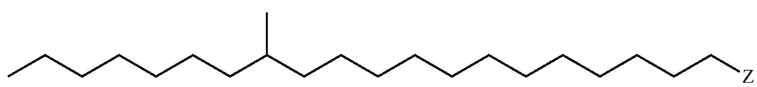 |
| 56 | 21 | 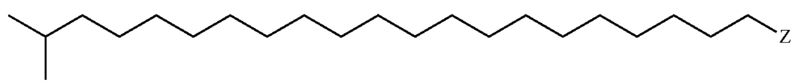 |
| 57 | | 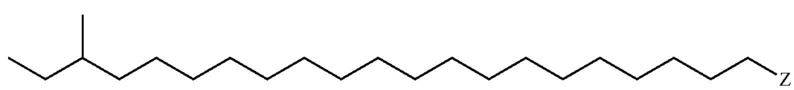 |
| 58 | | 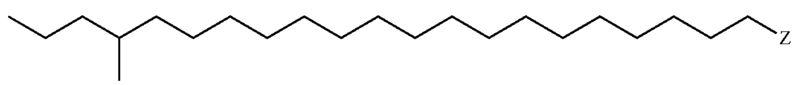 |
| 59 | | 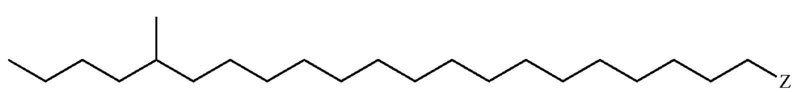 |
| 60 | | 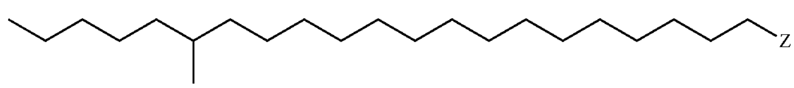 |
| 61 | | 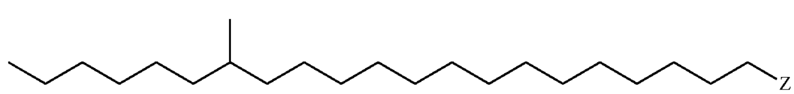 |
| 62 | | 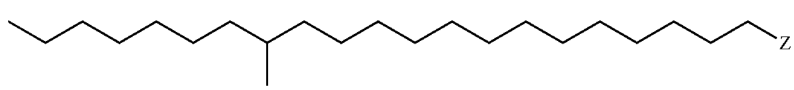 |
| 63 | 22 | 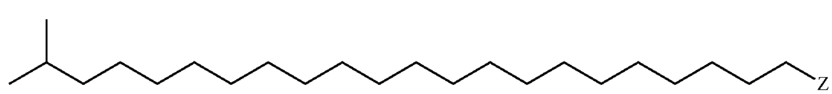 |
| 64 | | 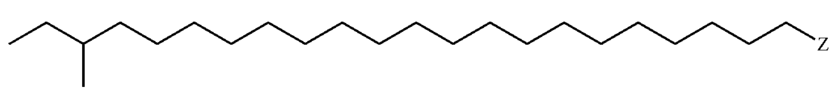 |

TABLE A-continued
Compounds with 1 Methyl Branch
| Compound # | # Carbon Atoms | Structure |
|---|---|---|
| 65 | | 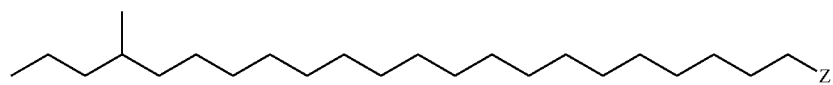 |
| 66 | | 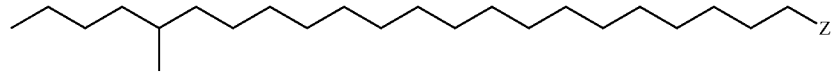 |
| 67 | | 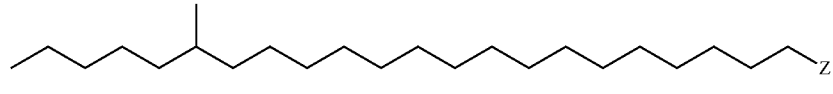 |
| 68 | | 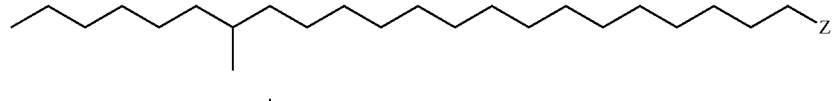 |
| 69 | | 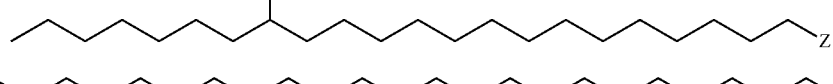 |
| 70 | 23 | 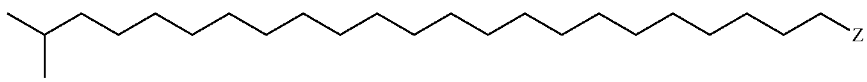 |
| 71 | | 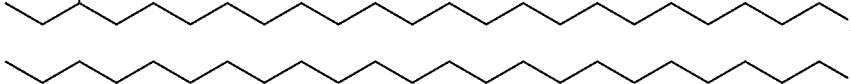 |
| 72 | | 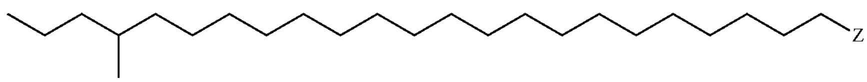 |
| 73 | | 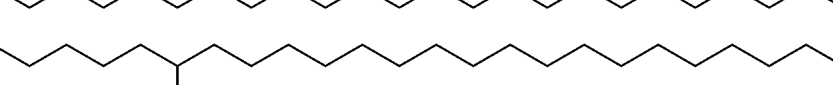 |
| 74 | | 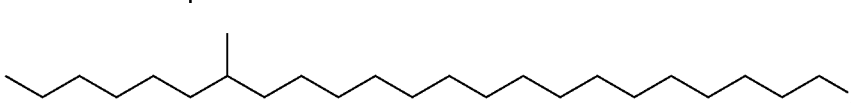 |
| 75 | | 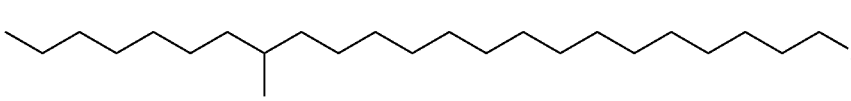 |
| 76 | | 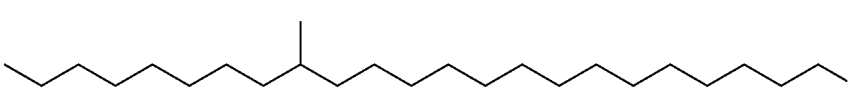 |
| 77 | | 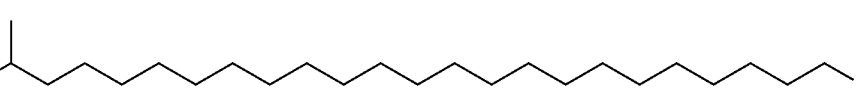 |
| 78 | 24 | 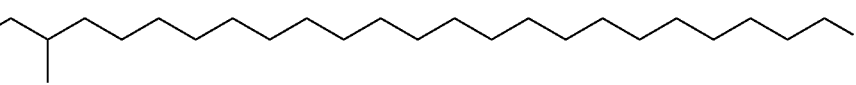 |
| 89 | | 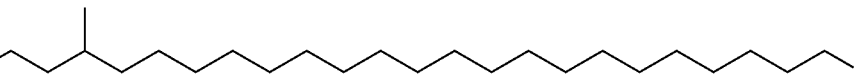 |
| 80 | | 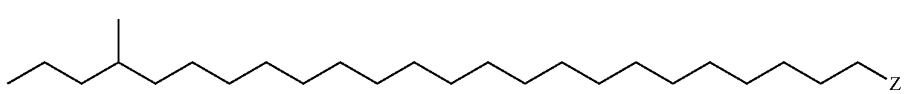 |

TABLE A-continued

Compounds with 1 Methyl Branch

| Compound # | # Carbon Atoms | Structure |
|---|---|---|
| 81 | | 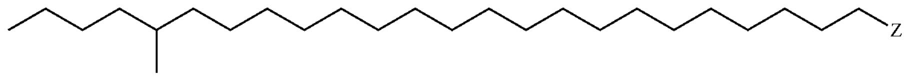 |
| 82 | | 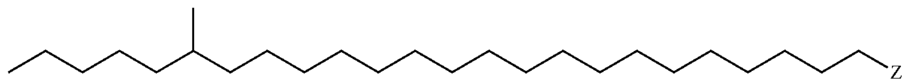 |
| 83 | | 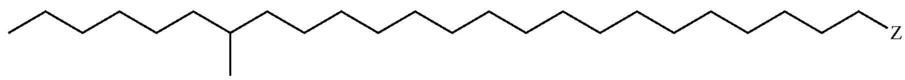 |
| 84 | | 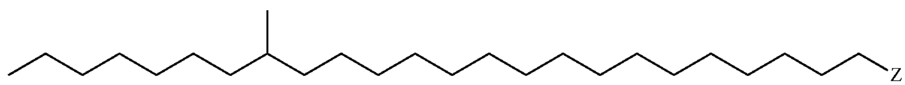 |
| 85 | | 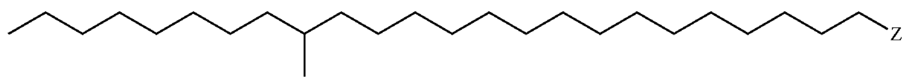 |
| 86 | 25 | 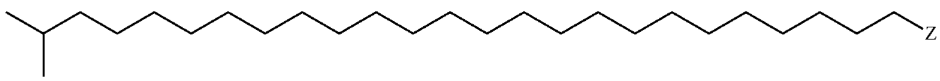 |
| 87 | | 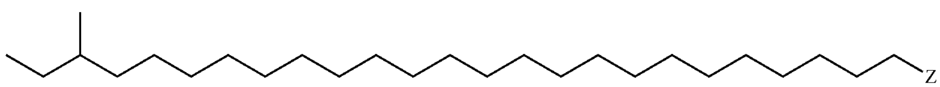 |
| 88 | | 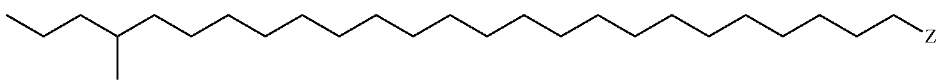 |
| 89 | | 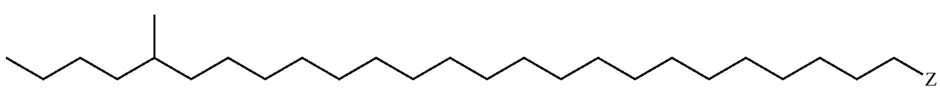 |
| 90 | | 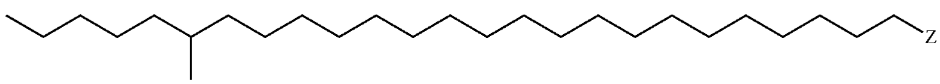 |
| 91 | | 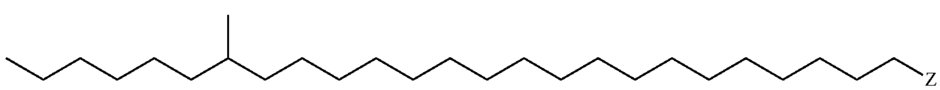 |
| 92 | | 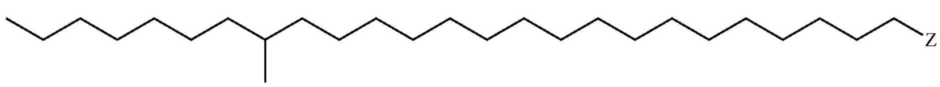 |
| 93 | | 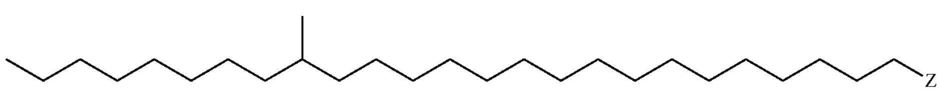 |
| 94 | | 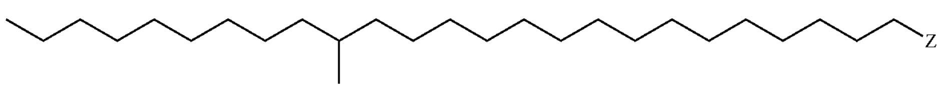 |
| 95 | 26 | 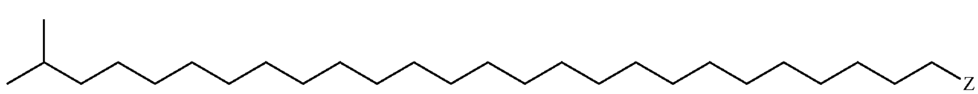 |
| 96 | | 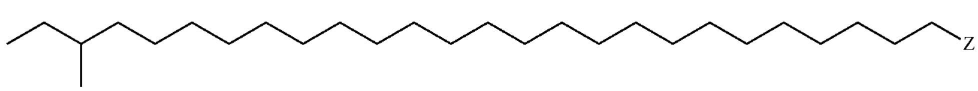 |

TABLE A-continued

Compounds with 1 Methyl Branch

| Compound # | # Carbon Atoms | Structure |
|---|---|---|
| 97 | | 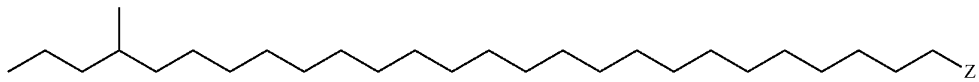 |
| 98 | | 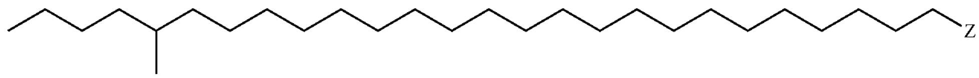 |
| 99 | | 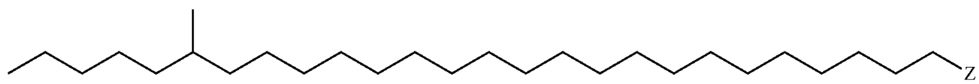 |
| 100 | | 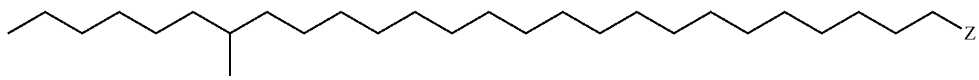 |
| 101 | | 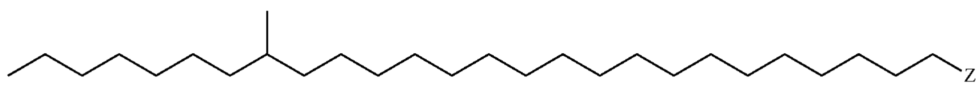 |
| 102 | | 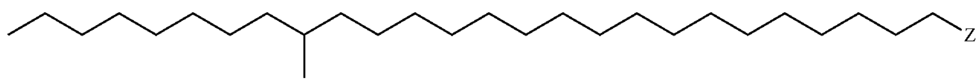 |
| 103 | | 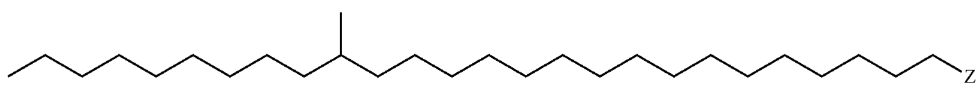 |
| 104 | 27 | 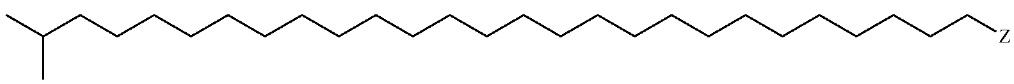 |
| 105 | | 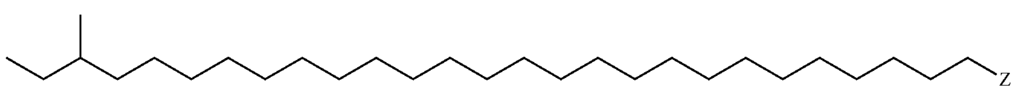 |
| 106 | | 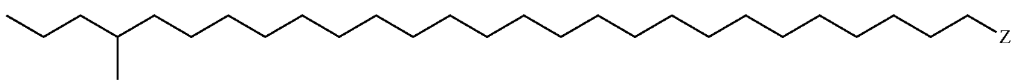 |
| 107 | | 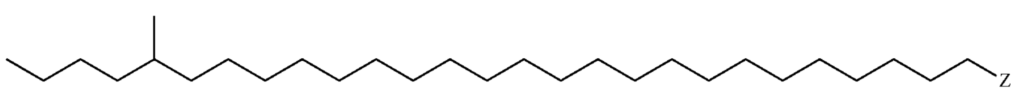 |
| 108 | | 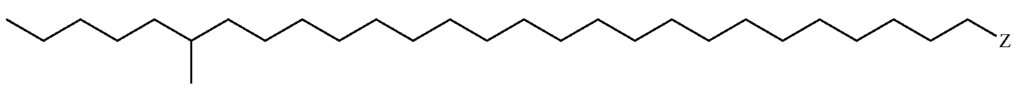 |
| 109 | | 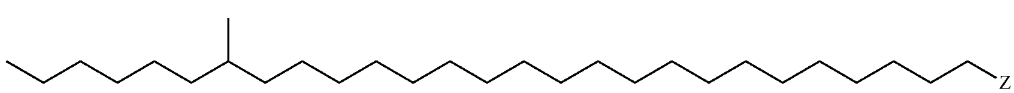 |
| 110 | | 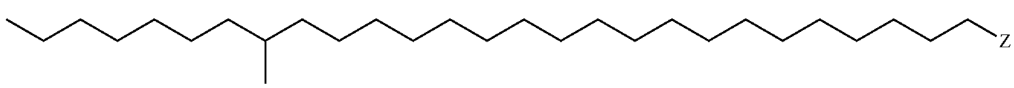 |
| 111 | | 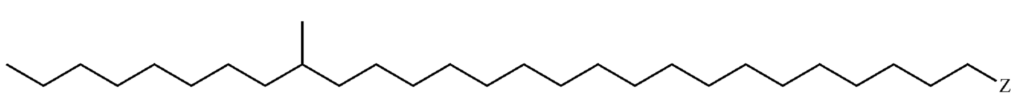 |
| 112 | | 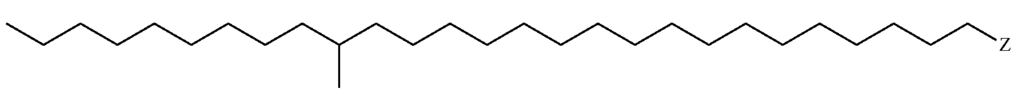 |

TABLE A-continued
Compounds with 1 Methyl Branch
| Compound # | # Carbon Atoms | Structure |
|---|---|---|
| 113 | 28 | 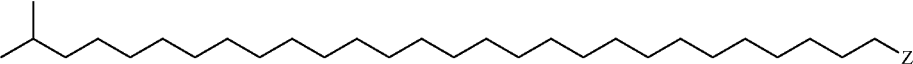 |
| 114 | | 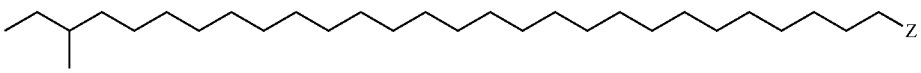 |
| 115 | | 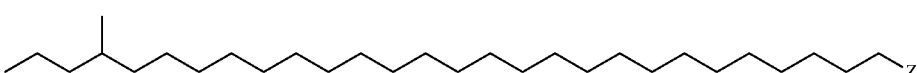 |
| 116 | | 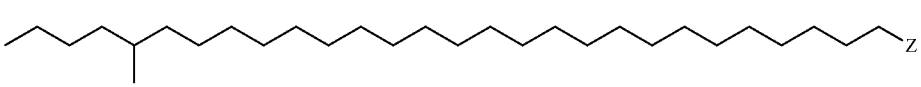 |
| 117 | | 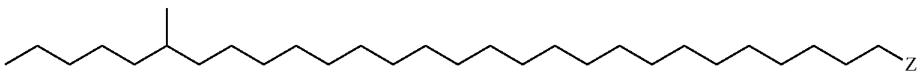 |
| 118 | | 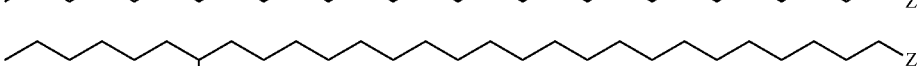 |
| 119 | | 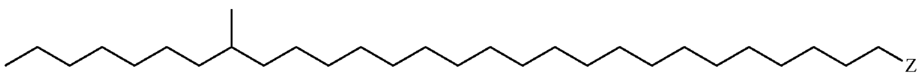 |
| 120 | | 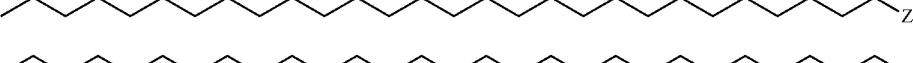 |
| 121 | | 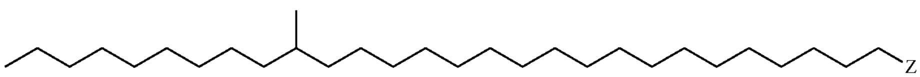 |
| 122 | | 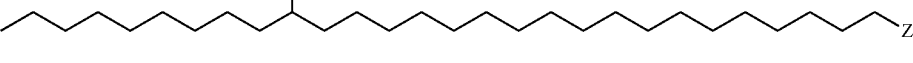 |
| 123 | 29 | 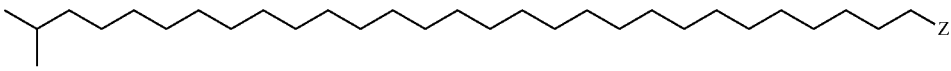 |
| 124 | | 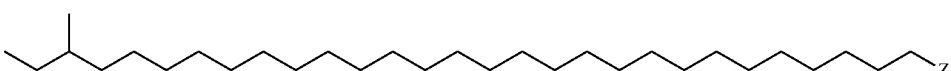 |
| 125 | | 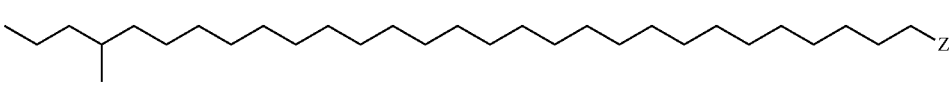 |
| 126 | | 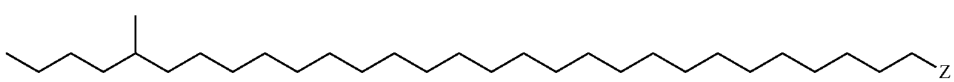 |
| 127 | | 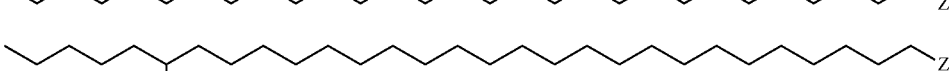 |
| 128 | | 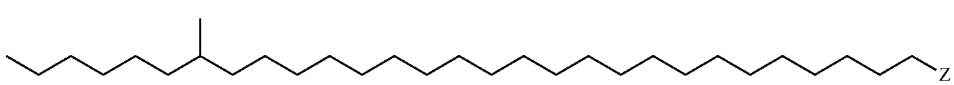 |
| 129 | | 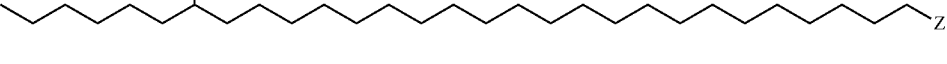 |

TABLE A-continued
Compounds with 1 Methyl Branch
| Compound # | # Carbon Atoms | Structure |
|---|---|---|
| 130 | | 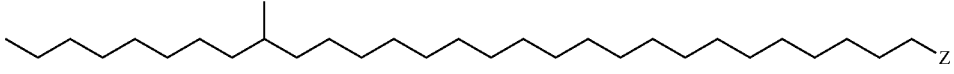 |
| 131 | | 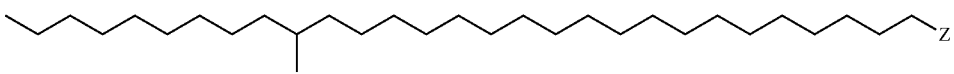 |
| 132 | | 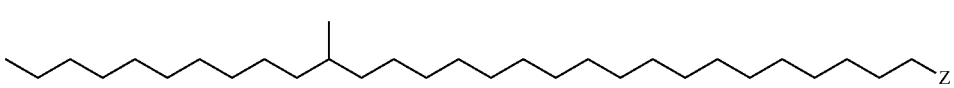 |
| 133 | 30 | 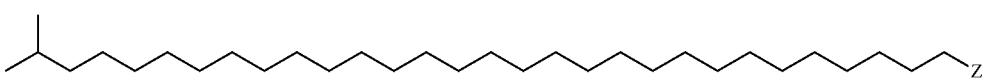 |
| 134 | | 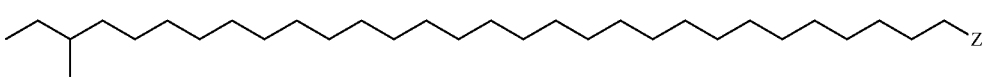 |
| 135 | | 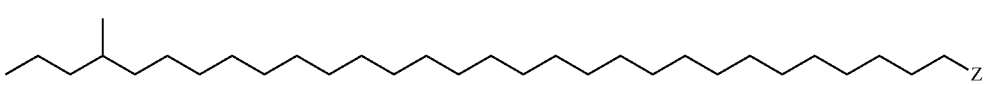 |
| 136 | | 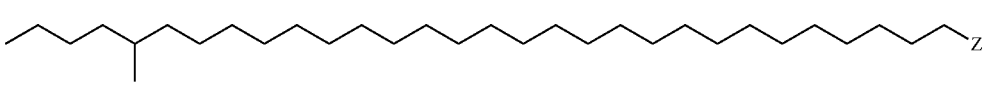 |
| 137 | | 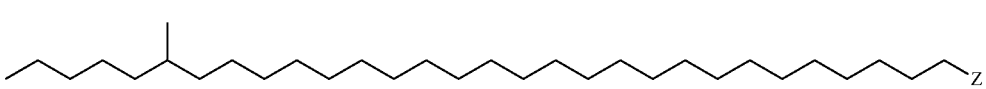 |
| 138 | | 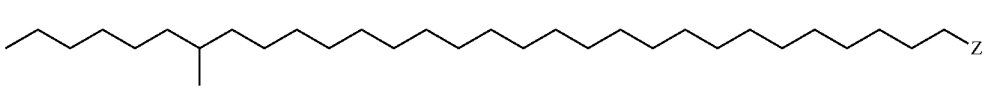 |
| 139 | | 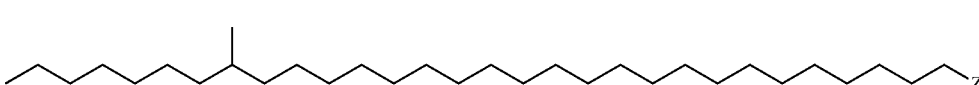 |
| 140 | | 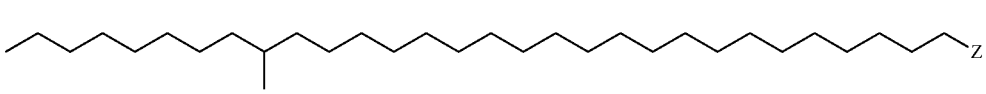 |
| 141 | | 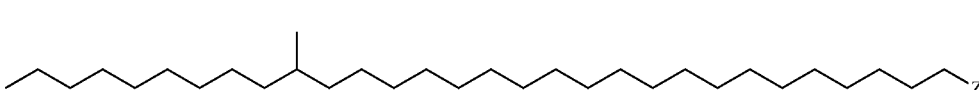 |
| 142 | | 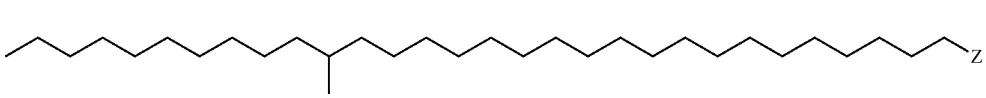 |
| 143 | | 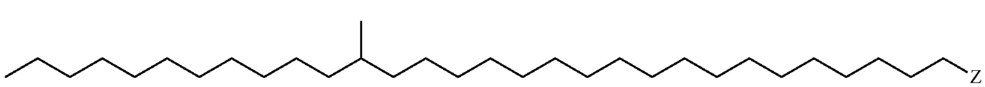 |

TABLE B

Compounds with 2 Methyl Branches

| Compound # | Structure |
|---|---|
| 1 | (structure with $(CH_2)_{6-28}$-Z) |
| 2 | (structure with $(CH_2)_{5-27}$-Z) |
| 3 | (structure with $(CH_2)_{6-26}$-Z) |
| 4 | (structure with $(CH_2)_{6-26}$-Z) |
| 5 | (structure with $(CH_2)_{8-25}$-Z) |
| 6 | (structure with $(CH_2)_{8-25}$-Z) |
| 7 | (structure with $(CH_2)_{8-25}$-Z) |
| 8 | (structure with $(CH_2)_{9-24}$-Z) |
| 9 | (structure with $(CH_2)_{9-24}$-Z) |
| 10 | (structure with $(CH_2)_{9-24}$-Z) |
| 11 | (structure with $(CH_2)_{9-24}$-Z) |
| 12 | (structure with $(CH_2)_{11-23}$-Z) |
| 13 | (structure with $(CH_2)_{11-23}$-Z) |
| 14 | (structure with $(CH_2)_{11-23}$-Z) |
| 15 | (structure with $(CH_2)_{11-23}$-Z) |
| 16 | (structure with $(CH_2)_{11-23}$-Z) |
| 17 | (structure with $(CH_2)_{12-22}$-Z) |
| 18 | (structure with $(CH_2)_{12-22}$-Z) |
| 19 | (structure with $(CH_2)_{12-22}$-Z) |
| 20 | (structure with $(CH_2)_{12-22}$-Z) |
| 21 | (structure with $(CH_2)_{12-22}$-Z) |
| 22 | (structure with $(CH_2)_{12-22}$-Z) |
| 23 | (structure with $(CH_2)_{14-21}$-Z) |
| 24 | (structure with $(CH_2)_{14-21}$-Z) |

TABLE B-continued

Compounds with 2 Methyl Branches

| Compound # | Structure |
|---|---|
| 25 | (structure, (14-21)) |
| 26 | (structure, (14-21)) |
| 27 | (structure, (14-21)) |
| 28 | (structure, (14-21)) |
| 29 | (structure, (14-21)) |
| 30 | (structure, (15-20)) |
| 31 | (structure, (15-20)) |
| 32 | (structure, (15-20)) |
| 33 | (structure, (15-20)) |
| 34 | (structure, (15-20)) |
| 35 | (structure, (15-20)) |
| 36 | (structure, (15-20)) |
| 37 | (structure, (15-20)) |
| 38 | (structure, (17-19)) |
| 39 | (structure, (17-19)) |
| 40 | (structure, (17-19)) |
| 41 | (structure, (17-19)) |
| 42 | (structure, (17-19)) |
| 43 | (structure, (17-19)) |
| 44 | (structure, (17-19)) |
| 45 | (structure, (17-19)) |
| 46 | (structure, (17-19)) |
| 47 | (structure, (18)) |

TABLE B-continued

Compounds with 2 Methyl Branches

| Compound # | Structure |
|---|---|
| 48 | (structure with Z, subscript 18) |
| 49 | (structure with Z, subscript 18) |
| 50 | (structure with Z, subscript 18) |
| 51 | (structure with Z, subscript 18) |
| 52 | (structure with Z, subscript 18) |
| 53 | (structure with Z, subscript 18) |
| 54 | (structure with Z, subscript 18) |
| 55 | (structure with Z, subscript 18) |
| 56 | (structure with Z, subscript 18) |

TABLE C

Compounds with 3 Methyl Branches

| Compound # | Structure |
|---|---|
| 1 | (structure with Z, subscript 6-26) |
| 2 | (structure with Z, subscript 8-25) |
| 3 | (structure with Z, subscript 8-25) |
| 4 | (structure with Z, subscript 8-25) |
| 5 | (structure with Z, subscript 9-24) |
| 6 | (structure with Z, subscript 9-24) |
| 7 | (structure with Z, subscript 9-24) |
| 8 | (structure with Z, subscript 9-24) |
| 9 | (structure with Z, subscript 9-24) |
| 10 | (structure with Z, subscript 11-23) |
| 11 | (structure with Z, subscript 11-23) |
| 12 | (structure with Z, subscript 11-23) |
| 13 | (structure with Z, subscript 11-23) |

TABLE C-continued

Compounds with 3 Methyl Branches

| Compound # | Structure |
|---|---|
| 14 | (structure with Z, subscript 11-23) |
| 15 | (structure with Z, subscript 11-23) |
| 16 | (structure with Z, subscript 11-23) |
| 17 | (structure with Z, subscript 11-23) |
| 18 | (structure with Z, subscript 11-23) |
| 19 | (structure with Z, subscript 11-23) |
| 20 | (structure with Z, subscript 12-22) |
| 21 | (structure with Z, subscript 12-22) |
| 22 | (structure with Z, subscript 12-22) |
| 23 | (structure with Z, subscript 12-22) |
| 24 | (structure with Z, subscript 12-22) |
| 25 | (structure with Z, subscript 12-22) |
| 26 | (structure with Z, subscript 12-22) |
| 27 | (structure with Z, subscript 12-22) |
| 28 | (structure with Z, subscript 12-22) |
| 29 | (structure with Z, subscript 12-22) |
| 30 | (structure with Z, subscript 12-22) |
| 31 | (structure with Z, subscript 12-22) |
| 32 | (structure with Z, subscript 12-22) |
| 33 | (structure with Z, subscript 12-22) |
| 34 | (structure with Z, subscript 12-22) |
| 35 | (structure with Z, subscript 14-21) |
| 36 | (structure with Z, subscript 14-21) |
| 37 | (structure with Z, subscript 14-21) |

TABLE C-continued

Compounds with 3 Methyl Branches

| Compound # | Structure |
|---|---|
| 38 | (structure with Z, (CH₂)₁₄₋₂₁) |
| 39 | (structure with Z, (CH₂)₁₄₋₂₁) |
| 40 | (structure with Z, (CH₂)₁₄₋₂₁) |
| 41 | (structure with Z, (CH₂)₁₄₋₂₁) |
| 42 | (structure with Z, (CH₂)₁₄₋₂₁) |
| 43 | (structure with Z, (CH₂)₁₄₋₂₁) |
| 44 | (structure with Z, (CH₂)₁₄₋₂₁) |
| 45 | (structure with Z, (CH₂)₁₄₋₂₁) |
| 46 | (structure with Z, (CH₂)₁₄₋₂₁) |
| 47 | (structure with Z, (CH₂)₁₄₋₂₁) |
| 48 | (structure with Z, (CH₂)₁₄₋₂₁) |
| 49 | (structure with Z, (CH₂)₁₄₋₂₁) |
| 50 | (structure with Z, (CH₂)₁₄₋₂₁) |
| 51 | (structure with Z, (CH₂)₁₄₋₂₁) |
| 52 | (structure with Z, (CH₂)₁₄₋₂₁) |
| 53 | (structure with Z, (CH₂)₁₄₋₂₁) |
| 54 | (structure with Z, (CH₂)₁₄₋₂₁) |
| 55 | (structure with Z, (CH₂)₁₄₋₂₁) |
| 56 | (structure with Z, (CH₂)₁₅₋₂₀) |
| 57 | (structure with Z, (CH₂)₁₅₋₂₀) |
| 58 | (structure with Z, (CH₂)₁₅₋₂₀) |
| 59 | (structure with Z, (CH₂)₁₅₋₂₀) |
| 60 | (structure with Z, (CH₂)₁₅₋₂₀) |
| 61 | (structure with Z, (CH₂)₁₅₋₂₀) |

TABLE C-continued
Compounds with 3 Methyl Branches
| Compound # | Structure |
|---|---|
| 62 | 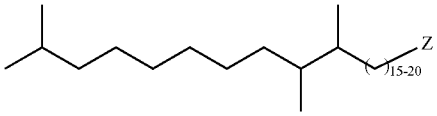 |
| 63 | 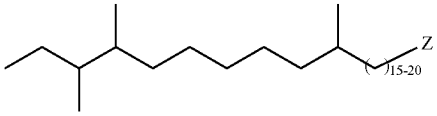 |
| 64 | 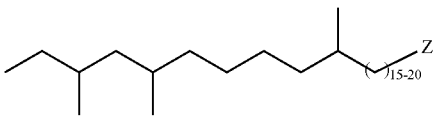 |
| 65 | 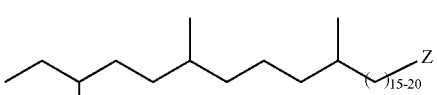 |
| 66 | 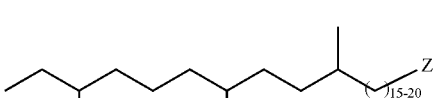 |
| 67 | 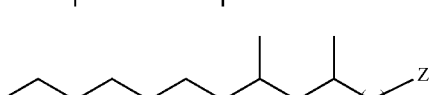 |
| 68 | 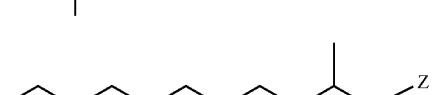 |
| 69 | 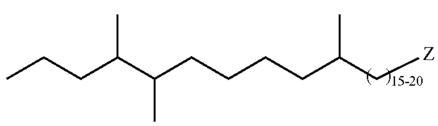 |
| 70 | 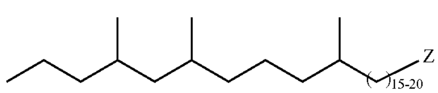 |
| 71 | 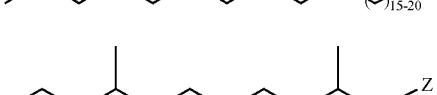 |
| 72 | 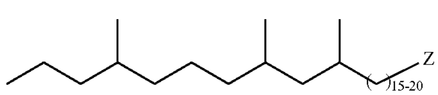 |
| 73 | 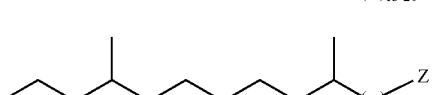 |
| 74 | 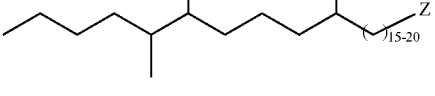 |
| 75 | 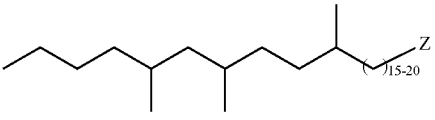 |
| 76 | 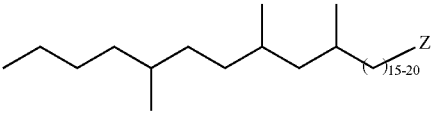 |
| 77 | 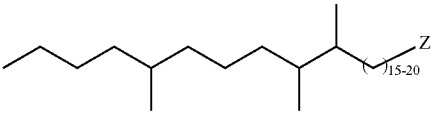 |
| 78 | 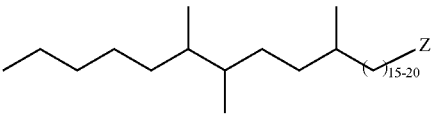 |
| 79 | 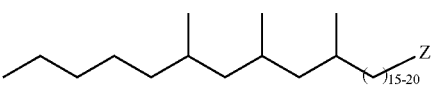 |
| 80 | 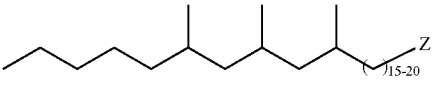 |
| 81 | 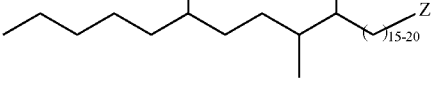 |
| 82 | 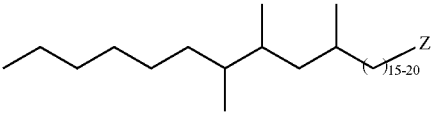 |
| 83 | 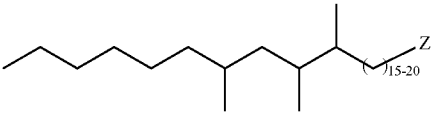 |
| 84 | 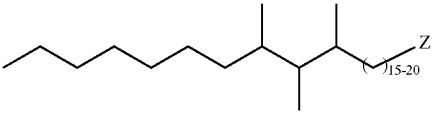 |
| 85 | 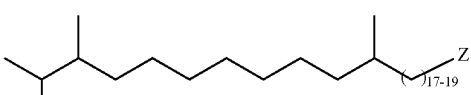 |

TABLE C-continued

Compounds with 3 Methyl Branches

| Compound # | Structure |
|---|---|
| 86 | 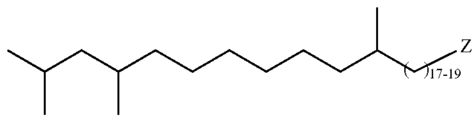 |
| 87 | 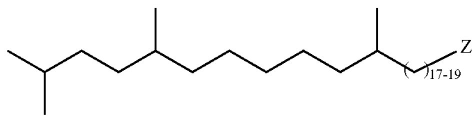 |
| 88 | 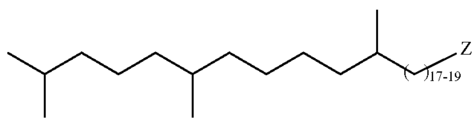 |
| 89 | 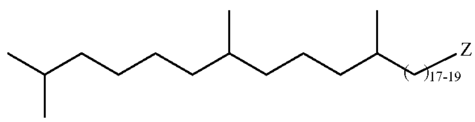 |
| 90 | 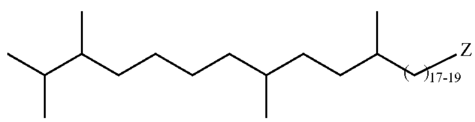 |
| 91 | 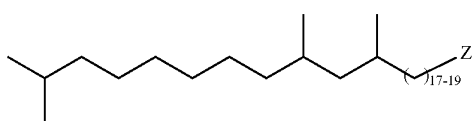 |
| 92 | 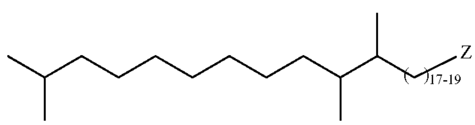 |
| 93 | 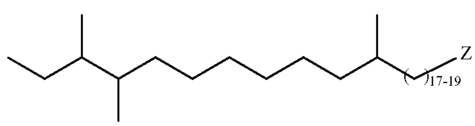 |
| 94 | 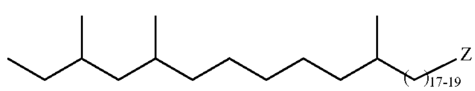 |
| 95 | 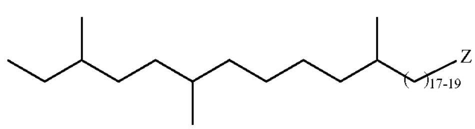 |
| 96 | 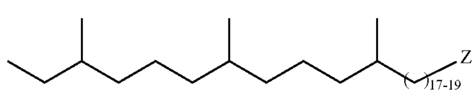 |
| 97 | 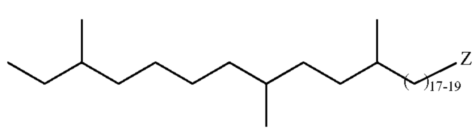 |
| 98 | |
| 99 | |
| 100 | |
| 101 | |
| 102 | |
| 103 | |
| 104 | |
| 105 | |
| 106 | |
| 107 | |
| 108 | |
| 109 | |

TABLE C-continued

Compounds with 3 Methyl Branches

| Compound # | Structure |
|---|---|
| 110 | (structure with Z, subscript 17-19) |
| 111 | (structure with Z, subscript 17-19) |
| 112 | (structure with Z, subscript 17-19) |
| 113 | (structure with Z, subscript 17-19) |
| 114 | (structure with Z, subscript 17-19) |
| 115 | (structure with Z, subscript 17-19) |
| 116 | (structure with Z, subscript 17-19) |
| 117 | (structure with Z, subscript 17-19) |
| 118 | (structure with Z, subscript 17-19) |
| 119 | (structure with Z, subscript 17-19) |
| 120 | (structure with Z, subscript 17-19) |
| 121 | (structure with Z, subscript 18) |
| 122 | (structure with Z, subscript 18) |
| 123 | (structure with Z, subscript 18) |
| 124 | (structure with Z, subscript 18) |
| 125 | (structure with Z, subscript 18) |
| 126 | (structure with Z, subscript 18) |
| 127 | (structure with Z, subscript 18) |
| 128 | (structure with Z, subscript 18) |
| 129 | (structure with Z, subscript 18) |
| 130 | (structure with Z, subscript 18) |
| 131 | (structure with Z, subscript 18) |
| 132 | (structure with Z, subscript 18) |
| 133 | (structure with Z, subscript 18) |

TABLE C-continued
Compounds with 3 Methyl Branches
| Compound # | Structure |
|---|---|
| 134 | 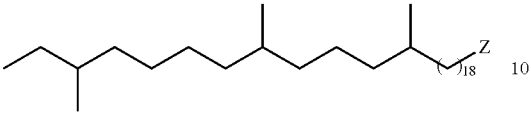 |
| 135 | 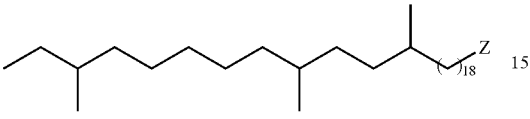 |
| 136 | 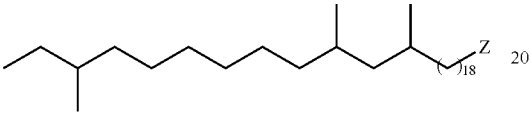 |
| 137 | 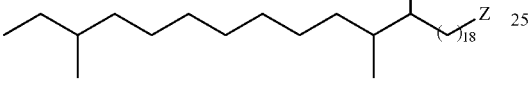 |
| 138 | 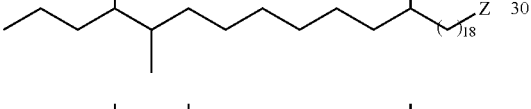 |
| 139 | 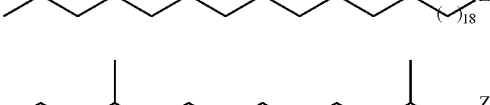 |
| 140 | 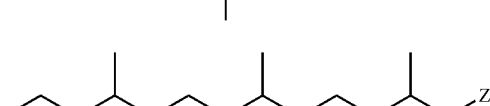 |
| 141 | 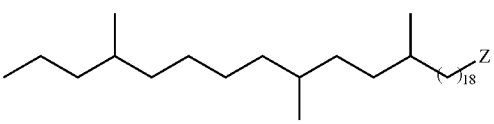 |
| 142 | 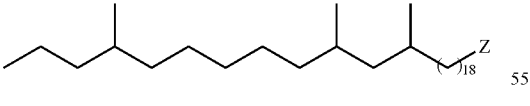 |
| 143 | 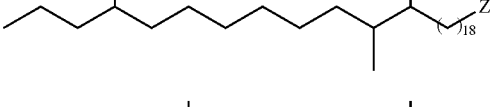 |
| 144 | 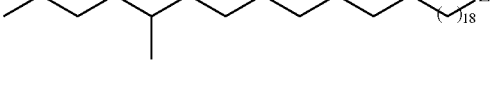 |
| 145 |  |
| 146 | 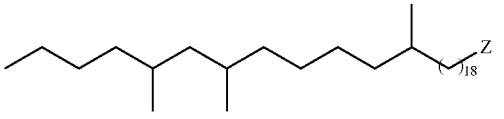 |
| 147 | 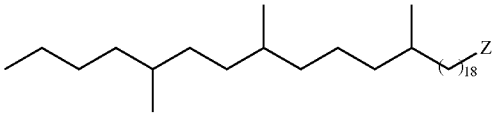 |
| 148 | 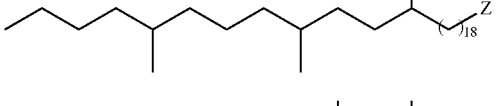 |
| 149 | 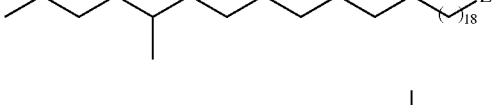 |
| 150 | 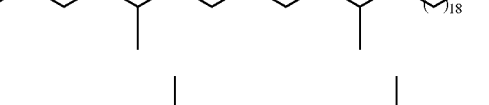 |
| 151 | 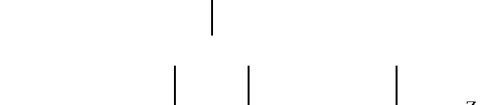 |
| 152 | 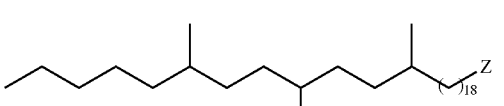 |
| 153 | 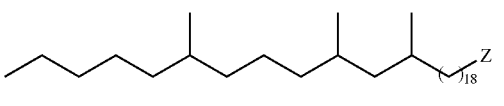 |
| 154 | 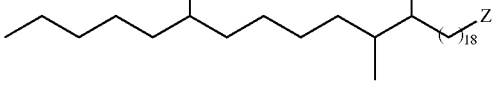 |
| 155 | 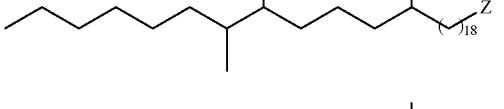 |
| 156 | 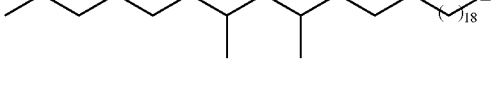 |
| 157 | 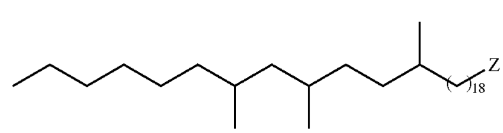 |

TABLE C-continued

Compounds with 3 Methyl Branches

| Compound # | Structure |
|---|---|
| 158 | 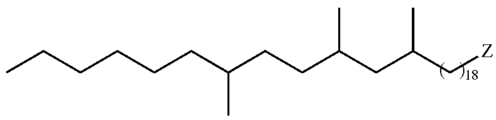 |
| 159 | 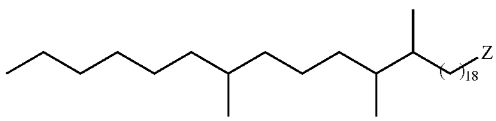 |
| 160 | 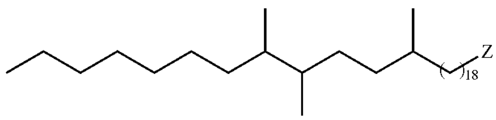 |
| 161 | 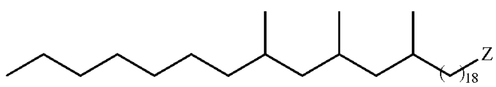 |
| 162 | 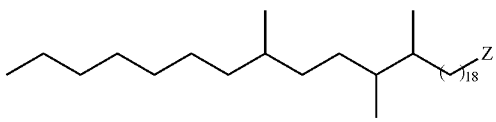 |
| 163 | 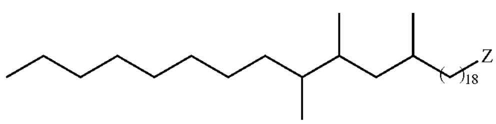 |
| 164 | 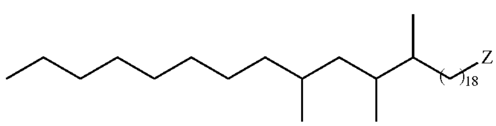 |
| 165 | 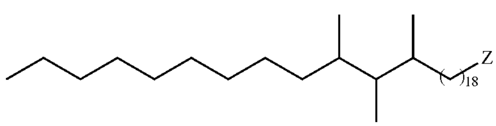 |

The mixtures of the invention are advantageous for use in cleaning compositions (when derivatized to contain, for example, sulfate end groups) and conditioning compositions (when derivatized to contain, for example, hydroxy or cationic end groups on long chain compounds). The mixtures of the invention contain a high concentration of near terminal-branched compounds that can be stored indefinitely and incorporated into a cleaning composition or conditioning composition at will. The light degree of branching on the near-terminal branched compounds allows facile biodegradation.

In household cleaning compositions, the unique structure of the near terminal-branched compounds, when the correct chain lengths and mixtures are used for said purpose, provides for good cleaning ability in cold, hard water, high solubility, good grease removal, high sudsing ability, and lack of a visible residue on hard surfaces and fabrics. This lack of a visible residue results in low or no odor after use. Further, compositions of the invention have good compaction without low temperature stability issues, dilute quickly and easily, even in cold water, and, in some embodiments, do not precipitate out of solution. The aforementioned properties are highly desired in dishcare, laundry, and shampoo applications.

In personal care compositions, the near-terminal branched compounds in the mixtures can act as, for example, surfactants, conditioners, or cosurfactant performance boosting agents. In these applications, the mixtures of the invention provide higher tolerance to precipitation with calcium and magnesium in hard water, have excellent rinsability, particularly with respect to the speed of rinsability, and improved cleaning in cooler wash temperatures.

Anionic surfactants derived from the mixtures of the invention advantageously have good solubility at low temperatures. Nonionic surfactants derived from the mixtures of the invention advantageously have low melting points. Cationic surfactants derived from the mixtures of the invention can complex with anionic surfactants without inducing crystallization. This ability to avoid crystallization is especially advantageous during storage or transport conditions.

In another embodiment, the composition of the invention contains a mixture of at least two compounds selected from the group consisting of:

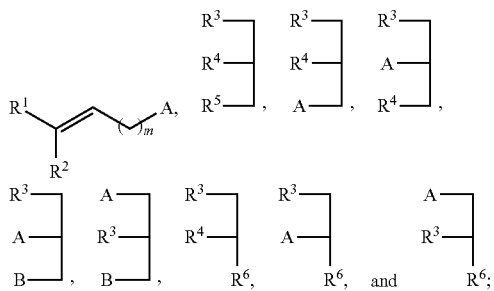

wherein A and B are each independently OH or O(C=O)$R^7$;

$R^1$ is hydrogen, methyl, or ethyl;

$R^2$ is $(C_1$-$C_n)$alkyl or $(C_1$-$C_n)$alkenyl, having 0, 1, 2, or 3 $(C_1$-$C_3)$alkyl branches, wherein when $R^1$ is H, $R^2$ has 1, 2, or 3 $(C_1$-$C_3)$alkyl branches; and when $R^1$ is methyl or ethyl, $R^2$ has 0, 1, or 2 $(C_1$-$C_3)$alkyl branches;

$R^3$, $R^4$, and $R^5$ are each independently

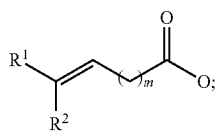

$R^6$ is hydrogen, methyl, or ethyl;

$R^7$ is $(C_1$-$C_{26})$alkyl; and, m is 5-37 and n is 1-33, wherein m+n is 6-38; preferably m is 7-27 and n is 1-23, wherein m+n is 8-28; for example, when m is 7, n is 9, and when m is 11, n is 17.

In some embodiments, at least one of

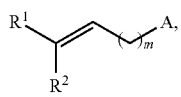

$R^3$, $R^4$, or $R^5$ contains one or more sites of unsaturation within the region represented by —$(CH_2)_m$—. For example, one embodiment of

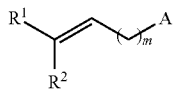

when m is 11 includes the below structure:

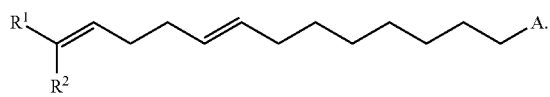

As another example, one embodiment for $R^3$ when m is 5 includes the below structure:

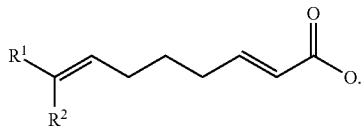

The present invention also is directed to derivatives of the above compounds. For example, substituents A and B of the above structures can be functionalized by methods well known in the art to provide functionalized anionic, cationic, and nonionic materials, such as by alkoxylation, sulfation, sulfonation, and transesterification, for example.

The at least two compounds have different chemical structures and are present in the composition in at least about 50 wt %, preferably at least about 75 wt %, more preferably at least about 90 wt %, for example, about 95 wt %, up to and including about 100 wt %, based on the total weight of the composition.

The at least two compounds independently can have a length of about 10 carbon atoms to about 40 carbon atoms, preferably of about 10 carbon atoms to about 30 carbon atoms. Preferably, the at least two compounds will include some degree of mixed chain lengths to minimize crystallinity. The exact length of the at least two compounds depends on their desired use, as previously described herein.

The branching on the at least two compounds occurs within 40% of the nonfunctionalized terminus of the longest carbon chain, as previously described herein. For example, the branching occurs up to the omega-6 position, preferably up to the omega-5 position, more preferably up to the omega-4 position, even more preferably up to the omega-3 position, provided that the position of the branch is within 40% of the nonfunctionalized terminus of the longest carbon chain. In some preferred embodiments, branching occurs on the omega-1 position, the omega-2 position, or on both the omega-1 and omega-2 positions. Thus, in some embodiments when $R^2$ has 5 or less carbon atoms in its longest chain, $R^1$ can be hydrogen, methyl, or ethyl. In other embodiments, when $R^2$ has 6 or more carbon atoms in its longest chain, $R^1$ is hydrogen.

The near terminal-branching on the at least two compounds is composed of ($C_1$-$C_3$)alkyl moieties. For example, the branches can include methyl moieties, ethyl moieties, propyl moieties, isopropyl moieties, and mixtures thereof. Preferably, the branches include methyl moieties, ethyl moieties, and mixtures thereof. More preferably, the branches include methyl moieties.

The at least two near terminal-branched compounds include one branch, two branches, or three branches. In embodiments when $R^2$ has three branches, $R^1$ is hydrogen. In some embodiments, the at least two compounds have two or three branches and two of these branches are at the omega-1 position. In other embodiments, the at least two compounds have two or three branches and none of the branches are geminal. In preferred embodiments, the at least two near terminal-branched compounds each have one branch.

The mixtures in this embodiment of the invention can include 10 wt %, about 20 wt %, about 30 wt %, about 40 wt %, about 50 wt %, about 60 wt %, about 70 wt %, about 80 wt % and about 90 wt % of iso compounds, based on the total weight of near terminal-branched compounds. In some preferred embodiments, the mixture of the invention includes less than 50 wt % of the iso compound. For example, the mixture can include about 1 wt % to about 40 wt %, or about 10 wt % to about 30 wt % of iso compounds, based on the total weight of near terminal-branched compounds. In other embodiments, the mixtures of the invention include about 20 wt % or about 40 wt % of the iso compound, based on the total weight of near terminal-branched compounds. In some embodiments, the near terminal-branched compounds include only anteiso compounds.

The compositions containing the mixtures of the at least two compounds are substantially free of secondary hydroxy compounds (i.e., hydroxy fatty acids/alcohols and iso-hydroxy fatty acids/alcohols), as previously described herein. For example, the compositions of the invention contain no more than about 2 wt % of secondary hydroxy compounds, preferably no more than about 1 wt % of secondary hydroxy compounds, even more preferably 0 wt % of secondary hydroxy compounds, based on the total weight of the composition.

The compositions containing the mixtures of the at least two compounds optionally include a linear compound, a mid-chain branched compound, or mixtures thereof in an amount of no more than about 50 wt %, preferably no more than 10 wt %, for example, no more than about 2 wt %, based on the total weight of the composition. The specific amount of linear compounds and/or mid-chain branched compounds depends on the desired application, as previously described.

In some embodiments, the mixture of the invention is free of iso compounds, linear compounds, and/or short chain compounds.

Examples of the at least two compounds in the mixtures of this embodiment of the invention include:

| Generic Compound | Example Compound | Example Compound |
|---|---|---|

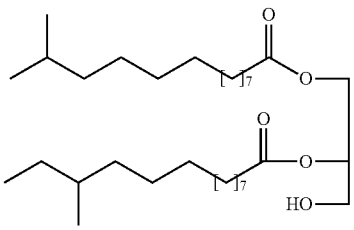

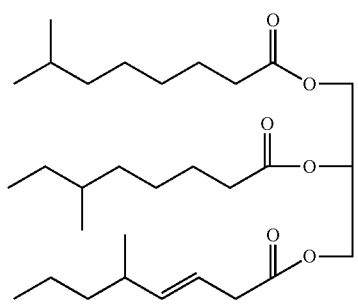

In the above examples, a hydroxy group can be functionalized to provide an anionic, cationic, or nonionic material, e.g., sulfate, sulfonate, or polyoxyalkylene, by procedures well known in the art.

It is further understood that the above compounds can be easily hydrogenated or partially hydrogenated by known methods to give, as shown below in a non-limiting example, new mixtures which are also part of the invention.

-continued

It is also understood that dealing with natural triglycerides may, in some embodiments, result in the presence of less desirable linear chains. In some embodiments, a modified triglyceride that has a mixed chain structure containing both long and short chains (shown below) may be beneficial. In other embodiments (e.g., some surfactant mixtures), however, this mixed chain structure with a long linear chain is not beneficial and may hinder cleaning properties. In other embodiments, some low levels of long, linear chains can be tolerated.

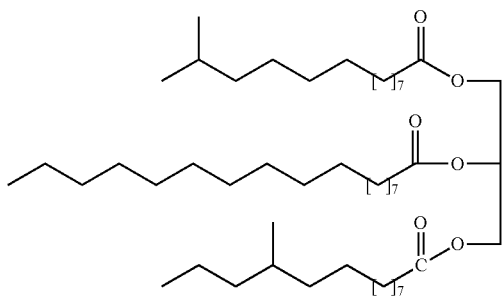

In another aspect, the composition of the invention contains a mixture of at least two compounds of Formula IV:

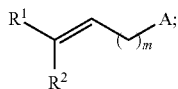

wherein, A in each of the at least two compounds is independently COOH, COO⁻M, O(C=O)$R^7$ or (C=O)O$R^7$;
$R^1$ is hydrogen, methyl, or ethyl;
$R^2$ is ($C_1$-$C_n$)alkyl or ($C_1$-$C_n$)alkenyl having 0, 1, 2, or 3 ($C_1$-$C_3$)alkyl branches, wherein when $R^1$ is H, $R^2$ has 1, 2, or 3 ($C_1$-$C_3$)alkyl branches, and when $R^1$ is methyl or ethyl, $R^2$ has 0, 1, or 2 ($C_1$-$C_3$)alkyl branches, and wherein branching occurs on carbon atoms that are within 40% of the nonfunctionalized terminus of the longest carbon chain;
$R^7$ is ($C_1$-$C_{26}$)alkyl;
M is Li⁺, Na⁺, K⁺, Ca²⁺, Mg²⁺, and

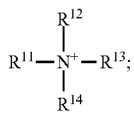

$R^{11}$, $R^{12}$, $R^{13}$, and $R^{14}$ are each independently hydrogen, ($C_1$-$C_{22}$)alkyl, ($C_1$-$C_6$)alkanol, and ($C_1$-$C_{22}$)alkenyl;
m is 5-37 and n is 1-33, wherein m+n is 6-38; preferably m is 7-27 and n is 1-23, wherein m+n is 8-28.

In this composition, when $R^1$ is H, $R^2$ has 1, 2, or 3 ($C_1$-$C_3$)alkyl branches, and when $R^1$ is methyl or ethyl, $R^2$ has 0, 1, or 2 ($C_1$-$C_3$)alkyl branches. Further, the branching occurs on carbon atoms that are within 40% of the nonfunctionalized terminus of the longest carbon chain. Further still, the composition is substantially free of secondary hydroxy compounds.

In some embodiments, at least one of

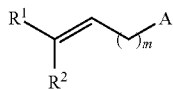

contains one or more sites of unsaturation within the region represented by —(CH$_2$)$_m$—. For example, one embodiment of

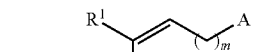

when m is 11 includes the below structure:

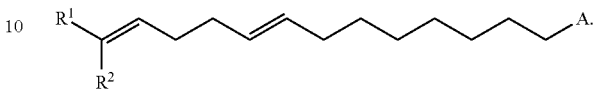

The present invention also is directed to derivatives of the above compounds. For example, substituent A of the above structure can be functionalized by methods well known in the art to provide functionalized anionic, cationic, and nonionic materials, such as by alkoxylation, sulfation, sulfonation, and transesterification, for example.

The at least two compounds have different chemical structures and are present in the composition in at least about 50 wt %, preferably at least about 75 wt %, more preferably at least about 90 wt %, for example, about 95 wt %, up to and including about 100 wt %, based on the total weight of the composition.

The at least two compounds independently can have a length of about 10 carbon atoms to about 40 carbon atoms, preferably of about 10 carbon atoms to about 30 carbon atoms. Preferably, the at least two compounds will include some degree of mixed chain lengths to minimize crystallinity. The exact length of the at least two compounds depends on their desired use, as previously described herein.

The branching on the at least two compounds occurs within 40% of the nonfunctionalized terminus of the longest carbon chain, as previously described herein. In some preferred embodiments, branching occurs on the omega-1 position, the omega-2 position, or on both the omega-1 and omega-2 positions. Thus, in some embodiments when $R^2$ has 5 or less carbon atoms in its longest chain, $R^1$ can be hydrogen, methyl, or ethyl. In other embodiments, when $R^2$ has 6 or more carbon atoms in its longest chain, $R^1$ is hydrogen.

The near terminal-branching on the at least two compounds is composed of ($C_1$-$C_3$)alkyl moieties. For example, the branches can include methyl moieties, ethyl moieties, propyl moieties, isopropyl moieties, and mixtures thereof. Preferably, the branches include methyl moieties, ethyl moieties, and mixtures thereof. More preferably, the branches include methyl moieties.

The at least two near terminal-branched compounds include one branch, two branches, or three branches. In embodiments when $R^2$ has three branches, $R^1$ is hydrogen. In some embodiments, the at least two compounds have two or three branches and two of these branches are at the omega-1 position. In other embodiments, the at least two compounds have two or three branches and none of the branches are geminal. In preferred embodiments, the at least two near terminal-branched compounds each have one branch.

The mixtures in this embodiment of the invention can include 10 wt %, about 20 wt %, about 30 wt %, about 40 wt %, about 50 wt %, about 60 wt %, about 70 wt %, about 80 wt % and about 90 wt % of iso compounds, based on the total weight of near terminal-branched compounds, as previously described herein. In some preferred embodiments, the mixture of the invention includes less than 50 wt % of the iso compound. In some embodiments, the near terminal-branched compounds include only anteiso compounds.

The compositions containing the mixtures of the at least two compounds are substantially free of secondary hydroxy compounds (i.e., hydroxy fatty acids/alcohols and iso-hydroxy fatty acids/alcohols), as previously described herein.

The compositions containing the mixtures of the at least two compounds optionally include a linear compound, a mid-chain branched compound, or mixtures thereof in an amount of no more than about 50 wt %, preferably no more than 10 wt %, for example, no more than about 2 wt %, based on the total weight of the composition, as previously described.

It is further understood that the above compounds can be partially hydrogenated by known methods to give new mixtures which are also part of the invention, as previously described herein.

Methods for Preparing the Mixtures Herein

The mixtures herein can be prepared using any of a variety of chemical or biological methods.

Grignard chemistry can be used to prepare the branched compounds of the invention. For example, the synthesis of the branched compound, 10-methyldodecyl acetate using Grignard chemistry is described by Suguro et al., in Agric, Biol. Chem., 43 (4), 869-860, 1979. The mixtures of the invention can be prepared using Grignard chemistry, as shown in Scheme 1.

10 to 30 carbon atoms in their longest chain, and contain 1 to 3 branches within 40% of the nonfunctionalized terminus of the longest carbon chain.

In Scheme 1, benzyl alcohol is deprotonated before undergoing a mononucleophilc substitution reaction with a terminal dihalide. The length of the terminal dihalide can be varied, depending on the desired length of the near terminal-branched fatty alcohols in the mixture (e.g., $Br(CH_2)_8Br$, $Br(CH_2)_{10}Br$, $Br(CH_2)_{11}Br$, $Br(CH_2)_{12}Br$). The resulting intermediate is reacted with magnesium under anhydrous conditions to form a Grignard reagent. The Grignard reagent is reacted with an aldehyde that has near terminal branching, dehydrated under acidic conditions (e.g., with para-toluenesulfonic acid), and reduced using hydrogen and a hydrogenation catalyst (e.g., $H_2$, Pd/C) to form near terminal-branched fatty alcohols.

The near terminal-branched aldehyde used in Scheme 1 can be varied depending on the desired fatty alcohol product mixture. For example, use of 2-methylbutyraldehyde will result in fatty alcohols with anteiso branching, while use of isovaleraldehyde will result in fatty alcohols with iso branching.

Using Grignard chemistry, mixtures of different dihalides and/or different near terminal-branched aldehydes can be reacted together according to Scheme 1 to form the mixture of

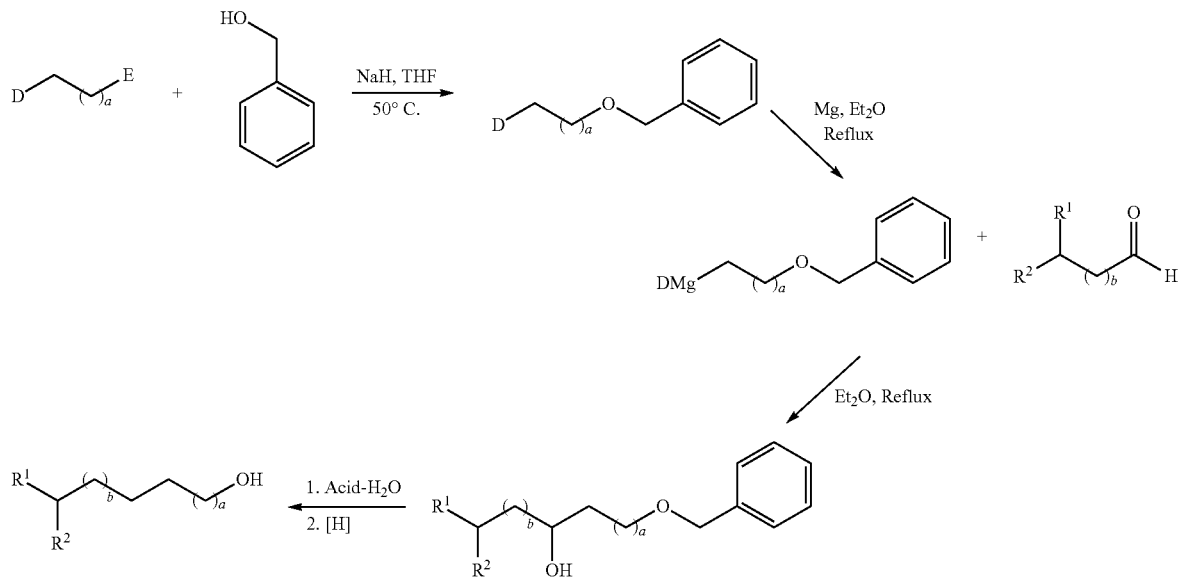

Scheme 1. Preparation of Near Terminal-Branched Fatty Alcohol Mixtures Using Grignard Chemistry wherein D and E are each independently Br or I;
$R^1$ is hydrogen, methyl, or ethyl;
$R^2$ is $(C_1-C_d)$alkyl or $(C_1-C_d)$alkenyl having 0, 1, 2, or 3 $(C_1-C_3)$alkyl branches,
a is 1 to 20;
b is 0 to 20; and
d is 1 to 4.

The starting materials are selected so that the near terminal-branched fatty alcohols products have 8 to 40, preferably fatty alcohol reaction products. Alternatively, a single dihalide and a single near terminal-branched aldehyde can be reacted together according to Scheme 1 to form a single near terminal-branched fatty alcohol. This near terminal-branched fatty alcohol can be combined with one or more different near terminal-branched fatty alcohols to form the mixture of fatty alcohol reaction products. An example of the synthesis of a 13 total-carbon anteiso fatty alcohol using Grignard chemistry is shown below.

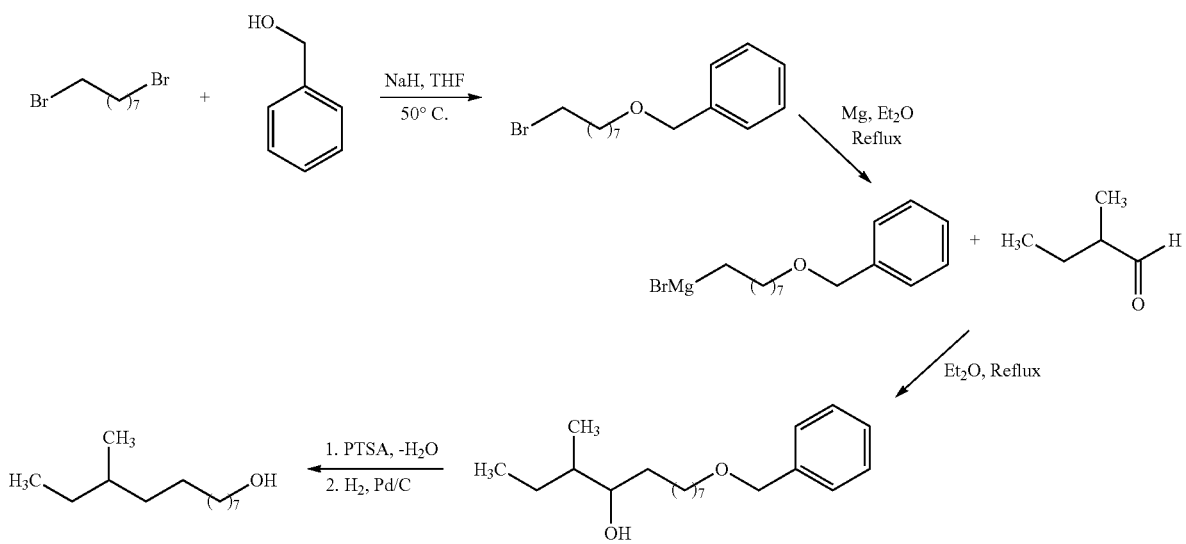

In another embodiment, the mixtures of the invention are prepared using Wittig chemistry, as shown in Scheme 2.

Scheme 2. Preparation of Near Terminal-Branched Fatty Alcohol Mixtures Using Grignard Chemistry a)
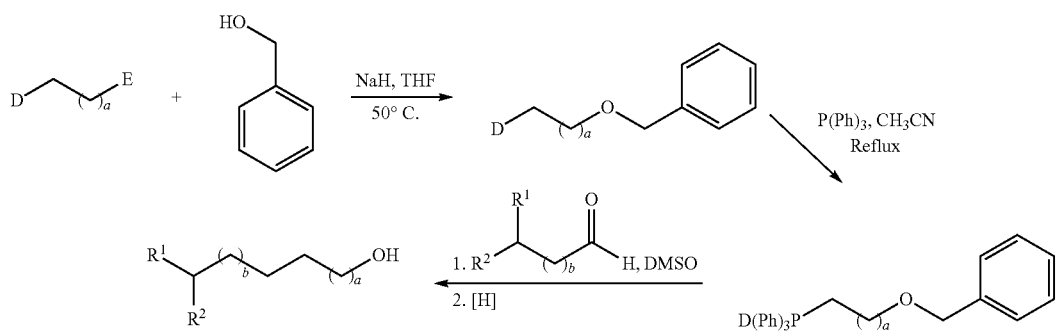

b)
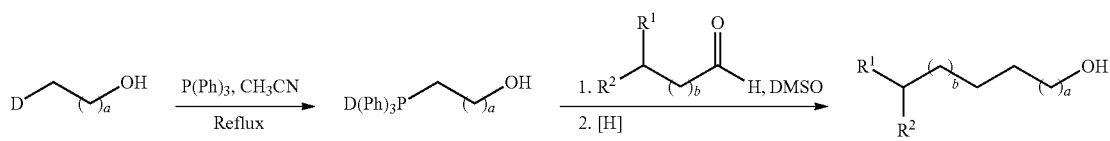

wherein D and E are each independently Br or I;
$R^1$ is hydrogen, methyl, or ethyl;
$R^2$ is $(C_1\text{-}C_d)$alkyl or $(C_1\text{-}C_d)$alkenyl having 0, 1, 2, or 3 $(C_1\text{-}C_3)$alkyl branches;
a is 1 to 20;
b is 0 to 20; and,
d is 1 to 4.

The starting materials are selected so that the near terminal-branched fatty alcohols products have 8 to 40, preferably 10 to 30 carbon atoms in their longest chain, and contain 1 to 3 branches within 40% of the nonfunctionalized terminus of the longest carbon chain.

The first step in Scheme 2a is as described in Scheme 1. The resulting intermediate is reacted with triphenylphosphine under reflux to form a Wittig reagent. The Wittig reagent is reacted with an aldehyde that has near terminal branching and reduced using hydrogen and a hydrogenation catalyst (e.g., $H_2$, Pd/C) to form near terminal-branched fatty alcohols.

In the first step of Scheme 2b, halide terminated alcohol is reacted with triphenylphosphine under reflux to form a Wittig reagent. The Wittig reagent is reacted with an aldehyde that has near terminal branching and reduced using hydrogen and a hydrogenation catalyst (e.g., $H_2$, Pd/C) to form near terminal-branched fatty alcohols.

The dihalide, halide terminated alcohol, and near terminal-branched aldehyde used in Scheme 2 can be varied depending on the desired fatty alcohol product mixture, as previously described.

Using Wittig chemistry, mixtures of different dihalides/halide terminated alcohols and/or different near terminal-branched aldehydes can be reacted together according to Scheme 2a or 2b to form the mixture of fatty alcohol reaction products. Alternatively, a single dihalide or dihalide terminated alcohol and a single near terminal-branched aldehyde can be reacted together according to Scheme 2a or 2b to form a single near terminal-branched fatty alcohol. This near terminal-branched fatty alcohol can be combined with one or more different near terminal-branched fatty alcohols to form the mixture of fatty alcohol reaction products. Examples of the synthesis of a 13 total carbon anteiso fatty alcohol using Wittig chemistry are shown below.

In the first step of Scheme 3, a halide terminated alcohol is reacted with a near terminal-branched Grignard reagent in the presence of a copper catalyst to form near terminal-branched fatty alcohols. The length of the halide terminated alcohol can be varied, depending on the desired length of the near terminal-branched fatty alcohols in the mixture (e.g., $Br(CH_2)_8OH$, $Br(CH_2)_{10}OH$, $Br(CH_2)_{11}OH$, $Br(CH_2)_{12}OH$). The near terminal-branched aldehyde used in Scheme 3 can be varied depending on the desired fatty alcohol product mixture.

Using copper-mediated chemistry, mixtures of different halide terminated alcohols and/or different near terminal-

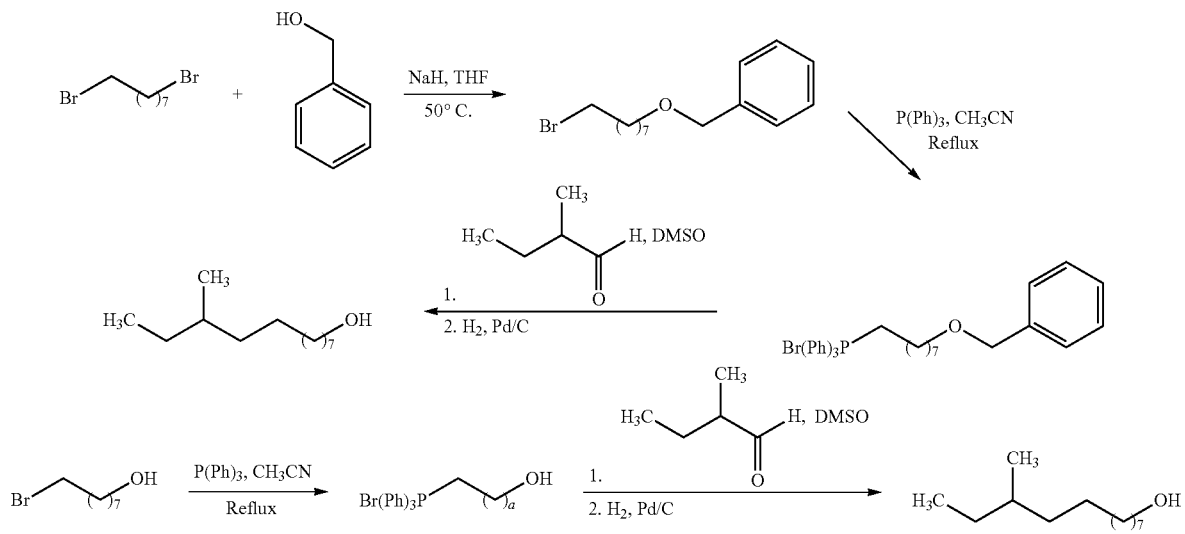

In another embodiment, the mixtures of the invention are prepared using copper-mediated coupling chemistry, as shown in Scheme 3.

Scheme 3. Preparation of Near Terminal-Branched Fatty Alcohol Mixtures Using Copper-Mediated Coupling Chemistry

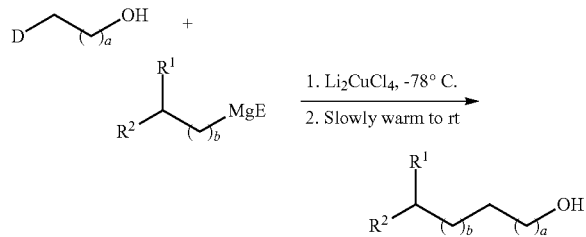

wherein D and E are each independently Br or I;
$R^1$ is hydrogen, methyl, or ethyl;
$R^2$ is $(C_1\text{-}C_d)$alkyl or $(C_1\text{-}C_d)$alkenyl having 0, 1, 2, or 3 $(C_1\text{-}C_3)$alkyl branches;
a is 1 to 20;
b is 0 to 20; and,
d is 1 to 4;

The starting materials are selected so that the near terminal-branched fatty alcohols products have 8 to 40, preferably 10 to 30 carbon atoms in their longest chain, and contain 1 to 3 branches within 40% of the nonfunctionalized terminus of the longest carbon chain.

branched Grignard reagents can be reacted together according to Scheme 3 to form the mixture of fatty alcohol reaction products. Alternatively, a single halide terminated alcohol and a single near terminal-branched Grignard reagent can be reacted together according to Scheme 3 to form a single near terminal-branched fatty alcohol. This near terminal-branched fatty alcohol can be combined with one or more different near terminal-branched fatty alcohols to form the mixture of fatty alcohol reaction products. An example of the synthesis of a 15 total-carbon anteiso fatty alcohol using copper-mediated coupling chemistry is shown below.

A cuprate coupling reaction is shown in Flavour Fragr. J. 2004; 19; 199-204, which is. However, initial attempts using this procedure led to poor yields. Improvements to the process gave high and reproducible yields, as noted in the previous scheme. Such changes include (i) maintaining the temperature below −65° C., preferably −78° C. upon addition of the $Li_2CuCl_4$ to the Grignard reagents, (ii) addition of the bromoalcohol at −65° C., (iii) slow warming to room temperature over 4-6 hours; (iv) stirring overnight for yields in excess of 98% at any scale from 5 g to 70 g reproducibly.

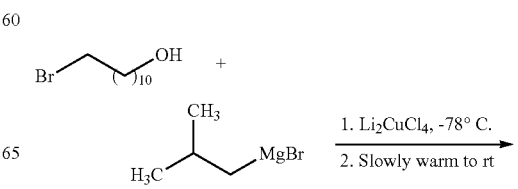

-continued

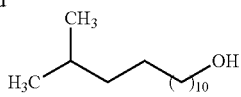

In another embodiment, the mixtures of the invention are prepared using palladium-catalyzed coupling chemistry, as shown in Scheme 4.

Scheme 4. Preparation of Near Terminal-Branched Fatty Alcohol Mixtures Using Palladium-Catalyzed Coupling Chemistry

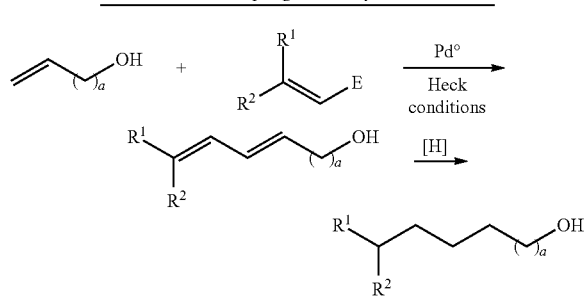

wherein E is Br or I;

$R^1$ is hydrogen, methyl, or ethyl;

$R^2$ is $(C_1\text{-}C_d)$alkyl or $(C_1\text{-}C_d)$alkenyl having 0, 1, 2, or 3 $(C_1\text{-}C_3)$alkyl branches;

a is 1 to 29;

d is 1 to 4;

The starting materials are selected so that the near terminal-branched fatty alcohols products have 8 to 40, preferably 10 to 30 carbon atoms in their longest chain, and contain 1 to 3 branches within 40% of the nonfunctionalized terminus of the longest carbon chain.

The first step of Scheme 4 involves coupling a near terminal-branched vinyl halide and a terminal alkenol in the presence of an organopalladium catalyst (e.g., tetrakis(triphenylphosphine)palladium(0), palladium chloride, palladium (II) acetate), under Heck conditions (e.g., base such as triethylamine, potassium carbonate or sodium acetate) to form a diene. The diene is reduced using hydrogen and a hydrogenation catalyst (e.g., $H_2$, Pd/C) to form near terminal-branched fatty alcohols.

The length of the alkenol can be varied, depending on the desired length of the near terminal-branched fatty alcohols in the mixture (e.g., a=7, 8, 9, 10, 11, 12, 13). The near terminal-branched vinyl halide used in Scheme 4 can also be varied depending on the desired fatty alcohol product mixture.

Using palladium catalyzed-chemistry, mixtures of different alkenol and/or different near terminal-branched vinyl halides can be reacted together according to Scheme 4 to form the mixture of fatty alcohol reaction products. Alternatively, a single alkenol and a single near terminal-branched vinyl halide can be reacted together according to Scheme 4 to form a single near terminal-branched fatty alcohol. This near terminal-branched fatty alcohol can be combined with one or more different near terminal-branched fatty alcohols to form mixture of fatty alcohol reaction products. An example of the synthesis of a 14 total-carbon iso fatty alcohol using copper-mediated coupling chemistry is shown below.

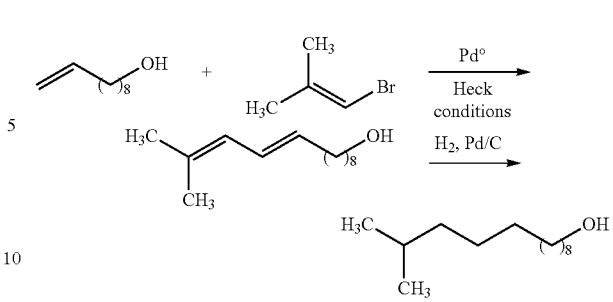

The above procedures can be used to prepare the alcohols of the invention. These alcohols can be further be modified by conventional processes such as sulfation with chlorosulfonic acid, ethoxylation with ethylene oxide or sulfonated, aminated, aminated and oxidized to provide materials for blending, evaluation of properties, analytical documentation of compositions, etc.

The mixtures of near terminal-branched fatty alcohols and/or fatty acids can also be prepared using metabolically engineered organisms. The preparation of fatty alcohols, fatty aldehydes, fatty acids, and derivatives thereof from genetically-modified cells and microrganisms for use in applications such as biofuels, polymers, surfactants, lubricating oil additives, and intermediates for the production of derivatives such as acrylates used in paints, coatings, and adhesive applications, is described in U.S. Patent Application Publication Nos. 2010/0105955 and 2010/0105963; and International Patent Application Publication Nos. WO 2007/136752, WO 2008/119082, and WO 2009/111672, which are incorporated by reference.

U.S. Provisional Application No. 61/289,039 ("the '039 application," assigned to The Procter & Gamble Company), which is incorporated by reference, describes methods for the biological production of anteiso and iso fatty acids, and methods for improving the biological production of such anteiso and/or iso fatty acids. Specifically, the '039 application describes a method of producing anteiso and/or iso branched-chain fatty acids using bacteria. In general, the method features incorporating a polynucleotide encoding a branched-chain α-keto acid dehydrogenase, or a biologically active fragment or variant thereof, into a suitable cell, such as, for example, by transfecting or transforming the cell with such a polynucleotide. The method can include incorporating a polynucleotide encoding a 3-ketyoacyl-ACP synthase that uses anteiso and/or iso branched-CoA primers as substrates into a suitable cell. In addition, the method can include incorporating a polynucleotide encoding a thioesterase into a suitable cell. Depending on the activity and substrate specificity of the thioesterase, such recombinant cells can produce anteiso and/or iso branched-chain fatty acids having a desired chain length. Any suitable vectors, expression constructs, strains, and cell lines can be used to construct cells having exogenous BCDH, FabH, and/or thioesterase polynucleotides encoding an exogenous branched-chain α-keto acid dehydrogenase, 3-ketoacylACP synthase, and/or thioesterase, respectively. The '039 application also describes methods of engineering cells to produce anteiso and/or iso branched-chain fatty acids, and methods of modifying cells or organisms that naturally produce anteiso and/or iso branched chain fatty acids to produce higher levels of anteiso and/or iso branched chain fatty acids compared to an unmodified cell or organism.

Bioproducts comprising biologically produced organic compounds, particularly those produced using the fatty acid biosynthetic pathway, have not been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588, which is herein incorporated by reference).

The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the instant materials may be followed in commerce on the basis of their unique carbon isotope profile.

Bioproducts can be distinguished from petroleum based organic compounds by comparing the stable carbon isotope ratio ($^{13}C/^{12}C$) in each fuel. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway.

Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the "$C_3$" (or Calvin-Benson) photosynthetic cycle and those that incorporate the "$C_4$" (or Hatch-Slack) photosynthetic cycle.

In $C_3$ plants, the primary $CO_2$ fixation or carboxylation reaction involves the enzyme ribulose-1,5-diphosphate carboxylase, and the first stable product is a 3-carbon compound. $C_3$ plants, such as hardwoods and conifers, are dominant in the temperate climate zones.

In $C_4$ plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the $C_3$ cycle. Examples of $C_4$ plants are tropical grasses, corn, and sugar cane.

Both $C_4$ and $C_3$ plants exhibit a range of $^{13}C/^{12}C$ isotopic ratios, but typical values are about −7 to about −13 per mil for $C_4$ plants and about −19 to about −27 per mil for $C_3$ plants (see, e.g., Stuiver et al., *Radiocarbon*, 19: 355 (1977)). Coal and petroleum fall generally in this latter range. The $^{13}C$ measurement scale was originally defined by a zero set by Pee Dee Belemnite (PDB) limestone, where values are given in parts per thousand deviations from this material. The "$\delta^{13}C$" values are expressed in parts per thousand (per mil), abbreviated, ‰, and are calculated as follows:

$$\delta^{13}C(‰)=[(^{13}C/^{12}C)_{sample}-(^{13}C/^{12}C)_{standard}]/(^{13}C/^{12}C)_{standard}\times 1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46.

The compositions described herein include bioproducts produced by any of the methods described herein. Specifically, the bioproduct can have a $\delta^{13}C$ of about −28 or greater, about −27 or greater, −20 or greater, −18 or greater, −15.4 or greater, −15 or greater, −13 or greater, −10 or greater, or −8 or greater. For example, the bioproduct can have a $\delta^{13}C$ of about −30 to about −15, about −27 to about −19, about −25 to about −21, about −15 to about −5, about −15.4 to about −10.9, about −13.92 to about −13.84, about −13 to about −7, or about −13 to about −10. In other instances, the bioproduct can have a $\delta^{13}C$ of about −10, −11, −12, or −12.3.

Bioproducts can also be distinguished from petroleum based organic compounds by comparing the amount of $^{14}C$ in each compound. Because $^{14}C$ has a nuclear half life of 5730 years, petroleum based fuels containing "older" carbon can be distinguished from bioproducts which contain "newer" carbon (see, e.g., Currie, "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc.) (1992), pp. 3-74).

The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about $1.2\times10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.)

It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

The invention provides a bioproduct which can have an $f_M$ $^{14}C$ of at least about 1. For example, the bioproduct can have an $f_M$ $^{14}C$ of at least about 1.01, of at least about 1.5, an $f_M$ $^{14}C$ of about 1 to about 1.5, an $f_M$ $^{14}C$ of about 1.04 to about 1.18, or an $f_M$ $^{14}C$ of about 1.111 to about 1.124.

Another measurement of $^{14}C$ is known as the percent of modern carbon, pMC. For an archaeologist or geologist using $^{14}C$ dates, AD 1950 equals "zero years old". This also represents 100 pMC. "Bomb carbon" in the atmosphere reached almost twice the normal level in 1963 at the peak of thermonuclear weapons testing. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC.

A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material.

A bioproduct described herein can have a pMC of at least about 50, 60, 70, 75, 80, 85, 90, 95, 96, 97, 98, 99, or 100. In other instances, a bioproduct described herein can have a pMC of between about 50 and about 100; between about 60 and about 100; between about 70 and about 100; between about 80 and about 100; between about 85 and about 100; between about 87 and about 98; or between about 90 and about 95. In yet other instances, a bioproduct described herein can have a pMC of about 90, 91, 92, 93, 94, or 94.2.

Another method for the controlled preparation of near terminal-branched fatty acids, alcohols, and mixtures thereof is via the use of metathesis chemistry. Metathesis involves reaction of one olefin with another in the presence of a metathesis catalyst to form a new olefin mixture with complete conservation of carbons as illustrated:

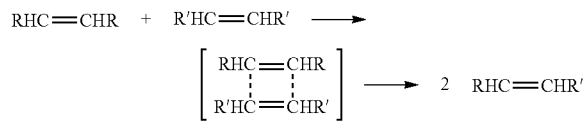

Metathesis chemistry is well known to one skilled in the art (see Kirk, "Ruthenium Based Homogeneous Olefin Metathesis," M.S. Dissertation, University of the Free State, South Africa, 2005). For example, U.S. Pat. No. 4,545,941 and U.S. Patent Application Publication No., 2010/0160506, which are incorporated herein by reference, disclose the metathesis of unsaturated triglycerides and alkenes, in the presence of a catalytically effective amount of a metathesis catalyst, to produce modified triglycerides and alpha-olefins. PCT Patent Application No. WO 2008/046106, incorporated herein by reference, discloses the metathesis of terminal alkenes and fats and oils (e.g., soybean oil, sunflower oil, canola oil, safflower oil, cottonseed oil, castor oil, rapeseed oil, peanut oil, corn oil, olive oil, palm oil, sesame oil, grape seed oil) to form linear metathesis products using a ruthenium alkylidene catalyst.

Descriptions of alkene metatheses using branched olefin starting materials and a tungsten catalyst can be found in U.S. Patent Application Publication No. 2008/0255328, and U.S. Pat. No. 7,635,794, which are. PCT Application Publication No. WO 2001/046096 and U.S. Patent Application Publication No. 2003/0135080, incorporated herein by reference, disclose a method for converting short chain olefins (e.g., $C_4$-$C_{10}$ olefins) from Fischer-Tropsch derived feedstock to longer chain olefins (e.g., $C_6$-$C_{18}$) using a heterogeneous metal-alkyliene catalyst such as tungsten, ruthenium (e.g., Grubb's catalyst), osmium, and iridium. Marvy et al., "Ruthenium Carbene Mediated Meathesis of Oleate-Type Fatty Compounds," Int. J. Mol. Sci. 9, 615-625 (2008) discloses the self- and cross-methathesis of olefinic fatty acids and esters using Grubb's catalysts, $RuCl_2(PCy_3)_2$(=CHPh) and $RuCl_2(PCy_3)(H_2IMes)$(=CHPh). U.S. Pat. Nos. 5,942,653 and 4,943,397, incorporated herein by reference, also disclose methods of olefin metathesis. Buchmeiser, "Polymer-Supported Well-Defined Metathesis Catalysts," Chem. Rev., 109, 303-321, 2009, provides a general description of metathesis using polymer-bound catalysts.

The metathesis route of the invention is advantageous because it can use a variety of inexpensive feedstock including fats; oils; unsaturated fatty alcohols, acids, and esters; coupled with low cost branched olefins feedstocks such as: cracker feed by prefractionation; olefin products from Fischer Tropsch processing of biomass; feedstock from ethylene oligomerization; plant matter, and dimerization products from the DIMSEROL® process, existing gas to liquids feedstocks such as from Sasol South Africa, Shell Bintulu, Qatar and others. Other sources of starting materials for the metathesis route include branched olefins from cellulosic biomass. For example, isobutanol can be produced from sources of glucose using the GIFT™ process by Gevo, which can be dehydrated to form isobutylene and subsequently dimerized into isooctane for use in the present invention. Future feedstocks of use to the current invention are bioethylene, biopropylene, biobutylene all of which can be oligomerized and or isomerized to provide biobranched olefins for use in the present invention. In some embodiments, it is preferred to provide bio-based olefin feedstocks for the metathesis reaction with fats and oils. In other embodiments, any conventional petroleum based branched olefin feedstock or mixtures containing such feedstocks are viable for conversion using the said process.

Further, the feedstock can include crude commercial starting materials that contain, for example, paraffin, isoparaffin, and aromatic contaminants because these contaminants are unreactive during the metathesis process, yet can easily be distilled from the product. Further still, the metathesis route has a simple reaction design with a minimum number of reaction steps. For example, current approaches to synthesize the branched alcohols NEODOL 67® and ISALCHEM® require multiple extensive chemical steps, sometimes with multiple catalysts, separations, and other processing steps. Importantly, the by-products produced by the metathesis route are commercially useful, for example, as biofuels. Even further, the metathesis route can be performed using only biodegradable feedstock.

The great variety of feedstock allows for tunability of resulting compositions containing mixtures of near terminal-branched fatty acids, alcohols, and mixtures thereof. Significantly, this wide variety of feedstock allows the production of unique mixtures that were previously unobtainable at low cost or even at all. For example, the metathesis route allows for the first time the production of mixtures containing near terminal-branched compounds that do not include iso and/or linear compounds.

The metathesis route also allows for the controlled production of mixtures containing specific near terminal branched compounds in specific ratios. Unlike some metathesis processes known in the art, the metathesis route of the invention allows for the purposeful (instead of random) introduction of $(C_1-C_3)$alkyl branches at specific locations within the compounds of the invention. For example, mixtures containing near terminal-branched compounds with 12 and 15 carbon atoms; 12, 13, and 14 carbon atoms; or 13, 15 and 17 carbon atoms can now be obtained in high concentrations and without excessive cost, if desired. Further still, the metathesis route can provide mixtures with multiple functions. For example, the metathesis route can be used to prepare mixtures composed of near terminal-branched fatty acids or alcohols with 12 and 18 carbon atoms, which are useful for both surfactant performance and fabric softening.

Further, the products of the metathesis route can be processed (e.g., derivatized) without first being isolated or purified. The ability to process the crude reaction product of the metathesis route results in significant time, energy, and cost savings.

In the metathesis method for the production of compositions containing mixtures of near terminal-branched fatty acids and alcohols, an alkene of Formula II:

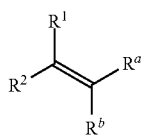

II is reacted with a compound selected from the group consisting of:

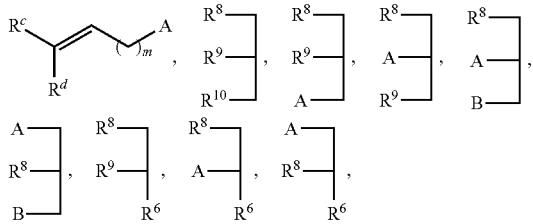

and mixtures thereof; and, a metathesis catalyst in a catalytically effect amount, to form a composition comprising:

(i) a mixture of at least two compounds selected from the group consisting of:

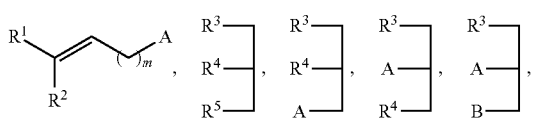

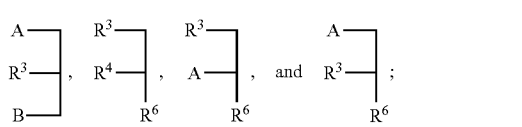

and, (ii) a side product selected from the group consisting of

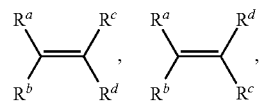

and mixtures thereof;

wherein A and B are each independently OH or (C=O)OR$^7$;

R$^1$ is hydrogen, methyl, or ethyl;

R$^2$ is $(C_1-C_n)$alkyl or $(C_1-C_n)$alkenyl having 0, 1, 2, or 3 $(C_1-C_3)$alkyl branches, wherein branching occurs on carbon atoms that are within 40% of the nonfunctionalized terminus of the longest carbon chain; of the at least two compounds;

R$^3$, R$^4$, and R$^5$ are each independently

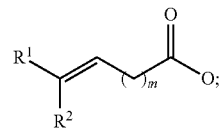

R$^6$ is hydrogen, methyl, or ethyl;

R$^7$ is $(C_1-C_{26})$alkyl;

wherein R$^8$, R$^9$, and R$^{10}$ are each independently

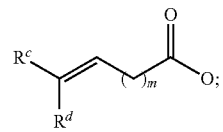

R$^a$ and R$^b$ are each independently hydrogen or $(C_1-C_{22})$alkyl;

R$^c$ and R$^d$ are each independently hydrogen, $(C_1-C_{22})$alkyl, or $(C_1-C_{22})$alkenyl; and, m is 5-37 and n is 1-33, wherein m+n is 6-38; preferably m is 7-27 and n is 1-23, wherein m+n is 8-28; for example, when m is 7 and n is 9, or m is 11 and n is 17;

wherein with respect to at least one of the compounds, when R$^1$ is H, then R$^2$ has 1, 2, or 3 $(C_1-C_3)$ alkyl branches, and when R$^1$ is methyl or ethyl, then R$^2$ has 0, 1, or 2 $(C_1-C_3)$alkyl branches. In one embodiment, with respect to the at least two compounds, when R$^1$ is H, then R$^2$ has 1, 2, or 3 $(C_1-C_3)$ alkyl branches, and when R$^1$ is methyl or ethyl, then R$^2$ has 0, 1, or 2 $(C_1-C_3)$alkyl branches.

The alkene of Formula II can be any alkene that contains near terminal-branching, as defined herein. R$^a$ and R$^b$ can each be any substituent that does not interfere with the metathesis reaction. For example, R$^a$ and R$^b$ are each independently hydrogen or $(C_1-C_{22})$alkyl.

R$^2$ is an alkyl or alkenyl moiety that is 1 to 33, preferably 1-23 carbon atoms in length, and has 0, 1, 2, or 3 branches selected from the group consisting of methyl, ethyl, propyl, isopropyl, and mixtures thereof. If R$^2$ has no branches, then R$^1$ is methyl or ethyl. If R$^2$ has 3 branches, then R$^1$ is hydrogen. R$^2$ preferably contains methyl and ethyl branches, more preferably methyl branches. In some embodiments when R$^2$ has 5 or less carbon atoms in its longest chain, R$^1$ can be hydrogen, methyl, or ethyl. In other embodiments when R$^2$ has 6 or more carbon atoms in its longest chain, $R^1$ is hydrogen. Preferably, the alkene of Formula II contains branching on its terminal carbon atom or on 1 carbon away from its terminal carbon atom. In some embodiments, the alkene of Formula II has geminal branching on its terminal carbon. In other embodiments, the alkene of Formula II has two or three branches and none of the branches are geminal.

The alkene of Formula II can be used as part of a crude mixture also containing, for example, paraffin, isoparffin, and aromatic contaminants. Further, the alkene of the invention can be obtained from a variety of different feedstocks such cracker feed by prefractionation; olefin containing products from gasification of biomass, municipal waste, coal, coke followed by Iron catalyzed Fischer Tropsch processing (other catalysts can be used for Fischer Tropsch reaction however iron provides the highest olefin content); feedstock from ethylene oligomerization; and dimerization products from the DIMSEROL® process; various cuts of crude petroleum distillates and potentially even crude oil of various types can be used if so desired.

Nonlimiting examples of singly and multiply branched alkenes of Formula II include (note the unreacted contaminants are not shown in this table only the olefins in the mixtures which can react to provide the product of the invention). Also although terminal olefins are preferred it is understood that internal olefins can also lead to metathesis and produce the products of the invention. It is also understood by one skilled in the art of metathesis that some of these internal olefins can form from the terminal olefins during metathesis and can still undergo metathesis with the ester, fats or oils resulting in the products of the invention:

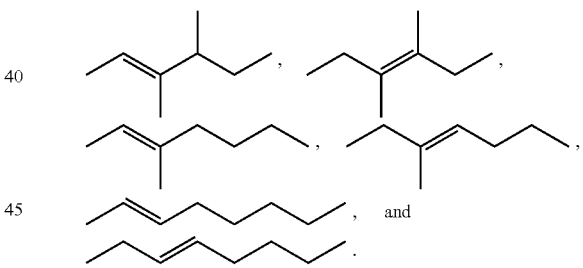

Examples of alkenes of Formula II that are produced using the DIMERSOL® process include:

Examples of alkenes of Formula II that are produced using the Fischer-Tropsch process are described in PCT Application Publication No. WO 2001/046096 and U.S. Patent Application Publication No. 2003/0135080.

Isooctene, produced by the GIFT™ process by Gevo, can also be used as the alkene of Formula II.

The alkene of Formula II is added to an unsaturated alcohol or ester in the presence of a metathesis catalyst. For example, the alkene of Formula II can be added to an unsaturated fatty alcohol, an unsaturated fatty ester, an unsaturated monoglyceride, a triglyceride or diglyceride that has at least one unsaturated fatty ester group, an ethylene glycol that is substituted with at least one unsaturated fatty ester group, and mixtures thereof. In some embodiments, the alkene of Formula II is added to a compound or composition that includes oleic acid (shown below), linoleic acid (shown below), linolenic acid, eurcic acid (shown below), or mixtures thereof either as free acid or ester or as various glyceride types. Other types of oils that an alkene can be added to include soybean, rapeseed, canola, palm, palm kernel, coconut, jatropha, high erucic rapeseed, cottonseed, tallow, yellow grease, corn, sunflower, babasu, and mixtures thereof.

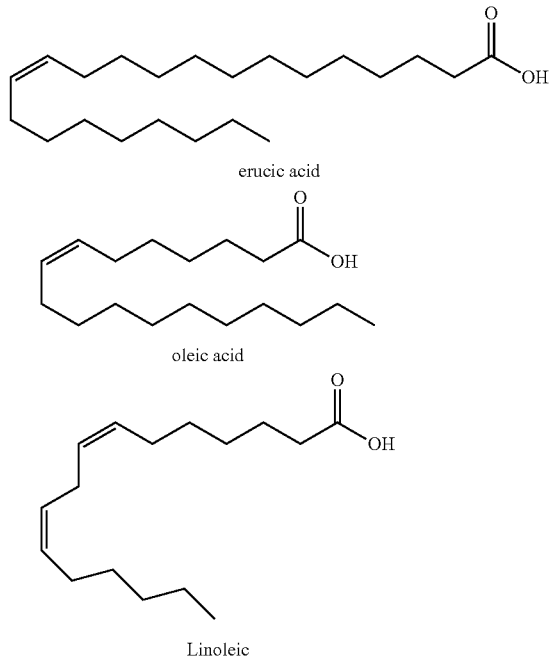

erucic acid oleic acid

Linoleic

In some embodiments, the alkene of Formula II is added to one or more of the following compounds:

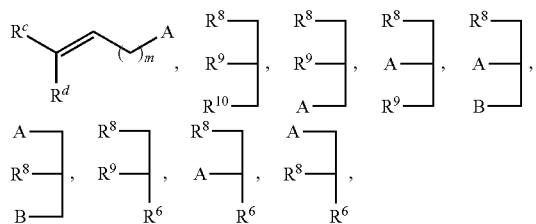

wherein A and B are each independently alcohol moieties or ester moieties, and $R^8$, $R^9$, and $R^{10}$ are each independently

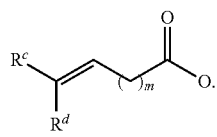

$R^c$ and $R^d$ can each be any substituent that does not interfere with the metathesis reaction. For example, $R^c$ and $R^d$ are each independently hydrogen, $(C_1-C_{22})$alkyl, or $(C_1-C_{22})$alkenyl.

The metathesis catalyst includes any catalyst or catalyst system that catalyzes the metathesis reaction of the invention. Examples of metathesis catalysts are described in the metathesis references previously described herein. For example, the metathesis catalysts include a tungsten compound and an aluminum oxide compound, as described in U.S. Pat. No. 7,635,794, which is. The metathesis catalyst can also include a heterogeneous metal-alkyliene catalyst, such as tungsten, ruthenium (e.g., Grubb's catalyst), osmium, and iridium, as described in PCT Application Publication No. WO 2001/046096 and U.S. Patent Application Publication No. 2003/0135080. The metathesis catalyst can also include a Grubb's catalyst as described in Marvy et al., "Ruthenium Carbene Mediated Meathesis of Oleate-Type Fatty Compounds," Int. J. Mol. Sci. 9, 615-625 (2008), or a polymer-bound catalyst as described in Buchmeiser, "Polymer-Supported Well-Defined Metathesis Catalysts," Chem. Rev., 109, 303-321, 2009.

The metathesis reaction is generally catalyzed by a system containing both a transition and a non-transition metal component. The most active and largest number of catalyst systems are derived from the Group VIA transition metals, tungsten and molybdenum. Organoaluminum compounds, and alkyl derivatives of tin, lithium, and magnesium are the most widely used non-transition metal component of the metathesis catalyst system. In some embodiments, the metathesis catalysts include a tungsten compound and a tin compound. Suitable tungsten compounds include tungsten oxychloride, tungsten pentabromide, tungsten dichloride, tungsten tetrachloride, and tungsten hexachloride. Suitable tin compounds include the alkyl derivatives such as tetramethyl tin and tetra-n-butyl tin. For example, the metathesis catalyst can comprise tungsten hexachloride and tetramethyl tin. In some embodiments, the two catalyst components are present in equimolar amounts.

The metathesis reaction can be carried out neat or in an organic solvent. The presence of a solvent improves mixing and, if added to the unsaturated fatty alcohol and/or unsaturated fatty acid and partially distilled off before reaction, helps remove traces of water which can poison such metathesis catalysts as tungsten hexachloride. The more commonly used solvents in metathesis reactions include such aliphatic solvents as the saturated hydrocarbons and such aromatic solvents as benzene, chlorobenzene, and toluene. The aliphatic solvents are preferred over the aromatics because of a reduced tendency to interact with the reactants. On the basis of maximizing the yield of metathesis products based on a given volume of solvent, the preferred solvents are saturated hydrocarbons boiling in the range of about 50° C. to about 120° C., such as commercial hexane.

The metathesis reaction of the invention is generally carried out temperature of about 35° C. to about 260° C., preferably about 50° C. to about 120° C. The reaction does not proceed to a noticeable degree at temperatures below about 35° C. The rate of the reactions increases with increasing temperature, but temperatures above about 260° C. are undesirable because the starting materials begin to degrade.

The product of the metathesis reaction depends on the specific starting materials used. Generally, the metathesis reaction will result in a mixture of unsaturated fatty alcohols and unsaturated fatty esters. In some embodiments, the metathesis reaction results in one or more of the following compounds: an unsaturated fatty alcohol, an unsaturated fatty ester, an unsaturated monoglyceride, a triglyceride or diglyceride that has at least one unsaturated fatty ester group, an ethylene glycol that is substituted with at least one unsaturated fatty ester group, and mixtures thereof. For example, the metathesis reaction can result in a mixture that has at least two of the following compounds:

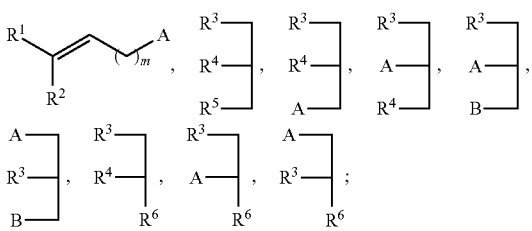

wherein A and B are each independently OH an ester; $R^1$ and $R^2$ are as defined above, $R^3$, $R^4$, and $R^5$ are each independently

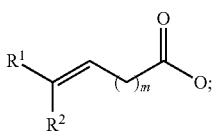

$R^6$ is hydrogen, methyl, or ethyl;
$R^7$ is $(C_1$-$C_{26})$alkyl; and,
m is 5-37 and n is 1-33, wherein m+n is 6-38; preferably m is 7-27 and n is 1-23, wherein m+n is 8-28; for example, when m is 7 and n is 9, or m is 11 and n is 17.

In some embodiments, at least one of

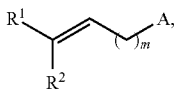

$R^3$, $R^4$, or $R^5$ contain one or more sites of unsaturation within the region of the molecule represented by $-(CH_2)_m-$, as previously described herein.

The by-product of the metathesis reaction is

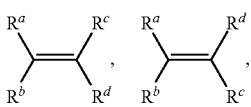

and mixtures thereof; wherein $R^a$, $R^b$, $R^c$, and $R^d$ are as defined above. After hydrogenation of such olefins, a high value use is a biojet fuel or a biodiesel fuel blend, as shown in FIG. 1, wherein TG stands for "triglyceride" and "NT" stands for "near terminal":

The at least two compounds of the product mixture have different chemical structures and are present in an amount of at least about 50 wt %, preferably at least about 75 wt %, more preferably at least about 90 wt %, for example, about 95 wt %, up to and including 100 wt %, based on the total weight of the composition.

The at least two compounds of the product mixture can have a length of about 8 to about 40 carbon atoms, preferably about 10 carbon atoms to about 30 carbon atoms, as previously described herein.

The at least two compounds of the product mixture can have branching within 40% of the nonfunctionalized terminus of the longest carbon chain, as previously described herein. In preferred embodiments, the at least two compounds of the product mixture comprise iso branching, anteiso branching, or iso and anteiso branching. In some embodiments when $R^2$ has 5 or less carbon atoms in its longest chain, $R^1$ can be hydrogen, methyl, or ethyl. In other embodiments when $R^2$ has 6 or more carbon atoms in its longest chain, $R^1$ is hydrogen.

The near terminal-branching on the at least two compounds of the product mixture is composed of $(C_1$-$C_3)$alkyl moieties. For example, the branches can include methyl moieties, ethyl moieties, propyl moieties, isopropyl moieties, and mixtures thereof. Preferably, the branches include methyl moieties, ethyl moieties, and mixtures thereof. More preferably, the branches include methyl moieties.

The at least two near terminal-branched compounds of the product mixture can have up to three branches. For example, the at least two compounds can include one branch, two branches, or three branches. In preferred embodiments, the at least two compounds each have one branch. In some embodiments, the at least two compounds have two or three branches and two of these branches are at the omega-1 position. In other embodiments, the at least two compounds have two or three branches and none of the branches are geminal.

The at least two near terminal-branched compounds of the product mixture can include from 0 wt % to about 100 wt % of iso compounds based on the total weight of near terminal-branched compounds. In some embodiments, the mixtures of the invention include about 1 wt % to about 40 wt % of iso compounds, based on the total weight of near terminal-branched compounds. In other embodiments, the mixtures of the invention include about 10 wt % to about 30 wt % of iso compounds, based on the total weight of near terminal-branched compounds. In some embodiments, the near terminal-branched compounds include only anteiso compounds.

The product compositions of the at least two compounds are substantially free of secondary hydroxy compounds. For example, the compositions of the invention contain no more than about 2 wt % of secondary hydroxy compounds, preferably no more than about 1 wt % of secondary hydroxy compounds, even more preferably 0 wt % of secondary hydroxy compounds, based on the total weight of the composition.

The compositions containing the mixtures of the at least two compounds optionally include one or more linear compounds, one or more mid-chain branched compounds, or mixtures thereof in an amount of no more than about 50 wt %, preferably no more than 10 wt %, for example, no more than about 2 wt %, based on the total weight of the composition. The specific amount of linear compounds and/or mid-chain branched compounds depends on the desired application, as previously described.

In some optional embodiments, the alkene starting materials are partially isomerized before the metathesis reaction, as described in PCT Patent Application Publication No. WO 2000/014038 and U.S. Pat. No. 6,777,582.

In some optional embodiments, the mixture of near terminal-branched products are isolated from the by-products using any method known in the art, such as fractional distillation.

In some optional embodiments, the mixture of near terminal-branched products are subjected to transesterification to release unsaturated fatty esters from the glycerol or ethylene glycol backbones to form unsaturated fatty acids.

The method of the invention further includes reducing the unsaturated fatty alcohols, unsaturated fatty esters, and unsaturated fatty acids using hydrogen and a hydrogenation catalyst to form compositions comprising mixtures containing at least two compounds of Formula III.

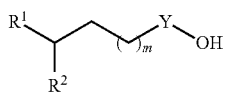

wherein $R^1$ is hydrogen, methyl, or ethyl;

$R^2$ is $(C_1\text{-}C_n)$alkyl or $(C_1\text{-}C_n)$alkenyl having 0, 1, 2, or 3 $(C_1\text{-}C_3)$alkyl branches, wherein branching occurs on carbon atoms that are within 40% of the nonfunctionalized terminus of the longest carbon chain, and m is 7 and n is 9, or m is 11 and n is 17; and, Y is C=O or $CH_2$;

wherein with respect to at least one of the compounds, when $R^1$ is H, then $R^2$ has 1, 2, or 3 $(C_1\text{-}C_3)$ alkyl branches, and when $R^1$ is methyl or ethyl, then $R^2$ has 0, 1, or 2 $(C_1\text{-}C_3)$ alkyl branches. In one embodiment, with respect to the at least two compounds, when $R^1$ is H, then $R^2$ has 1, 2, or 3 $(C_1\text{-}C_3)$ alkyl branches, and when $R^1$ is methyl or ethyl, then $R^2$ has 0, 1, or 2 $(C_1\text{-}C_3)$alkyl branches.

Reduction is carried out with a variety of catalysts such as copper chromite, nickel on Kieselguhr, rhodium on silica, and palladium on Kieselguhr. Reaction conditions vary from 20° C. to about 130° C., a hydrogen pressure ranging from 100 psig to about 2000 psig of hydrogen and catalyst loadings can typically be in range of about 1 wt % to about 5 wt % on the substrate. Reaction times will vary according to catalyst ratio, temperature chosen and hydrogen pressure. Typical conditions are 150° C. at 1000 psig for 16 hours in batch mode. The process is not limited to batch processes. Continuous reaction can also be applied to the present invention.

During the reduction step, the reaction by-products, if present, are reduced to paraffins and isoparaffin, which can easily be removed from the compositions of the invention using fractional distillation. These reduced by-products are useful in biodiesel applications. The metathesis route used to form the compositions of the invention is both energy efficient and green since the by-products are also useful.

The metathesis route can be used in different ways to form mixtures containing near terminal-branched fatty acids and alcohols. In some embodiments, mixtures of different alkenes of Formula II and mixtures of different unsaturated fatty ester and/or unsaturated fatty alcohol starting materials are reacted together along with a metathesis catalyst to form the mixture of fatty alcohol and fatty acid reaction products. Alternatively, a single alkene of Formula II and a single unsaturated fatty ester and/or unsaturated fatty alcohol starting material can be reacted together in the presence of a metathesis catalyst to form a single near terminal-branched fatty acid or alcohol. This near terminal-branched fatty acid or alcohol can be combined with one or more different near terminal-branched fatty acids alcohols to form the mixture of fatty alcohol/acid reaction products.

The products formed using the methathesis route, Grignard chemistry, Wittig chemistry, copper-mediated couplings, palladium-catalyzed couplings, and bioengineering methods can also be combined to form the mixtures of the invention. For example, near terminal-branched fatty acids and alcohols produced using the metathesis route can be combined with near terminal-branched fatty acids and alcohols produced using the biological route to form the mixtures of the invention.

In yet another aspect of the invention, the mixtures of near terminal-branched fatty acids and/or alcohols that are formed using Grignard chemistry, Wittig chemistry, copper-mediated couplings, palladium-catalyzed couplings, bioengineering methods, the metathesis route, or mixtures thereof are derivatized to form compositions containing compounds that are useful for cleaning and/or conditioning applications such as for granular, bar-form, and liquid laundry detergents; liquid hand dishwashing compositions; liquid, gel, and bar-form personal cleansing products; shampoos; dentifrices; hard surface cleaners, hair conditioners, and the like.

Derivatization of the near terminal-branched fatty acid and fatty alcohols reaction products can occur by any method known in the art. For example, the near terminal-branched fatty alcohols can be alkyoxylated using standard commercial and laboratory techniques and/or sulfated/sulfonated using any convenient sulfating/sulfonating agent (e.g., chlorosulfonic acid, $SO_3$/air, or oleum) to form detergent compounds and conditioning compounds.

These compositions contain mixtures of at least two derivatized near terminal-branched fatty acids and/or alcohols of Formula I:

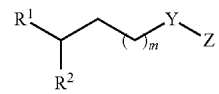

wherein m, $R^1$, $R^2$, are as defined above;

Y is null or $W_p$;

W is an alkyleneoxy moiety and p is the number of alkenyloxy units. In some embodiments, p is about 1 to about 30 units, preferably about 3 to about 30 units, more preferably about 5 to about 20 units, for example about 5 to about 15 units. In some embodiments, W is selected from the group consisting of ethylenoxy, propylenoxy, butylenoxy, and mixtures thereof. In preferred embodiments, W is ethylenoxy.

Z is a hydrophilic moiety selected from the group consisting of hydroxy, carboxylate, sulfate, disulfate, sulfonate, disulfonate, glycerol ester sulfonate, amine oxide, a polyhydroxy moiety, a phosphate ester, glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether, a glycerol ether sulfate, a polyglycerol ether, a polyglycerol ether sulfate, sorbitan ester, ammonioalkanesulfonate, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, a sulfonated alkyl ester, and a sulfonated fatty acid.

In one embodiment herein, the foregoing selections for Z do not include carboxylate.

For cleaning applications, Z can include, for example: carboxylate, sulfate, disulfate, sulfonate, disulfonate, glycerol ester sulfonate, amine oxide, a polyhydroxy moiety, a phosphate ester, glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether sulfate, a polyglycerol ether sulfate, ammonioalkanesulfonate, amidopropyl betaine, imidazoline, alken-2-yl-succinate, and a sulfonated fatty acid. In one embodiment herein, the foregoing selections for Z do not include carboxylate.

For conditioning application, Z can include, for example: hydroxy, a polyhydroxy moiety, a phosphate ester, a polyphosphate ester, dialkanolamide, monoalkanolamide, diglycolamide, a glycerol ester, a glycerol ether, a polyglycerol ether, sorbitan ester, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, and a sulfonated alkyl ester. In one embodiment herein, the foregoing selections for Z do not include carboxylate.

In some preferred embodiments, Z is hydroxy, carboxylate, sulfate, sulfonate, tertiary amine, amine oxide, monoalkanolamide, amidopropyl betaine, and an alkylated quat. In one embodiment herein, the foregoing selections for Z do not include carboxylate.

In some embodiments, the derivatized at least two compounds of Formula I require a counterion, as previously described.

The at least two compounds of Formula I have different chemical structures and are present in the composition in at least about 50 wt %, preferably at least about 75 wt %, more preferably at least about 90 wt %, for example, about 95 wt %, up to and including about 100 wt %, based on the total weight of the composition.

The at least two compounds of Formula I can have a length of about 8 carbon atoms to about 40 carbon atoms, preferably about 10 carbon atoms to about 30 carbon atoms. The exact length of the at least two compounds of Formula I depends on their desired use, as previously described herein. The branching on the at least two compounds of Formula I occurs as previously described herein. The mixtures of the at least two compounds of Formula I can include any weight percentage of iso compounds of Formula I, as previously described herein. The compositions containing mixtures of the at least two compounds of Formula I are substantially free of secondary hydroxy compounds, as previously described herein.

The compositions containing mixtures of the at least two compounds of Formula I optionally include linear compounds, mid-chain branched compounds, or mixtures thereof in an amount of no more than about 50 wt %, preferably no more than 10 wt %, for example, no more than about 2 wt %, based on the total weight of the mixture, as previously described herein.

Analytical analysis of compositions containing mixtures of compounds of Formula I can be performed as follows.

Gas Chromatography (GC) analysis method/conditions for near terminal olefins, paraffins, methyl esters, and alcohols.
ISTD/Calibration Solution Prep
  Add 5 gram pure Hexadecane to a 100 mL vol. flask.
  Record weight to nearest 0.0001 g.
  Fill to volume with DCM ($CH_2Cl_2$).
  Stopper and mix well.
Sample Prep
  If sample contains catalyst, pass through PTFE syringe filter (0.45 um)
  Tare a 2 mL GC vial.
  Using a micro-pipette dispense 50 uL of sample into GC vial.
  Record weight to nearest 0.1 mg
  Re-tare vial and sample.
  Pipette 1000 uL of ISTD/Calibration solution into GC vial.
  Record weight to nearest 0.1 mg.
  Crimp seal and shake to mix.
  Inject on GC using . . . Fast GC Method protocol
Fast GC Method Instrument Operation
  Column: Restek RTX-5 (10244) 105 m×0.25 mm×0.50 um df
  Oven: Maximum temp.: 330° C.
  Total run time: 35 min Rate: 5.0 C °/min
  Initial temp: 180° C. Final temp: 320° C.
  Inlet:
  Mode: Split
  Split Ratio: 50:1
  Inlet temp: 300° C.
  Carrier gas: He
  Linear velocity: 20 cm/sec.
  Injector:
  Injection volume: 0.2 µL Solvent A&B: DCM ($CH_2Cl_2$)
  Sample washes: 3 Solvent washes (A): 3
  Sample pumps: 5 Solvent washes (B): 3
  Detector (FID):
  Temp. 320° C.
  Hydrogen flow: 40 mL/min
  Air flow: 450 mL/min
  Makeup gas: $N_2$
  Makeup flow: 45 mL/min

INDUSTRIAL USES

The compositions of the invention that contain mixtures of near terminal-branched fatty acids, fatty alcohols, and derivatives thereof provide superior performance when used in cleaning compositions and personal care compositions. As previously described, the compositions containing the mixtures described herein have high performance in cold, hard water, good solubility and grease removal, improved compaction, high sudsing ability in the absence of hard water, and good biodegradability. Further, they are stable at low temperatures, they dilute quickly and easily, and are relatively inexpensive.

Thus, in another aspect, the invention relates to a cleaning composition or personal care composition containing about 0.001 wt % to about 100 wt %, preferably about 0.1 wt % to about 80 wt %., more preferably about 1 wt % to about 25 wt % by weight of a mixture of at least two compounds of Formula I:

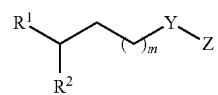

wherein $R^1$ is hydrogen, methyl, or ethyl;
$R^2$ is $(C_1$-$C_n)$alkyl or $(C_1$-$C_n)$alkenyl having 0, 1, 2, or 3 $(C_1$-$C_3)$alkyl branches, wherein branching occurs on carbon atoms that are within 40% of the nonfunctionalized terminus of the longest carbon chain;
m is 5-37 and n is 1-33, wherein m+n is 6-38; preferably m is 7-27 and n is 1-23, wherein m+n is 8-28; for example, when m is 7, n is 9, and when m is 11, n is 17;
Y is null or $W_p$;
W is selected from the group consisting of ethylenoxy, propylenoxy, butylenoxy, and mixtures thereof;
p is 1 to 30; and,
Z is a hydrophilic moiety selected from the group consisting of hydroxy, carboxylate, sulfate, disulfate, sulfonate, disulfonate, glycerol ester sulfonate, amine oxide, a polyhydroxy moiety, a phosphate ester, glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether, a glycerol ether sulfate, a polyglycerol ether, a polyglycerol ether sulfate, sorbitan ester, an aminopolyglycoside, urea, ammonioalkanesulfonate, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, a sulfonated alkyl ester, and a sulfonated fatty acid. Preferably Z can include hydroxy, carboxylate, sulfate, sulfonate, amine oxide, monoalkanolamide, amidopropyl betaine, and an alkylated quat;
wherein with respect to at least one of the compounds, when $R^1$ is H, then $R^2$ has 1, 2, or 3 ($C_1$-$C_3$) alkyl branches, and when $R^1$ is methyl or ethyl, then $R^2$ has 0, 1, or 2 ($C_1$-$C_3$)alkyl branches. In one embodiment, with respect to the at least two compounds, when $R^1$ is H, then $R^2$ has 1, 2, or 3 ($C_1$-$C_3$) alkyl branches, and when $R^1$ is methyl or ethyl, then $R^2$ has 0, 1, or 2 ($C_1$-$C_3$)alkyl branches.

In one embodiment herein, the foregoing selections for Z do not include carboxylate.

The at least two compounds of Formula I can have a length of about 8 carbon atoms to about 40 carbon atoms, preferably about 10 carbon atoms to about 30 carbon atoms, wherein the exact length depends on the desired use, as previously described herein. The branching on the at least two compounds of Formula I occurs within 40% of the nonfunctionalized terminus of the longest carbon chain, as previously described herein. In preferred embodiments, the compounds of Formula I comprise iso branching, anteiso branching, or mixtures thereof. In some embodiments when $R^2$ has 5 or less carbon atoms in its longest chain, $R^1$ can be hydrogen, methyl, or ethyl. In other embodiments when $R^2$ has 6 or more carbon atoms in its longest chain, $R^1$ is hydrogen.

The near terminal-branching on the at least two compounds of Formula I is composed of ($C_1$-$C_3$)alkyl moieties, as previously described herein. Preferably, the branches include methyl moieties, ethyl moieties, and mixtures thereof. More preferably, the branches include methyl moieties.

The at least two near terminal-branched compounds of Formula I include one branch, two branches, or three branches. In preferred embodiments, the at least two compounds of Formula I each have one branch. In some embodiments, the at least two compounds of Formula I have two or three branches and two of these branches are at the iso position. In other embodiments, the at least two compounds have two or three branches and none of these branches are geminal. In embodiments when $R^2$ has three branches, $R^1$ is hydrogen.

The mixtures in this embodiment of the invention can include from 0 wt % to about 100 wt % of iso compounds based on the total weight of near terminal-branched compounds. In some embodiments, the mixtures of the invention include about 1 wt % to about 40 wt % of iso compounds, based on the total weight of near terminal-branched compounds. In other embodiments, the mixtures of the invention include about 10 wt % to about 30 wt % of iso compounds, based on the total weight of near terminal-branched compounds. In some embodiments, the near terminal-branched compounds include only anteiso compounds.

I. Cleaning Compositions

In one embodiment, the invention relates to cleaning compositions that include about 0.001 wt % to about 100 wt %, preferably about 0.1 wt % to about 80 wt %., more preferably about 1 wt % to about 25 wt %, by weight, of the mixture of the compounds of Formula I, wherein Y is null or Wp, wherein Wp is poly(alkyleneoxy) wherein p is from 1-30, and Z can include, for example, carboxylate, sulfate, disulfate, sulfonate, disulfonate, glycerol ester sulfonate, amine oxide, a polyhydroxy moiety, a phosphate ester, glycerol sulfonate, polygluconate, a polyphosphate ester, an aminopolyglycoside, urea, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether sulfate, a polyglycerol ether sulfate, ammonioalkanesulfonate, amidopropyl betaine, imidazoline, alken-2-yl-succinate, and a sulfonated fatty acid. In one embodiment herein, the foregoing selections for Z do not include carboxylate.

In some embodiments, the mixture of the invention includes compounds that have 8 to 17 total carbon atoms and is encompassed by Compounds 1-36 in Table A; Compounds 1-11 in Table B; and Compounds 1-9 in Table C, wherein Z is as defined above, and preferably is hydroxy, carboxylate, sulfate, sulfonate, and amine oxide. For example, near terminal-branched compounds in the mixtures of this embodiment of the invention can include 12-methyltetradecylsulfate, 11-methyltetradecylsulfate, 12-methyltridecylsulfate.

The cleaning compositions of this aspect of the invention may also contain additional cleaning components. The precise nature of these additional components and levels of incorporation thereof will depend on the physical form of the composition, and the precise nature of the cleaning operation for which it is to be used. The longer-chain derivatives are more soluble than expected and the shorter-chain derivatives clean better than expected. Cleaning compositions herein include, but are not limited to: granular, bar-form, and liquid laundry detergents; liquid hand dishwashing compositions; hard surface cleaners, and the like. Also included are a sachet, a two in one pouch containing both solid and liquid compartments, a tablet, a disinfectant for hospitals, an industrial cleaner, a decontaminant for biological or chemical warfare agents and the like. Such compositions can contain a variety of conventional detersive ingredients.

The compositions of the invention preferably contain one or more additional detergent components selected from surfactants, enzymes, builders, alkalinity system, organic polymeric compounds, suds suppressors, soil suspension, anti-redeposition agents and corrosion inhibitors. This listing of such ingredients is exemplary only, and not by way of limitation of the types of ingredients which can be used with the near terminal-branched surfactants herein. A detailed description of additional components can be found in U.S. Pat. No. 6,020,303.

Bleaching Compounds, Bleaching Agents, Bleach Activators, and Bleach Catalysts

The cleaning compositions herein may further contain bleaching agents or bleaching compositions containing a bleaching agent and one or more bleach activators. Bleaching agents will typically be at levels of from about 1 wt % to about 30 wt %, more typically from about 5 wt % to about 20 wt %, based on the total weight of the composition, especially for fabric laundering. If present, the amount of bleach activators will typically be from about 0.1 wt % to about 60 wt %, more typically from about 0.5 wt % to about 40 wt % of the bleaching composition comprising the bleaching agent-plus-bleach activator.

Examples of bleaching agents include oxygen bleach, perborate bleache, percarboxylic acid bleach and salts thereof, peroxygen bleach, persulfate bleach, percarbonate bleach, and mixtures thereof. Examples of bleaching agents are disclosed in U.S. Pat. No. 4,483,781, U.S. patent application Ser. No. 740,446, European Patent Application 0,133,354, U.S. Pat. No. 4,412,934, and U.S. Pat. No. 4,634,551.

Examples of bleach activators (e.g., acyl lactam activators) are disclosed in U.S. Pat. Nos. 4,915,854; 4,412,934; 4,634,551; 4,634,551; and 4,966,723.

Preferably, a laundry detergent composition comprises a transition metal catalyst. Preferably, the transition metal catalyst may be encapsulated. The transition metal bleach catalyst typically comprises a transition metal ion, preferably selected from transition metal selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W (IV), W(V), W(VI), Pd(II), Ru(II), Ru(III), and Ru(IV), more preferably Mn(II), Mn(III), Mn(IV), Fe(II), Fe(III), Cr(II), Cr(III), Cr(IV), Cr(V), and Cr(VI). The transition metal bleach catalyst typically comprises a ligand, preferably a macropolycyclic ligand, more preferably a cross-bridged macropolycyclic ligand. The transition metal ion is preferably coordinated with the ligand. Preferably, the ligand comprises at least four donor atoms, at least two of which are bridgehead donor atoms. Suitable transition metal bleach catalysts are described in U.S. Pat. No. 5,580,485, U.S. Pat. No. 4,430,243; U.S. Pat. No. 4,728,455; U.S. Pat. No. 5,246,621; U.S. Pat. No. 5,244,594; U.S. Pat. No. 5,284,944; U.S. Pat. No. 5,194,416; U.S. Pat. No. 5,246,612; U.S. Pat. No. 5,256,779; U.S. Pat. No. 5,280,117; U.S. Pat. No. 5,274,147; U.S. Pat. No. 5,153,161; U.S. Pat. No. 5,227,084; U.S. Pat. No. 5,114,606; U.S. Pat. No. 5,114,611, EP 549,271 A1; EP 544,490 A1; EP 549,272 A1; and EP 544,440 A2. A suitable transition metal bleach catalyst is a manganese-based catalyst, for example disclosed in U.S. Pat. No. 5,576,282. Suitable cobalt bleach catalysts are described, for example, in U.S. Pat. No. 5,597,936 and U.S. Pat. No. 5,595,967. Such cobalt catalysts are readily prepared by known procedures, such as taught for example in U.S. Pat. No. 5,597,936, and U.S. Pat. No. 5,595,967. A suitable transition metal bleach catalyst is a transition metal complex of ligand such as bispidones described in WO 05/042532 A1.

Bleaching agents other than oxygen bleaching agents are also known in the art and can be utilized herein (e.g., photoactivated bleaching agents such as the sulfonated zinc and/or aluminum phthalocyanines (U.S. Pat. No. 4,033,718, incorporated herein by reference), or pre-formed organic peracids, such as peroxycarboxylic acid or salt thereof, or a peroxysulphonic acid or salt thereof. A suitable organic peracid is phthaloylimidoperoxycaproic acid. If used, household cleaning compositions will typically contain from about 0.025% to about 1.25%, by weight, of such bleaches, especially sulfonate zinc phthalocyanine.

Enzymes

Enzymes are included in the present cleaning compositions for a variety of purposes, including removal of protein-based, carbohydrate-based, or triglyceride-based stains from substrates, for the prevention of refugee dye transfer in fabric laundering, and for fabric restoration. Suitable enzymes include proteases, amylases, lipases, cellulases, peroxidases, and mixtures thereof of any suitable origin, such as vegetable, animal, bacterial, fungal and yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the household cleaning composition. Stated otherwise, the compositions herein will typically comprise from 0.001% to 5%, preferably 0.01%-1% by weight of a commercial enzyme preparation.

A range of enzyme materials and means for their incorporation into synthetic detergent compositions is also disclosed in WO 9307263 A; WO 9307260 A; WO 8908694 A; U.S. Pat. Nos. 3,553,139; 4,101,457; and U.S. Pat. No. 4,507,219. Enzyme materials useful for liquid detergent formulations, and their incorporation into such formulations, are disclosed in U.S. Pat. No. 4,261,868. Enzymes for use in detergents can be stabilized by various techniques. Enzyme stabilisation techniques are disclosed and exemplified in U.S. Pat. Nos. 3,600,319 and 3,519,570; EP 199,405, EP 200,586; and WO 9401532 A.

Enzyme Stabilizing System

The enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

Builders

Detergent builders selected from aluminosilicates and silicates are preferably included in the compositions herein, for example to assist in controlling mineral, especially calcium and/or magnesium hardness in wash water or to assist in the removal of particulate soils from surfaces. Also suitable for use herein are synthesized crystalline ion exchange materials or hydrates thereof having chain structure and a composition represented by the following general Formula I an anhydride form: $x(M_2O).ySiO_2.zM'O$ wherein M is Na and/or K, M' is Ca and/or Mg; y/x is 0.5 to 2.0 and z/x is 0.005 to 1.0 as taught in U.S. Pat. No. 5,427,711. Detergent builders in place of or in addition to the silicates and aluminosilicates described hereinbefore can optionally be included in the compositions herein, for example to assist in controlling mineral, especially calcium and/or magnesium hardness in wash water or to assist in the removal of particulate soils from surfaces.

Builder level can vary widely depending upon end use and physical form of the composition. Built detergents typically comprise at least about 1 wt % builder, based on the total weight of the detergent. Liquid formulations typically comprise about 5 wt % to about 50 wt %, more typically 5 wt % to 35 wt % of builder to the total weight of the detergent. Granular formulations typically comprise from about 10% to about 80%, more typically 15% to 50% builder by weight of the detergent composition. Lower or higher levels of builders are not excluded. For example, certain detergent additive or high-surfactant formulations can be unbuilt.

Suitable builders herein can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Detersive Surfactants

The detergent compositions according to the present invention preferably further comprise additional surfactants, herein also referred to as co-surfactants. It is to be understood that the mixtures of near terminal-branched surfactants prepared in the manner of the present invention may be used singly in cleaning compositions or in combination with other detersive surfactants. Typically, fully-formulated cleaning compositions will contain a mixture of surfactant types in order to obtain broad-scale cleaning performance over a variety of soils and stains and under a variety of usage conditions. One advantage of the mixtures of near terminal-branched surfactants herein is their ability to be readily formulated in combination with other known surfactant types. Nonlimiting examples of additional surfactants which may be used herein typically at levels from about 1% to about 55%, by weight, include the unsaturated sulfates, the $C_{10}$-$C_{18}$ alkyl alkoxy, $C_{10}$-$C_{18}$ alkyl alkoxy carboxylates, the $C_{10}$-$C_{18}$ glycerol ether sulfates, the $C_{10}$-$C_{18}$ alkyl polyglycosides and their corresponding sulfated polyglycosides, and $C_{12}$-$C_{18}$ alpha-sulfonated fatty acid esters. Nonionic surfactants such as the ethoxylated $C_{10}$-$C_{18}$ alcohols and alkyl phenols can also be used. If desired, other conventional surfactants such as the $C_{12}$-$C_{18}$ betaines and sulfobetaines ("sultaines"), $C_{10}$-$C_{18}$ amine oxides, and the like, can also be included in the overall compositions. The $C_{10}$-$C_{18}$ N-alkyl polyhydroxy fatty acid amides can also be used. See WO 9,206,154. Other sugar-derived surfactants include the N-alkoxy polyhydroxy fatty acid amides. The N-propyl through N-hexyl $C_{12}$-$C_{18}$ glucamides can be used for low sudsing. $C_{10}$-$C_{20}$ conventional soaps may also be used. If high sudsing is desired, the branched-chain $C_{10}$-$C_{16}$ soaps may be used. $C_{10}$-$C_{14}$ alkyl benzene sulfonates (LAS), which are often used in laundry detergent compositions, can also be used with the branched surfactants herein.

A wide range of these co-surfactants can be used in the detergent compositions of the present invention. A typical listing of anionic, nonionic, ampholytic and zwitterionic classes, and species of these co-surfactants, is given in U.S. Pat. No. 3,664,961. Amphoteric surfactants are also described in detail in "Amphoteric Surfactants, Second Edition", E. G. Lomax, Editor (published 1996, by Marcel Dekker, Inc.)

The laundry detergent compositions of the present invention typically comprise from about 0.1% to about 35%, preferably from about 0.5% to about 15%, by weight of co-surfactants. (e.g., anionic co-surfactants, nonionic co-surfactants, cationic co-surfactants).

Amine-Neutralized Anionic Surfactants

Anionic surfactants of the present invention and adjunct anionic cosurfactants may be neutralized by amines or alkanolamines, and alkanolamines are preferred. Suitable non-limiting examples including monoethanolamine, triethanolamine, and other alkanolamines known in the art.

Polymeric Soil Release Agent

Known polymeric soil release agents, hereinafter "SRA" or "SRA's", can optionally be employed in the present detergent compositions. If utilized, SRA's will generally comprise from 0.01% to 10.0%, typically from 0.1% to 5%, preferably from 0.2% to 3.0% by weight, of the composition.

Preferred SRA's typically have hydrophilic segments to hydrophilize the surface of hydrophobic fibers such as polyester and nylon, and hydrophobic segments to deposit upon hydrophobic fibers and remain adhered thereto through completion of washing and rinsing cycles thereby serving as an anchor for the hydrophilic segments. This can enable stains occurring subsequent to treatment with SRA to be more easily cleaned in later washing procedures.

SRA's can include, for example, a variety of charged, e.g., anionic or even cationic (see U.S. Pat. No. 4,956,447), as well as noncharged monomer units and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products. Examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044, all of which are.

Clay Soil Removal/Anti-Redeposition Agents

The compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylates amines; liquid detergent compositions typically contain about 0.01% to about 5% by weight.

Exemplary clay soil removal and antiredeposition agents are described in U.S. Pat. Nos. 4,597,898; 548,744; 4,891,160; European Patent Application Nos. 111,965; 111,984; 112,592; and WO 95/32272, which are all.

Polymeric Dispersing Agents

Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition. Examples of polymeric dispersing agents are found in U.S. Pat. No. 3,308,067, European Patent Application No. 66915, EP 193,360, and EP 193,360, which are.

Alkoxylated Polyamine Polymers

Soil suspension, grease cleaning, and particulate cleaning polymers may include the alkoxylated polyamines. Such materials include but are not limited to ethoxylated polyethyleneimine, ethoxylated hexamethylene diamine, and sulfated versions thereof. A useful example is 600 g/mol polyethyleneimine core ethoxylated to 20 EO groups per NH and is available from BASF.

Brighteners

Any optical brighteners or other brightening or whitening agents known in the art can be incorporated at levels typically from about 0.01% to about 1.2%, by weight, into the cleaning compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific examples of optical brighteners which are useful in the present compositions are those identified in U.S. Pat. No. 4,790,856 and U.S. Pat. No. 3,646,015, which are.

Fabric Hueing Agents

The compositions of the present invention my include fabric hueing agents. Non-limiting examples include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein. If utilized, these chelating agents will generally comprise from about 0.1% to about 15% by weight of the detergent compositions herein. More preferably, if utilized, the chelating agents will comprise from about 0.1% to about 3.0% by weight of such compositions.

Suds Suppressors

Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574, and in front-loading European-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265,779; 4,265,779; 3,455,839; 3,933,672; 4,652,392; 4,978,471; 4,983,316; 5,288,431; 4,639,489; 4,749,740; and 4,798,679; 4,075,118; European Patent Application No. 89307851.9; EP 150,872; and DOS 2,124,526 which are all.

For any detergent compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 10% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%-3% by weight of the finished compositions.

Structurant/Thickeners

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant, preferably from 0.01 wt % to 5 wt %, from 0.1 wt % to 2.0 wt % structurant. The structurant is typically selected from the group consisting of diglycerides and triglycerides, ethylene glycol distearate, microcrystalline cellulose, cellulose-based materials, microfiber cellulose, biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680.

Such structurants have a thread-like structuring system having a range of aspect ratios. Other suitable structurants and the processes for making them are described in WO2010/034736.

Alkoxylated Polycarboxylates

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —$(CH_2CH_2O)_m$ $(CH_2)_n CH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Amphilic Graft Co-Polymer

The near-terminal branched surfactants of the present invention, and their mixtures with other cosurfactants and other adjunct ingredients, are particularly suited to be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF.

Fabric Softeners

Various through-the-wash fabric softeners, especially the impalpable smectite clays of U.S. Pat. No. 4,062,647, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, and U.S. Pat. No. 4,291,071.

Perfumes

Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual lay softeners can be used in combination with amine and cationic softeners perfumery ingredients can comprise from about 0.0001% to about 90% of a finished perfume composition.

Other Ingredients

A wide variety of other ingredients useful in the cleaning compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$-$C_{16}$ alkanolamides can be incorporated into the compositions, typically at 1%-10% levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1%-2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% by weight of such carriers.

The cleaning compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9-11. Techniques for controlling pH at recommended usage levels include the use of buffers, alkalis, acids, etc., and are well known to those skilled in the art.

Form of the Compositions

The compositions in accordance with the invention can take a variety of physical forms including granular, tablet, bar and liquid forms. Also included are a sachet, a two in one pouch containing both solid and liquid compartments, and a tablet. The compositions are particularly the so-called concentrated granular detergent compositions adapted to be added to a washing machine by means of a dispensing device placed in the machine drum with the soiled fabric load.

The mean particle size of the components of granular compositions in accordance with the invention should preferably be such that no more that 5% of particles are greater than 1.7 mm in diameter and not more than 5% of particles are less than 0.15 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

The bulk density of granular detergent compositions in accordance with the present invention typically have a bulk density of at least 600 g/liter, more preferably from 650 g/liter to 1200 g/liter. Bulk density is measured by means of a simple funnel and cup device consisting of a conical funnel moulded rigidly on a base and provided with a flap valve at its lower extremity to allow the contents of the funnel to be emptied into an axially aligned cylindrical cup disposed below the funnel. The funnel is 130 mm high and has internal diameters of 130 mm and 40 mm at its respective upper and lower extremities. It is mounted so that the lower extremity is 140 mm above the upper surface of the base. The cup has an overall height of 90 mm, an internal height of 87 mm and an internal diameter of 84 mm. Its nominal volume is 500 mm.

To carry out a measurement, the funnel is filled with powder by hand pouring, the flap valve is opened and powder allowed to overfill the cup. The filled cup is removed from the frame and excess powder removed from the cup by passing a straight edged implement eg; a knife, across its upper edge. The filled cup is then weighed and the value obtained for the weight of powder doubled to provide a bulk density in g/liter. Replicate measurements are made as required.

Near Terminal-Branched Surfactant Agglomerate Particles

The mixtures of compounds of Formula I, as described herein are preferably present in granular compositions in the form of near terminal-branched surfactant agglomerate particles, which may take the form of flakes, prills, marumes, noodles, ribbons, but preferably take the form of granules. The most preferred way to process the particles is by agglomerating powders (e.g. aluminosilicate, carbonate) with high active near terminal-branched surfactant pastes and to control the particle size of the resultant agglomerates within specified limits. Such a process involves mixing an effective amount of powder with a active near terminal-branched surfactant paste in one or more agglomerators such as a pan agglomerator, a Z-blade mixer or more preferably an in-line mixer such as those manufactured by Schugi (Holland) BV, 29 Chroomstraat 8211 AS, Lelystad, Netherlands, and Gebruder Lodige Maschinenbau GmbH, D-4790 Paderborn 1, Elsenerstrasse 7-9, Postfach 2050, Germany. Most preferably a high shear mixer is used, such as a Lodige CB (Trade Name).

A high active near terminal branched surfactant paste comprising from 50% by weight to 95% by weight, preferably 70% by weight to 85% by weight of active near terminal-branched surfactant is typically used. The paste may be pumped into the agglomerator at a temperature high enough to maintain a pumpable viscosity, but low enough to avoid degradation of the surfactants used. An operating temperature of the paste of 50° C. to 80° C. is typical.

Compacted Liquid or Powder Detergents

The near-terminal branched surfactants of the present invention, and their mixtures with other cosurfactants and other adjunct ingredients, are particularly suited to compact detergent formulations. For liquid detergents, the composition preferably comprises less than 20 wt %, or less than 10 wt %, or less than 5 wt %, or less than 4 wt % or less than 3 wt % free water, or less than 2 wt % free water, or less than 1 wt % free water, and may even be anhydrous, typically comprising no deliberately added free water. Free water is typically measured using Karl Fischer titration. The laundry detergent composition (2 g) is extracted into 50 ml dry methanol at room temperature for 20 minutes and analyse 1 ml of the methanol by Karl Fischer titration. For powder detergents, the amount of filler (sodium sulfate, sodium chloride, clay, or other inert solid ingredients) preferably comprises less than 20 wt %, or less than 10 wt %, or less than 5 wt %, or less than 4 wt % or less than 3 wt % free water, or less than 2 wt % free water, or less than 1 wt % filler.

Laundry Washing Method

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is meant from 20 g to 300 g of product dissolved or dispersed in a wash solution of volume from 5 to 65 liters, as are typical product dosages and wash solution volumes commonly employed in conventional machine laundry methods.

As noted, the mixtures of compounds of Formula I are used herein in cleaning compositions, preferably in combination with other detersive surfactants, at levels which are effective for achieving at least a directional improvement in cleaning performance. In the context of a fabric laundry composition, such "usage levels" can vary depending not only on the type and severity of the soils and stains, but also on the wash water temperature, the volume of wash water and the type of washing machine (e.g., top-loading, front-loading, top-loading, vertical-axis Japanese-type automatic washing machine).

As can be seen from the foregoing, the amount of mixtures of compounds of Formula I used in a machine-wash laundering context can vary, depending on the habits and practices of the user, the type of washing machine, and the like. In this context, however, one heretofore unappreciated advantage of the mixtures of compounds of Formula I is their ability to provide at least directional improvements in performance over a spectrum of soils and stains even when used at relatively low levels with respect to the other surfactants (generally anionics or anionic/nonionic mixtures) in the finished compositions.

In addition, another advantage of the mixtures of the compounds of Formula I and the detergent compositions containing them is their desirable performance in cold water. The invention herein includes methods for laundering of fabrics at reduced wash temperatures. This method of laundering fabric comprises the step of contacting a laundry detergent composition to water to form a wash liquor, and laundering fabric in said wash liquor, wherein the wash liquor has a temperature of above 0° C. to 20° C., preferably to 19° C., or to 18° C., or to 17° C., or to 16° C., or to 15° C., or to 14° C., or to 13° C., or to 12° C., or to 11° C., or to 10° C., or to 9° C., or to 8° C., or to 7° C., or to 6° C., or even to 5° C. The fabric may be contacted to the water prior to, or after, or simultaneous with, contacting the laundry detergent composition with water.

A further method of use of the materials of the present invention involves pretreatment of stains prior to laundering.

Hand Machine Dishwashing Methods

Any suitable methods for machine washing or cleaning soiled tableware, particularly soiled silverware are envisaged.

A preferred liquid hand dishwashing method involves either the dissolution of the detergent composition into a recepticle containing water, or by the direct application of the liquid hand dishwashing detergent composition onto soiled dishware.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition in accord with the invention. By an effective amount of the machine dishwashing composition it is meant from 8 g to 60 g of product dissolved or dispersed in a wash solution of volume from 3 to 10 liters, as are typical product dosages and wash solution volumes commonly employed in conventional machine dishwashing methods.

Packaging for the Compositions

Commercially marketed executions of the bleaching compositions can be packaged in any suitable container including those constructed from paper, cardboard, plastic materials and any suitable laminates. An optional packaging execution is described in European Application No. 94921505.7.

II. Personal Care Compositions

In another embodiment, the invention relates to personal care compositions that include about 0.001 wt % to about 100 wt %, preferably about 0.1 wt % to about 80 wt %., more preferably about 1 wt % to about 25 wt %, by weight of the mixture of the compounds of Formula I, wherein Z can include, for example: hydroxy, a polyhydroxy moiety, a phosphate ester, a polyphosphate ester, dialkanolamide, monoalkanolamide, diglycolamide, a glycerol ester, a glycerol ether, a polyglycerol ether, sorbitan ester, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, and a sulfonated alkyl ester.

When used in personal care compositions, the mixtures containing compounds of Formula I provide superior performance when used in conditioning applications, such as, for example, hair conditioners. In fact, the biodegradable mixture of the invention can act as a sustainable alternative to silicone. In cleaning applications, these compositions are stable at low temperatures, dilute quickly and easily, and tolerate hard water conditions.

In some embodiments where the mixture of the invention is used in a conditioning application, the mixture of the invention includes compounds that have 16 to 36 total carbon atoms and are encompassed by Compounds 32-62 in Table A, Compounds 1-22 in Table B, and Compounds 1-34 in Table C, wherein Z is as defined above, and preferably is hydroxy, monoalkanolamide, amidopropyl betaine, and an alkylated quat. For example, near terminal-branched compounds in the mixtures of this embodiment of the invention can include 15-methylhexadecanol, 14-methylhexadecanol, 15-methylheptadecanol, 14-methylhexadecylpalmitate, 13-methylhexadecylpalmitate, 15-methylhexadecylstearate, and 16-methylhexadecylstearate.

In some embodiments where the mixture of the invention is used in a personal care cleaning application, the mixture of the invention includes compounds that have 12 to 22 total carbon atoms and are encompassed by Compounds 11-42 in Table A, Compounds 1-16 in Table B, and Compounds 1-19 in Table C, wherein Z is as defined above, and preferably is hydroxy, carboxylate, sulfate, sulfonate, and amine oxide. For example, near terminal-branched compounds in the mixtures of this embodiment of the invention can include 10-methyldodecylsulfate, 11-methyldodecylsulfate, 10-methyldodecylsulfate-1-ethoxylated, and 11-methyldodecylsulfate-1-ethoxylated. In one embodiment herein, the foregoing selections for Z do not include carboxylate.

The personal care compositions of this aspect of the invention may also contain additional personal care components. The precise nature of these additional components and levels of incorporation thereof will depend on the physical form of the composition, and the precise nature of the operation for which it is to be used (e.g., cleaning, conditioning). Personal care compositions herein include, but are not limited to liquid, gel and bar-form personal cleansing products; shampoos; conditioners; dentifrices; and the like. Such compositions can contain a variety of conventional personal care ingredients. The ingredients described herein are for the convenience of the formulator, and not by way of limitation of the types of ingredients which can be used with the mixtures of near terminal-branched compounds herein.

The personal care composition can be a multiphase composition comprising visually distinct phases, wherein said visually distinct phases form a pattern selected from the group consisting of striped, swirled, spiral, marbled, and mixtures thereof.

The personal care composition can include thickeners; glossing and shine-imparting agents; dyes or color-imparting agents; particles; glitter or colored particles; and mixtures thereof. Additionally or alternatively, the personal care composition can include at least one silicone comprising an amine group, a surfactant, at least one cosmetically acceptable carrier, cationic polymers, and high melting point fatty compounds.

In one embodiment, the personal care composition is a hair styling composition and further comprises at least one hair fixing polymer and at least one cosmetically acceptable carrier. The hair styling composition may be in a form selected from the group consisting of mousses, hairsprays, pump sprays, gels, foams, and waxes. The hair styling composition may further comprise a propellant wherein said propellant is selected from the group consisting of propane, butane, and nitrogen gas. Other propellants are also suitable, for example 1,1-difluoroethane, compressed air, isobutene, dimethylether. The hair styling composition comprises a hair fixing polymer selected from the group consisting of anionic polymers, cationic polymers, nonionic polymers, zwitterionic polymers, amphoteric polymers, and mixtures thereof. In a preferred embodiment, the hair styling composition comprises a hair fixing polymer which comprises acrylate groups.

In another embodiment, preferred hair fixing polymers are in a quantity of from about 0.01% to about 20% by total weight of the composition, more preferably from about 1% to about 10%. Hair fixing polymers may be selected from polymers with anionic or anionizable groups, polymers with cationic or cationizable groups, zwitterionic and/or amphoteric polymers, and nonionic polymers.

The personal care compositions of the present inventions may include the following components:

Surfactant

The composition of the present invention may include a surfactant. The surfactant component can include an anionic surfactant, a zwitterionic or amphoteric surfactant, or a combination thereof. The concentration of the anionic surfactant component in the composition should be sufficient to provide the desired cleaning and lather performance, and generally range from about 5% to about 50%.

The anionic surfactant can include alkyl and alkyl ether sulfates, water-soluble salts of organic, sulfuric acid reaction products, reaction products of fatty acids esterified with isethionic acid, succinates, olefin sulfonates having about 10 to about 24 carbon atoms, and beta-alkyloxy alkane sulfonates. Nonlimiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; 2,528,378; 2,486,921; 2,486,922; 2,396,278; and 3,332,880.

Cationic Surfactant System

The composition of the present invention may comprise a cationic surfactant system. The cationic surfactant system can be one cationic surfactant or a mixture of two or more cationic surfactants. If present, the cationic surfactant system is included in the composition at a level by weight of from about 0.1% to about 10%, preferably from about 0.5% to about 8%, more preferably from about 1% to about 5%, still more preferably from about 1.4% to about 4%, in view of balance among ease-to-rinse feel, rheology and wet conditioning benefits.

A variety of cationic surfactants including mono- and dialkyl chain cationic surfactants can be used in the compositions of the present invention. Among them, preferred are mono-alkyl chain cationic surfactants in view of providing desired gel matrix and wet conditioning benefits. The mono-alkyl cationic surfactants are those having one long alkyl chain which has from 12 to 22 carbon atoms, preferably from 16 to 22 carbon atoms, more preferably C18-22 alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof.

Mono-long alkyl quaternized ammonium salts useful herein are those having the formula (II):

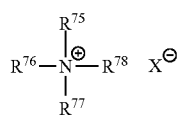

(II)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 22 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Examples of preferred mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Among them, highly preferred are behenyl trimethyl ammonium salt and stearyl trimethyl ammonium salt. In another embodiment, these are selected from the group consisting of behenyltrimmonium chloride, behenyltrimmonium methosulfate, cetyltrimethyl ammonium chloride, stearyltrimethyl ammonium chloride, dicetyldimethyl ammonium chloride, and distearyldimethyl ammonium chloride and mixtures thereof.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Although the mono-alkyl chain cationic surfactants are preferred, other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the composition at a level of from about 0.1% to about 40%, preferably from about 1% to about 30%, more preferably from about 1.5% to about 16% by weight of the composition, from about 1.5% to about 8% in view of providing improved conditioning benefits such as slippery feel during the application to wet hair, softness and moisturized feel on dry hair.

Cationic Polymers

The compositions of the present invention may contain a cationic polymer. Concentrations of the cationic polymer in the composition typically range from about 0.05% to about 3%, in another embodiment from about 0.075% to about 2.0%, and in yet another embodiment from about 0.1% to about 1.0%. Suitable cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

Suitable cationic polymers are described in U.S. Pat. Nos. 3,962,418; 3,958,581; and U.S. Publication No. 2007/0207109A1, which are all.

Nonionic Polymers

The composition of the present invention may include a nonionic polymer. Polyalkylene glycols having a molecular weight of more than about 1000 are useful herein. Useful are those having the following general formula:

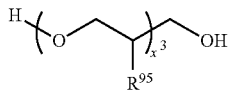

wherein $R^{95}$ is selected from the group consisting of H, methyl, and mixtures thereof.

Conditioning Agents

Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from about 0.01% to about 10%. Non-limiting examples of suitable silicone conditioning agents, and optional suspending agents for the silicone, are described in U.S. Reissue Pat. No. 34,584, U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US Patent Application Nos. 2007/0286837A1; 2005/0048549A1; 2007/0041929A1; British Pat. No. 849,433; German Patent No. DE 10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853, which are all.

Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. Pyridinethione anti-dandruff agents are described, for example, in U.S. Pat. No. 2,809,971; U.S. Pat. No. 3,236,733; U.S. Pat. No. 3,753, 196; U.S. Pat. No. 3,761,418; U.S. Pat. No. 4,345,080; U.S. Pat. No. 4,323,683; U.S. Pat. No. 4,379,753; and U.S. Pat. No. 4,470,982, which are all.

Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels of from about 0.1% to about 20%, more preferably from about 0.5% to about 5%.

Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%.

Suspending agents useful herein include anionic polymers and nonionic polymers (e.g., vinyl polymers, acyl derivatives, long chain amine oxides, and mixtures thereof, alkanol amides of fatty acids, long chain esters of long chain alkanol amides, glyceryl esters, primary amines having a fatty alkyl moiety having at least about 16 carbon atoms, secondary amines having two fatty alkyl moieties each having at least about 12 carbon atoms). Examples of suspending agents are described in U.S. Pat. No. 4,741,855.

Aqueous Carrier

The formulations of the present invention can be in the form of pourable liquids (under ambient conditions). Such compositions will therefore typically comprise an aqueous carrier, which is present at a level of from about 20% to about 95%, more preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Dispersed Particles

The compositions may optionally comprise particles. The particles may be dispersed water-insoluble particles. The particles may be inorganic, synthetic, or semi-synthetic. In one embodiment, the particles have an average mean particle size of less than about 300 μm.

Gel Matrix

The above cationic surfactants, together with high melting point fatty compounds and an aqueous carrier, may form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins (e.g., from about 0.001% to about 10%), peptides (e.g., from about $1\times10^{-7}$% to about 20%), sugar amines (e.g., from about 0.01% to about 15%), sunscreens (e.g., from about 1% to about 20%), oil control agents (e.g., from about 0.0001% to about 15%), tanning actives (e.g., 0.1% to about 20%), anti-acne actives (see, e.g., U.S. Pat. No. 5,607,980, incorporated herein by reference; and "Antiacne Agents" in the Personal Care Product Council's International Cosmetic Ingredient Dictionary and Handbook, 13th Ed.) desquamation actives (e.g., from about 0.01% to about 10%), see, e.g., U.S. Pat. Nos. 5,681, 852; 5,652,228, incorporated herein by reference), anti-cellulite actives (from about 0.1% to about 10%), chelating agents (see e.g., U.S. Pat. No. 5,487,884, International Publication Nos. WO91/16035 and WO91/16034, incorporated herein by reference), skin lightening agents (e.g., from about 0.1% to about 10%), flavonoids (see, e.g., U.S. Pat. No. 6,235, 773, incorporated herein by reference), protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, Nacyl amino acid compounds, antimicrobials, and antifungals (see e.g., U.S. application publication No. US 2006/0275237A1 and US 2004/0175347A1, incorporated herein by reference).

Other Optional Components

The compositions of the present invention may contain also vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine and minoxidil.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The compositions of the present invention may also contain antimicrobial agents which are useful as cosmetic biocides.

The compositions of the present invention may also contain chelating agents.

This list of aforementioned personal care additives is not meant to be exclusive, and other components can be used.

Formulations

The hair conditioners and shampoo formulations can be prepared by any conventional method well known in the art. The present invention can also be used in a compact hair care formulation. A compact formulation is a formula which delivers the same benefit to the consumer at a lower usage level. Compact formulations and methods of making compact formulations are described in US Application Publication No 2009/0221463A1.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

The following examples illustrate the present invention. It will be appreciated that other modifications of the present invention within the skill of those in the cleansing and conditioning formulation art can be undertaken without departing from the spirit and scope of this invention. All of the formulations exemplified hereinafter are prepared via conventional formulation and mixing methods unless specific methods are given.

All parts, percentages, and ratios herein are by weight unless otherwise specified. Some components may come from suppliers as dilute solutions. The levels given reflect the weight percent of the active material, unless otherwise specified. The excluded diluents and other materials are included as "Minors".

I. Metathesis of Glyceryl Trioleate with 3-Methyl-1-Hexene, 4-Methyl-1-Hexene and 4-Methyl-1-Pentene to Prepare Near Terminal Branched Alcohols The trioleate shown in the example below is a nonlimiting example of an oil that can be used to prepare the compounds of the invention. Other useful reactants and subsequent products thereof can be derived from the following oils: soybean, rapeseed, canola, palm, palm kernel, coconut, jatropha, high erucic rapeseed, cottonseed, tallow, yellow grease, corn, sunflower, babasu, and mixtures thereof. Furthermore, the olefin used in the metathesis reaction can be a single branched olefin component or a mixture of branched olefins or a mixture of branched olefins with other nonreactive impurities such as aromatic alkyls, paraffins, branched paraffins and cycloalkanes as additional nonlimiting examples of chemicals for use in the metathesis reaction.

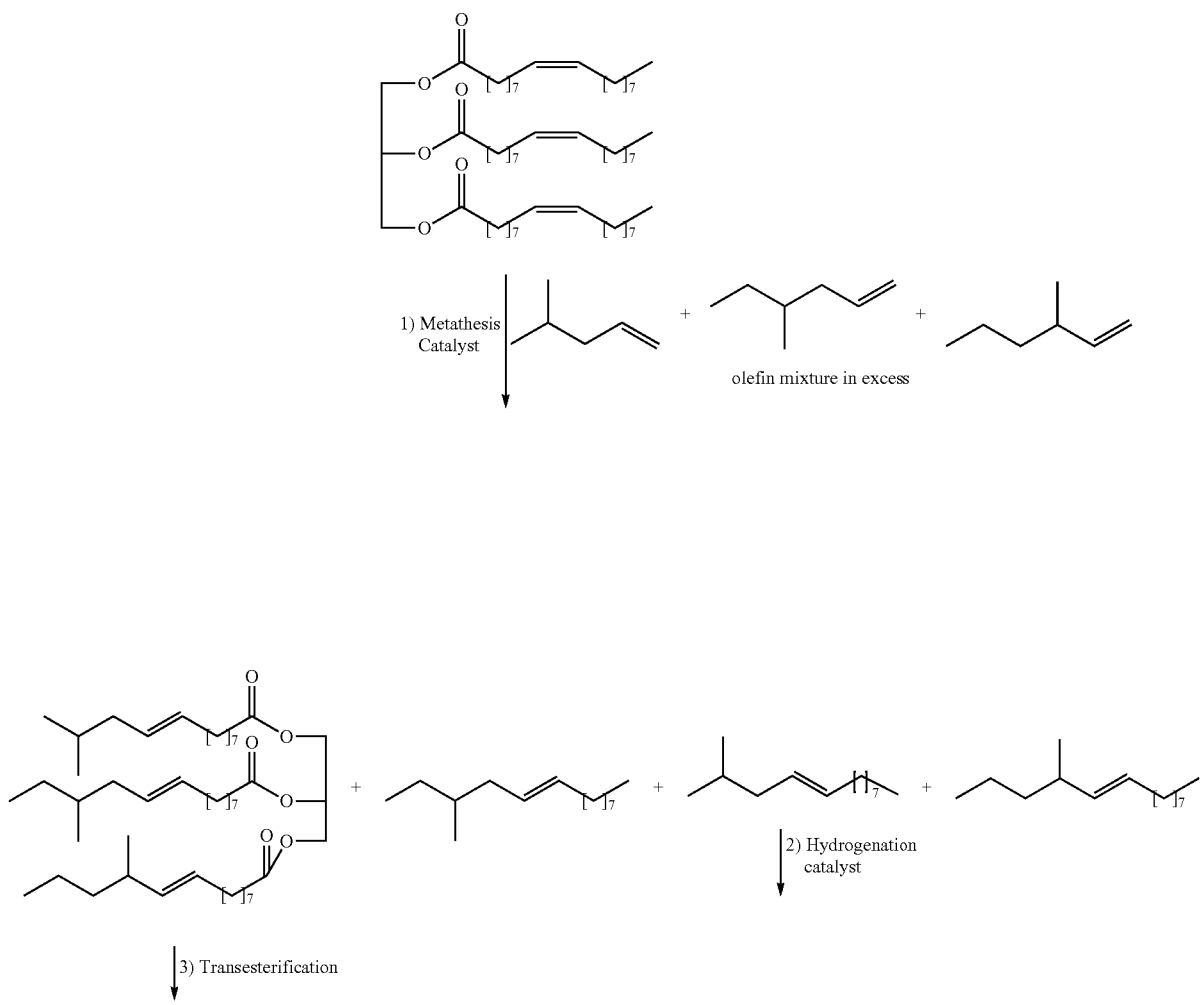

Scheme 1.

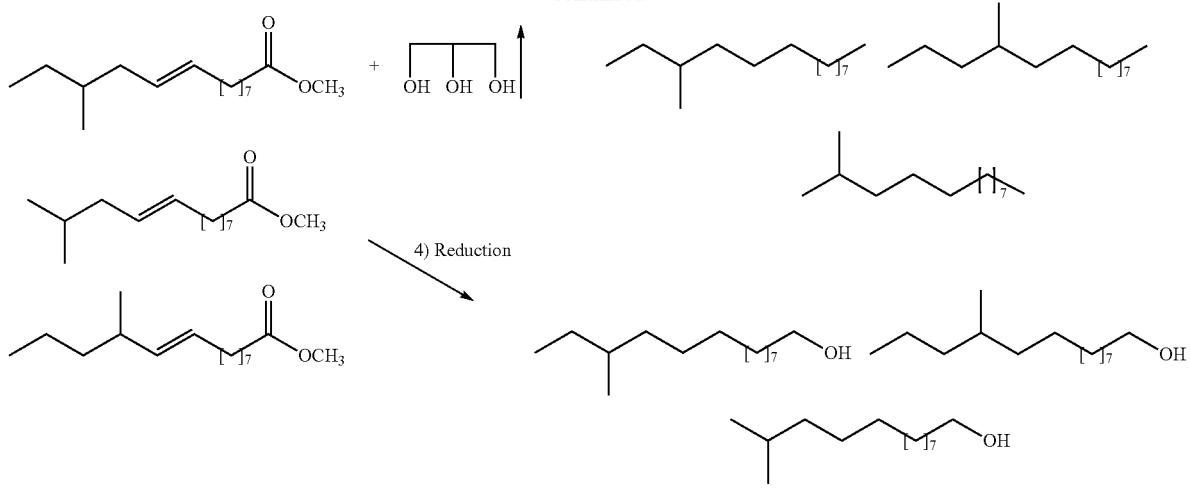

I.A. Synthesis of Mixture of Near Terminal-Branched Alcohols

About 8.854 g (0.010 mol) of glyceryl trioleate (Sigma catalog #T7140) and 25 mL of hexane are placed in a 316 stainless steel stirred pressure vessel. Solvent and gylceryl trioleate are predried over 4A molecular sieves prior to introduction to vessel. About 0.0006 mol of tungsten hexachloride and 0.0006 mol of tetramethyl tin is added to the vessel. The reactor is sealed, stirred, and purged several times with nitrogen. About 0.030 mol of a blend of 3-methyl-1-hexene, 4-methyl-1-hexene and 4-methyl-1-pentene is added to the vessel under nitrogen. The stirred mixture is heated to 220° C. under 100 psig nitrogen. Reaction is maintained at this temperature for several hours. The reactor is cooled and the product removed. The reaction mixture is quenched with 2-3 mL of concentrated ammonium hydroxide and extracted with additional 10 mL hexane. The hexane and any volatile olefins remaining are stripped on a rotary evaporator. The remaining product is subjected to fractional distillation to remove the remaining non volatile olefin mixture. This branched olefin mixture containing mainly a mixture of 11-methyl-9-tetradecene, 12-methyl-9-tridecene and 12-methyl-9-tetradecene is hydrogenated under standard reaction conditions to provide a high quality semi-biodiesel fuel with branching. The bottom of the flask from distillation contains mainly the new branched triglyceride mixture. This new triglyceride mixture is subjected to standard transesterification conditions in the presence of methanol and a catalytic amount of sodium hydroxide or sodium methoxide in methanol. The mixture phase separates into glycerine (bottom phase) and a mixture of methyl esters (top phase) consisting mainly of 12-methyl-9-tetradecenoic acid methyl ester, 12-methyl-9-tridecenoic acid methyl ester and 11-methyl-9-tetradecenoic acid methyl ester.

The unique branched methyl ester mixture is reduced using standard procedures with copper chromite catalyst in the presence of hydrogen to give essentially a mixture of 12-methyltetradecan-1-ol, 12-methyltridecan-1-ol and 11-methyltetradecan-1-ol (the near terminal branched alcohol mixture of the invention). The mixture is vacuum distilled to provide a purified mixture.

I.B. Sulfonation of the Mixture of Near Terminal-Branched Alcohols

A reaction vessel that has agitation and a nitrogen purge to exclude air is filled with 22.1 grams (approximately 0.1 mol) of the near terminal alcohol mixture prepared according to example I.A. 50 mls of diethyl ether is added. The mixture is chilled to −5° C. 12.23 grams (0.105 mol) of chlorosulfonic acid is added drop-wise while keeping the temperature of the mixture to below 10° C. Vacuum is applied to remove evolving HCl gas while the mixture was allowed to warm to ~30° C. Diethyl ether is replaced twice as it was evaporated while continuously mixing for two hours. Then the ether is removed by vacuum prior to the next step.

The resulting mixture is added slowly, with mixing, to a stainless steel beaker containing 22.68 g of a 25% solution of sodium methoxide in methanol (0.105 mol) that is chilled in an ice bath. The mixture is stirred for an hour then poured into a stainless steel tray. The solvents are then evaporated and the sample further dried using a vacuum oven. A near terminal branched alcohol sulfate surfactant is obtained.

I.C. Near Terminal Branched Alcohol Ethoxylate 223.7 grams (1.0 mol) of the near terminal alcohol mixture of Example I.A. above plus sufficient catalyst to facilitate the reaction of the alcohol with ethylene oxide within a suitable period of time and in a controllable manner are charged to a 600 mL stainless steel stirred pressure vessel with a cooling coil. A suitable catalyst is 1.1 grams of a solution consisting of 50% potassium hydroxide in water. Other kinds and quantities of catalyst can be used based upon the demands of the process.

The reactor is heated while applying a vacuum for removing materials that can result in side products, such as water, that may be introduced with the catalyst, at a temperature that does not allow the loss of the near terminal alcohol mixture of example I.A., generally between 40° C. and 90° C., but preferably between about 60° C. and about at 80° C., when using a water aspirator as a vacuum source. The removal of water is facilitated by using low speed agitation, generally about 50 rpm, while sparging the mixture with a low level (trickle) stream of inert gas either through a bottom drain valve or through a stainless steel gas dispersion frit or any inert diptube or sintered metal fritted material or by sweeping the area above the mixture with inert gas. Samples can be drawn from the reactor and analyzed for water content using an appropriate analytical method such as Karl-Fischer titration.

After completion of the water removal step, ethylene oxide can be added all at once if the reactor system is properly designed to prevent an uncontrolled rate of reaction. However, the best reaction control is obtained by first heating the reactor under a static vacuum (or optionally with added pressure from an inert gas such as nitrogen) to a temperature that is suitable for the reaction of the alcohol-catalyst mixture with ethylene oxide to occur with minimum side products and color generation, generally between 85° and 150° C., but preferably between about 110° C. and 130° C. Once the reactor has reached the desired temperature, 308 grams (7.0 mol) of ethylene oxide is added at a rate that will be controllable by the cooling system, generally over a period of 30 to 60 minutes. After the addition of ethylene oxide is completed, stirring and heating is continued until the ethylene oxide has been consumed by the reaction. The product can then be degassed and removed from the reaction vessel and stored as is or for long term storage the catalyst is neutralized with one equivalent of a acid selected from citric, HCl or sulfuric acid. The neutralized product can be filtered to remove any solid residue. The surfactant is now ready to use.

II. Cleaning Compositions

Granular Laundry Detergents

Example 1

| Formula | A wt % | B wt % | C wt % | D wt % | E wt % |
|---|---|---|---|---|---|
| Near Terminal Branched Alcohol Sulfate, Sodium Salt, from Example 1 B | 13-25 | 13-25 | 13-25 | 13-25 | 9-25 |
| $C_{12-18}$ Ethoxylate | — | — | 0-3 | — | 0-1 |
| $C_{14-15}$ alkyl ethoxylate (EO = 7) | 0-3 | 0-3 | — | 0-5 | 0-3 |
| Dimethyl hydroxyethyl lauryl ammonium chloride | — | — | 0-2 | 0-2 | 0-2 |
| Sodium tripolyphosphate | 20-40 | — | 18-33 | 12-22 | 0-15 |
| Zeolite | 0-10 | 20-40 | 0-3 | — | — |
| Silicate builder | 0-10 | 0-10 | 0-10 | 0-10 | 0-10 |
| Carbonate | 0-30 | 0-30 | 0-30 | 5-25 | 0-20 |
| Diethylene triamine penta acetate | 0-1 | 0-1 | 0-1 | 0-1 | 0-1 |
| Polyacrylate | 0-3 | 0-3 | 0-3 | 0-3 | 0-3 |
| Carboxy Methyl Cellulose | 0.2-0.8 | 0.2-0.8 | 0.2-0.8 | 0.2-0.8 | 0.2-0.8 |
| Percarbonate | 0-10 | 0-10 | 0-10 | 0-10 | 0-10 |
| Nonanoyloxybenzenesulfonate, sodium salt | — | — | 0-2 | 0-2 | 0-2 |
| Tetraacetylethylenediamine | — | — | 0-0.6 | 0-0.6 | 0-0.6 |
| Zinc Phthalocyanine Tetrasulfonate | — | — | 0-0.005 | 0-0.005 | 0-0.005 |
| Brightener | 0.05-0.2 | 0.05-0.2 | 0.05-0.2 | 0.05-0.2 | 0.05-0.2 |
| $MgSO_4$ | — | — | 0-0.5 | 0-0.5 | 0-0.5 |
| Enzymes | 0-0.5 | 0-0.5 | 0-0.5 | 0-0.5 | 0-0.5 |
| Minors (perfume, dyes, suds stabilizers) | balance | balance | balance | balance | balance |

Example 2

Granular Laundry Detergent

Aqueous Slurry Composition

| Component | % w/w Aqueous slurry |
|---|---|
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulfated or sulphonated variants thereof | 1.23 |
| Ethylenediamine disuccinic acid | 0.35 |
| Brightener | 0.12 |
| Magnesium sulfate | 0.72 |
| Acrylate/maleate copolymer | 6.45 |
| Linear alkyl benzene sulphonate, sodium salt | 11.92 |
| Hydroxyethane di(methylene phosphonic acid) | 0.32 |
| Sodium carbonate | 4.32 |
| Sodium sulfate | 47.49 |
| Soap | 0.78 |
| Water | 24.29 |
| Miscellaneous | 0.42 |
| Total Parts | 100.00 |

Spray-Dried Powder Composition

An aqueous slurry having the composition as described in the "Aqueous Slurry Composition" section (above) is prepared having a moisture content of 25.89 wt %. The aqueous slurry is heated to 72° C. and pumped under high pressure (from $5.5 \times 10^6 \, Nm^{-2}$ to $6.0 \times 10^6 \, Nm^{-2}$), into a counter current spray-drying tower with an air inlet temperature of from 270° C. to 300° C. The aqueous slurry is atomised and the atomised slurry is dried to produce a solid mixture, which is then cooled and sieved to remove oversize material (>1.8 mm) to form a spray-dried powder, which is free-flowing. Fine material (<0.15 mm) is elutriated with the exhaust the exhaust air in the spray-drying tower and collected in a post tower containment system. The spray-dried powder has a moisture content of 1.0 wt %, a bulk density of 427 g/L, and a particle size distribution such that 95.2 wt % of the spray-dried powder has a particle size of from 150 to 710 micrometers. The composition of the spray-dried powder is given below.

| Component | % w/w Spray-dried powder |
|---|---|
| A compound having the following general structure: bis(($C_2H_5O$)($C_2H_4O$)n)($CH_3$)—$N^+$—$C_xH_{2x}$—$N^+$—($CH_3$)- | 1.62 |

| Component | % w/w Spray-dried powder |
|---|---|
| bis(($C_2H_5O$)($C_2H_4O$)n), wherein n = from 20 to 30, and x = from 3 to 8, or sulfated or sulphonated variants thereof | |
| Ethylenediamine disuccinic acid | 0.46 |
| Brightener | 0.16 |
| Magnesium sulfate | 0.95 |
| Acrylate/maleate copolymer | 8.45 |
| C11.8 Linear alkyl benzene sulphonate, sodium salt blended 2:1 with the Near Terminal Branched Alcohol Sulfate sodium salt from Example I.B. | 12.65 |
| Hydroxyethane di(methylene phosphonic acid) | 0.42 |
| Sodium carbonate | 5.65 |
| Sodium sulfate | 61.98 |
| Soap | 1.02 |
| Water | 1.00 |
| Miscellaneous | 0.55 |
| Total Parts | 100.00 |

Preparation of an Anionic Surfactant Particle 1

The anionic detersive surfactant particle 1 is made on a 520 g batch basis using a Tilt-A-Pin then Tilt-A-Plow mixer (both made by Processall). About 108 g sodium sulfate is added to the Tilt-A-Pin mixer along with 244 g sodium carbonate. About 168 g of 70 wt % active $C_{25}E_3S$ paste (sodium ethoxy sulfate based on $C_{12/15}$ alcohol and ethylene oxide) is added to the Tilt-A-Pin mixer. The components are then mixed at 1200 rpm for 10 seconds. The resulting powder is then transferred into a Tilt-A-Plow mixer and mixed at 200 rpm for 2 minutes to form particles. The particles are then dried in a fluid bed dryer at a rate of 2500 L/min at 120° C. until the equilibrium relative humidity of the particles is less than 15 wt %. The dried particles are then sieved and the fraction through 1180 µm and on 250 µm is retained. The composition of the anionic detersive surfactant particle 1 is as follows:

25.0% w/w $C_{25}E_3$ sulfate, sodium salt
18.0% w/w sodium sulfate
57.0% w/w sodium carbonate Preparation of a Cationic Detersive Surfactant Particle 1

The cationic surfactant particle 1 is made on a 14.6 kg batch basis on a Morton FM-50 Loedige mixer. About 4.5 kg of micronised sodium sulfate and 4.5 kg micronised sodium carbonate are premixed in the Morton FM-50 Loedige mixer. About 4.6 kg of 40 wt % active mono-C12-14 alkyl mono-hydroxyethyl di-methyl quaternary ammonium chloride (cationic surfactant) aqueous solution is added to the Morton FM-50 Loedige mixer whilst both the main drive and the chopper are operating. After approximately two minutes of mixing, a 1.0 kg 1:1 weight ratio mix of micronised sodium sulfate and micronised sodium carbonate is added to the mixer. The resulting agglomerate is collected and dried using a fluid bed dryer on a basis of 2500 L/min air at 100-140° C. for 30 minutes. The resulting powder is sieved and the fraction through 1400 µm is collected as the cationic surfactant particle 1. The composition of the cationic surfactant particle 1 is as follows:

15% w/w mono-C12-14 alkyl mono-hydroxyethyl di-methyl quaternary ammonium chloride
40.76% w/w sodium carbonate
40.76% w/w sodium sulfate
3.48% w/w moisture and miscellaneous Preparation of a Granular Laundry Detergent Composition About 10.84 kg of the spray-dried powder from the "Spray-Dried Powder" section (above), 4.76 kg of the anionic detersive surfactant particle 1, 1.57 kg of the cationic detersive surfactant particle 1 and 7.83 kg (total amount) of other individually dosed dry-added material are dosed into a 1 m diameter concrete batch mixer operating at 24 rpm. After all of the materials are dosed into the mixer, the mixture is mixed for 5 minutes to form a granular laundry detergent composition. The formulation of the granular laundry detergent composition is described below:

| Component | A. % w/w granular laundry detergent composition | B. % w/w granular laundry detergent composition |
|---|---|---|
| Spray-dried powder from the "Spray-Dried Powder" section (above) | 43.34 | 15 |
| 91.6 wt % active linear alkyl benzene sulphonate, sodium salt flake supplied by Stepan under the tradename NACCONOL 90G ® | 0.22 | 2 |
| Citric acid | 5.00 | 0 |
| Sodium percarbonate (having from 12% to 15% washing active oxygen (active AvOx)) | 14.70 | 0 |
| Photobleach particle | 0.01 | 0 |
| Lipase (11.00 mg active/g) | 0.70 | 0.90 |
| Amylase (21.55 mg active/g) | 0.33 | 0.50 |
| Protease (56.00 mg active/g) | 0.43 | 0.60 |
| Tetraacetyl ethylene diamine agglomerate (92 wt % active) | 4.35 | 4.0 |
| Suds suppressor agglomerate (11.5 wt % active) | 0.87 | 1.0 |
| Acrylate/maleate copolymer particle (95.7 wt % active) | 0.29 | 0 |
| Green/Blue carbonate speckle | 0.50 | 0 |
| Anionic detersive surfactant particle 1 | 19.04 | 10 |
| Cationic detersive surfactant particle 1 | 6.27 | 3 |
| Sodium sulfate | balance | balance |
| Solid perfume particle | 0.63 | 0.7 |
| Total Parts | 100.00 | 100.00 |

Example 3

Liquid Laundry Detergents

| | Ingredient | | | | |
|---|---|---|---|---|---|
| | A wt % | B wt % | C wt % | D wt % | E wt % |
| C12-15 $EO_{1.8}$ sulfate sodium salt | 14.4 | 0 | 9.2 | 5.4 | 0 |
| Near Terminal Branched Alcohol Sulfate, sodium salt from Example I.B. | 4.4 | 12.2 | 5.7 | 1.3 | 20 |
| Alkyl ethoxylate | 2.2 | 8.8 | 8.1 | 3.4 | 0 |

-continued

| Ingredient | | | | | |
|---|---|---|---|---|---|
| Amine oxide | 0.7 | 1.5 | 0 | 0 | 0 |
| Citric acid | 2.0 | 3.4 | 1.9 | 1.0 | 1.6 |
| HLAS (linear alkylbenzene sulfonate, acid form) | 3.0 | 0 | 0 | 0 | 5.0 |
| Protease | 1.0 | 0.7 | 1.0 | 0 | 2.5 |
| Amylase | 0.2 | 0.2 | 0 | 0 | 0.3 |
| Lipase | 0 | 0 | 0.2 | 0 | 0 |
| Borax | 1.5 | 2.4 | 2.9 | 0 | 0 |
| Calcium and sodium formate | 0.2 | 0 | 0 | 0 | 0 |
| Formic acid | 0 | 0 | 0 | 0 | 1.1 |
| Ethoxylated polyamine polymer or polymers | 1.7 | 2.0 | 0 | 0.8 | 0 |
| Sodium polyacrylate copolymer | 0 | 0 | 0.6 | 0 | 0 |
| DTPA[1] | 0.1 | 0 | 0 | 0 | 0.9 |
| DTPMP[2] | 0 | 0.3 | 0 | 0 | 0 |
| EDTA[3] | 0 | 0 | 0 | 0.1 | 0 |
| Fluorescent whitening agent | 0.15 | 0.2 | 0.12 | 0.12 | 0.2 |
| Ethanol | 2.5 | 1.4 | 1.5 | 0 | 0 |
| Propanediol | 6.6 | 4.9 | 4.0 | 0 | 15.7 |
| Sorbitol | 0 | 0 | 4.0 | 0 | 0 |
| Ethanolamine | 1.5 | 0.8 | 0.1 | 0 | 11.0 |
| Sodium hydroxide | 3.0 | 4.9 | 1.9 | 1.0 | 0 |
| Sodium cumene sulfonate | 0 | 2.0 | 0 | 0 | 0 |
| Silicone suds suppressor | 0 | 0.01 | 0 | 0 | 0 |
| Perfume | 0.3 | 0.7 | 0.3 | 0.4 | 0.6 |
| Opacifier[4] | 0 | 0.30 | 0.20 | 0 | 0.50 |
| Water | balance | balance | balance | balance | balance |
| | 100.0% | 100.0% | 100.0% | 100.0% | 100.0% |

[1] diethylenetriaminepentaacetic acid, sodium salt
[2] diethylenetriaminepentakismethylenephosphonic acid, sodium salt
[3] ethylenediaminetetraacetic acid, sodium salt
[4] Acusol OP 301

| Ingredient | F wt % | G wt % | H wt % | I wt % | J wt % | K wt % |
|---|---|---|---|---|---|---|
| Alkylbenzene sulfonic acid | 7 | 7 | 4.5 | 1.2 | 1.5 | 12.5 |
| C12-14 EO$_3$ sulfate, sodium salt | 2.3 | 2.3 | 4.5 | 4.5 | 7 | 18 |
| Near Terminal Branched Alcohol Ethoxylate from Example I.C. | 5 | 5 | 2.5 | 2.6 | 4.5 | 4 |
| C12 alkyl dimethyl amine oxide | — | 2 | — | — | — | — |
| C12-14 alkyl hydroxyethyl dimethyl ammonium chloride | — | — | — | 0.5 | — | — |
| C12-18 Detergent acid | 2.6 | 3 | 4 | 2.6 | 2.8 | 11 |
| Citric acid | 2.6 | 2 | 1.5 | 2 | 2.5 | 3.5 |
| Protease enzyme | 0.5 | 0.5 | 0.6 | 0.3 | 0.5 | 2 |
| Amylase enzyme | 0.1 | 0.1 | 0.15 | — | 0.05 | 0.5 |
| Mannanase enzyme | 0.05 | — | 0.05 | — | — | 0.1 |
| Diethylenetriaminepenta(methylenephosphonic) acid | 0.2 | 0.3 | — | — | 0.2 | — |
| Hydroxyethane diphosphonic acid | — | — | 0.45 | — | — | 1.5 |
| FWA | 0.1 | 0.1 | 0.1 | — | — | 0.2 |
| Solvents (1,2 propanediol, ethanol), stabilizers | 3 | 4 | 1.5 | 1.5 | 2 | 4.3 |
| Hydrogenated castor oil derivative structurant | 0.4 | 0.3 | 0.3 | 0.1 | 0.3 | — |
| Boric acid | 1.5 | 2 | 2 | 1.5 | 1.5 | 0.5 |
| Na formate | — | — | — | 1 | — | — |
| Reversible protease inhibitor | — | — | 0.002 | — | — | — |
| Perfume | 0.5 | 0.7 | 0.5 | 0.5 | 0.8 | 1.5 |
| Buffers (sodium hydroxide, Monoethanolamine) | To pH 8.2 | | | | | |
| Water and minors (antifoam, aesthetics, . . . ) | To 100 | | | | | |

| Ingredient | L wt % | M wt % | N wt % | O wt % | P wt % | Q wt % |
|---|---|---|---|---|---|---|
| C11.6 Linear Alkylbenzene Sulfonic Acid, sodium salt | 5.5 | 2.7 | 2.2 | 12.2 | 5.2 | 5.2 |
| C12-14 EO$_3$ sulfate, sodium salt | 16.5 | 20 | 9.5 | 7.7 | 1.8 | 1.8 |

-continued

| | | | | | | |
|---|---|---|---|---|---|---|
| Sodium C12-14 alkyl sulfate, sodium salt | 8.9 | 6.5 | 2.9 | — | | |
| C12-14 alkyl 7-ethoxylate | | | | | 0.15 | 0.15 |
| C14-15 alkyl 8-ethoxylate | | | | | 3.5 | 3.5 |
| C12-15 alkyl 9-ethoxylate | 1.7 | 0.8 | 0.3 | 18.1 | — | — |
| C12-18 Detergent acid | 2.2 | 2.0 | — | 1.3 | 2.6 | 2.6 |
| Citric acid | 3.5 | 3.8 | 2.2 | 2.4 | 2.5 | 2.5 |
| Protease enzyme | 1.7 | 1.4 | 0.4 | — | 0.5 | 0.5 |
| Amylase enzyme | 0.4 | 0.3 | — | — | 0.1 | 0.1 |
| Mannanase enzyme | | | | | 0.04 | 0.04 |
| PEG-PVAc Polymer[1] | — | — | — | — | — | 0.3 |
| Ethoxyed Hexamethylene Diamine Dimethyl Quat Disulfate | — | — | — | — | — | 0.7 |
| Diethylenetriaminepenta(methylene-phosphonic) acid | | | | | 0.2 | 0.2 |
| Solvents (1,2 propanediol, ethanol, stabilizers | 7 | 7.2 | 3.6 | 3.7 | 1.9 | 1.9 |
| Hydrogenated castor oil derivative structurant | 0.3 | 0.2 | 0.2 | 0.2 | 0.35 | 0.35 |
| Polyacrylate | — | — | — | 0.1 | — | — |
| Polyacrylate copolymer[2] | — | — | — | 0.5 | — | — |
| Sodium carbonate | — | — | — | 0.3 | — | — |
| Sodium silicate | — | — | — | — | — | — |
| Borax | 3 | 3 | 2 | 1.3 | — | — |
| Boric acid | 1.5 | 2 | 2 | 1.5 | 1.5 | 1.5 |
| Perfume | 0.5 | 0.5 | 0.5 | 0.8 | 0.5 | 0.5 |
| Buffers (sodium hydroxide, monoethanolamine) | | | | | 3.3 | 3.3 |
| Water, dyes and miscellaneous | | | Balance | | | |

[1]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2]Alco 725 (styrene/acrylate)

Example 4

Liquid Laundry Detergent

| Ingredient | Wt % |
|---|---|
| Propylene glycol | 4.75 |
| Sodium citrate | 2.8 |
| NaOH (50%) | 0.43 |
| Monoethanolamine | 0.23 |
| LAS, acid form | 6.0 |
| Coconut fatty acid | 0.77 |
| Near-terminal branched alcohol EO2 sulfate | 10.5 |
| Nonionic surfactant | 6.6 |
| 1-decanol | 6.0 |
| protease | 0.45 |
| Lipase | 0.25 |
| perfume | 0.2 |
| Water | Balance to 100 |

Example 5

Liquid Dish Handwashing Detergents

| Composition | A wt % | B wt % |
|---|---|---|
| $C_{12-13}$ Natural AE0.6S (S is sulfate, sodium salt) blended 50:50 by weight with Near Terminal Branched Alcohol Sulfate, sodium salt from Example I.B. | 27.0 | 24.0 |
| $C_{10-14}$ mid-branched Amine Oxide | — | 6.0 |
| Near Terminal Branched Alcohol Ethoxylate from Example I.C. | 2.0 | 5.0 |
| $C_{12-14}$ Linear Amine Oxide | 6.0 | — |

-continued

| Composition | A wt % | B wt % |
|---|---|---|
| SAFOL ® 23 Amine Oxide | 1.0 | 1.0 |
| $C_{11}E_9$ Nonionic[1] | 2.0 | 2.0 |
| Ethanol | 4.5 | 4.5 |
| Sodium cumene sulfonate | 1.6 | 1.6 |
| Polypropylene glycol 2000 | 0.8 | 0.8 |
| NaCl | 0.8 | 0.8 |
| 1,3 BAC Diamine[2] | 0.5 | 0.5 |
| Suds boosting polymer[3] | 0.2 | 0.2 |
| Water | Balance | Balance |

[1]Nonionic may be $C_{11}$ Alkyl ethoxylated surfactant containing 9 ethoxy groups.
[2]1,3 BAC is 1,3 bis(methylamine)-cyclohexane.
[3](N,N-dimethylamino)ethyl methacrylate homopolymer

Example 6

Automatic Dishwasher Detergent

| | A wt % | B wt % | C wt % | D wt % | E wt % |
|---|---|---|---|---|---|
| Polymer dispersant[2] | 0.5 | 5 | 6 | 5 | 5 |
| Carbonate | 35 | 40 | 40 | 35-40 | 35-40 |
| Sodium tripolyphosphate | 0 | 6 | 10 | 0-10 | 0-10 |
| Silicate solids | 6 | 6 | 6 | 6 | 6 |
| Bleach and bleach activators | 4 | 4 | 4 | 4 | 4 |
| Polymer[1] | 0.05-10 | 1 | 2.5 | 5 | 10 |
| Enzymes | 0.3-0.6 | 0.3-0.6 | 0.3-0.6 | 0.3-0.6 | 0.3-0.6 |
| Disodium citrate dihydrate | 0 | 0 | 0 | 2-20 | 0 |
| Near Terminal Branched Alcohol | 0.8-5 | 0.8-5 | 0.8-5 | 0.8-5 | 0.8-5 |

-continued

| | A wt % | B wt % | C wt % | D wt % | E wt % |
|---|---|---|---|---|---|
| Ethoxylate from Example I.C. | | | | | |
| Water, e, perfume, dyes and other adjuncts | Balance to 100% | Balance to 100% | Balance to 100% | Balance to 100% | Balance to 100% |

[1] An amphiphilic alkoxylated polyalkylenimine polymer.
[2] Such as ACUSOL ® 445N available from Rohm & Haas or ALCOSPERSE ® from Alco.

Example 7

Hard Surface Cleaner

A hard surface cleaner comprises 5% total nonionic surfactant (near-terminal branched alcohol ethoylated with 8 moles of ethylene oxide), 0.2% citric acid, perfume 0.3%, and water to 100%.

Example 8

Comparison of the Interfacial Surface Tension of Anteiso/Iso-Sulfate Mixtures vs. Current Surfactants

| Sample | Minimum Interfacial Tension (IFT), mN/m at 6 gpg* |
|---|---|
| High solubility alkyl sulfate surfactant (HSAS) | 0.42 |
| Linear alcohol ethoxylated sulfate (AE1.8S) | 2.81 |
| C11.8 Linear alkyl benzene sulfonate, sodium salt (LAS) | 1.14 |
| 12-Methyltetradecylsulfate | 0.69 (precipitate near end) |
| 13-Methyltetradecylsulfate | NM (precipitated) |
| 12-Methyltetradecylsulfate/13-methyltetradecylsulfate (60:40) | 0.22 |

15° C., 1 μM/min flow rate;
S = sodium salt of the sulfated alcohol or ethoxylated alcohol.
*Unit of water hardness, One "gpg" is 1 grain (64.8 milligrams) of calcium carbonate dissolved in 1 US gallon of water, equivalent to 14.3 parts per million (PPM).

The Dynamic Interfacial Tension analysis was performed on a Kruss® DVT30 Drop Volume Tensiometer. The instrument is configured to measure the interfacial tension of an ascending oil drop in aqueous detergent (surfactant) phase. The oil was canola oil. The aqueous detergent and oil phases are temperature controlled via a Polyscience® circulating water temperature controller attached to tensiometer. A dynamic interfacial tension curve is generated by dispensing the oil drops into the aqueous detergent phase from an ascending capillary with diameter of 0.2540 mm over a range of flow rates and measuring the interfacial tension at each flow rate. Data is generated at oil dispensing flow rates of 500 uL/min-1 uL/min with 2 flow rates per decade on a logarithmic scale (7 flow rates measured). Interfacial tension is measured on three oil drops per flow rate, then averaged. Interfacial tension is reported in units of mN/m. Surface age of the oil drops at each flow rate is also recorded and plots can be generated either of interfacial tension (y-axis) versus oil flow rate (x-axis) or interfacial tension (y-axis) versus oil drop surface age (x-axis).

III. Personal Care Compositions

Example 9

Conditioning Compositions

| | | Control (%) | A (%) | B (%) | C (%) |
|---|---|---|---|---|---|
| Stage A | Water | To 100% | To 100% | To 100% | To 100% |
| | Behentrimonium Methosulfate/IPA | 2.2 | 2.2 | 2.2 | 2.2 |
| | Ethylenediamine-tetraacetic acid (EDTA) | 0.12 | 0.12 | 0.12 | 0.12 |
| | 14-Methylhexadecanol | — | 0.75 | — | 0.75 |
| | 15-Methylhexadecanol | — | 0.75 | 0.75 | — |
| | 15-Methylheptadecanol* | — | — | 0.75 | 0.75 |
| | Cetyl Alcohol | 1.5 | — | — | — |
| | Stearyl Alcohol | 3.7 | 3.7 | 3.7 | 3.7 |
| | Benzyl Alcohol | 0.4 | 0.4 | 0.4 | 0.4 |
| | Preservative (e.g., KATHON ™ CG) | 0.03 | 0.03 | 0.03 | 0.03 |
| Stage B | Amodimethicone | 0.5 | 0.5 | 0.5 | 0.5 |
| | Pathenol | 0.1 | 0.1 | 0.1 | 0.1 |
| | Perfume | 0.4 | 0.4 | 0.4 | 0.4 |
| | TOTAL | 100.0 | 100.0 | 100.0 | 100.0 |

*Derivable from methesis of erucic acid-based triglyceride and 3-methyl-1-pentene.

The mixtures of near terminal-branched alcohols (15-methylhexadecanol, 14-methylhexadecanol, and 15-methylheptadecanol) can be substituted with any mixture of near terminal-branched alcohols with 17 to 21 carbon atoms, as described herein.

Other mixtures of near-terminal branched alcohols can be substituted for 15-methylhexadecanol, 14-methylhexadecanol, and 15-methylheptadecanol in the above conditioning compositions. For example, the mixture in the above conditioning composition can include at two iso alcohols, two anteiso alcohols, or one iso alcohol and one anteiso alcohol. Nonlimiting examples of near terminal-branched alcohols that can be substituted for 15-methylhexadecanol, 14-methylhexadecanol, and 15-methylheptadecanol in the above conditioning compositions are Compounds 32-62 in Table A, Compounds 1-22 in Table B, and Compounds 1-34 in Table C, where Z is OH.

The cationic compounds in the above table can be substituted with any appropriate cationic compound such as, for example, cetyltrimonium chloride (CTAC), stearyltrimonium chloride (STAC), stearoylamidopropyldimethyl amine (SAPDMA), and distearyldimethylammonium chloride.

Example 10

Conditioning Compositions

| | | Control (%) | A (%) | B (%) | C (%) |
|---|---|---|---|---|---|
| Stage A | Water | To 100% | To 100% | To 100% | To 100% |
| | EDTA | 0.13 | 0.13 | 0.13 | 0.13 |
| | Stearyl Alcohol | 2.3 | 2.3 | 2.3 | 2.3 |
| | 14-Methylhexadecanol | — | 0.45 | — | 0.45 |

-continued

|  | | Control (%) | A (%) | B (%) | C (%) |
|---|---|---|---|---|---|
| | 15-Methylhexadecanol* | — | 0.45 | 0.45 | — |
| | 16-Methyloctadecanol | — | — | 0.45 | 0.45 |
| | Cetyl Alcohol | 0.9 | — | — | — |
| | VARISOFT ® 432PPG, quaternary ammonium di-alkyl solution | 0.5 | 0.5 | 0.5 | 0.5 |
| | Behentrimonium Methosulfate/IPA | 1.4 | 1.4 | 1.4 | 1.4 |
| | Benzyl Alcohol | 0.4 | 0.4 | 0.4 | 0.4 |
| | Preservative (e.g., KATHON ™ CG) | 0.03 | 0.03 | 0.03 | 0.03 |
| Stage B | Amodimethicone | 0.8 | 0.8 | 0.8 | 0.8 |
| | Pathenol | 0.1 | 0.1 | 0.1 | 0.1 |
| | Perfume | 0.3 | 0.3 | 0.3 | 0.3 |
| | TOTAL | 100.0 | 100.0 | 100.0 | 100.0 |

*Derivable from metathesis of erucic acid-based triglyceride and 3-methyl-1-butene.

The mixtures of near terminal-branched alcohols (15-methylhexadecanol, 14-methylhexadecanol, and 16-methyloctadecanol) can be substituted with any mixture of near terminal-branched alcohols with 17 to 21 carbon atoms, as described herein. For example, the mixture in the above conditioning compositions can include at two iso alcohols, two anteiso alcohols, or one iso alcohol and one anteiso alcohol. Nonlimiting examples of near terminal-branched alcohols that can be substituted for 15-methylhexadecanol, 14-methylhexadecanol, and 15-methyloctadecanol in the above conditioning compositions are Compounds 32-62 in Table A, Compounds 1-22 in Table B, and Compounds 1-34 in Table C, where Z is OH.

In the conditioning examples the other cationics often used are cetyltrimonium chloride (CTAC), stearyltrimonium chloride (STAC), stearoylamidopropyldimethyl amine (SAPDMA), distearyldimethylammonium chloride.

The cationic compounds in the above table can be substituted with any appropriate cationic compound such as, for example, cetyltrimonium chloride (CTAC), stearyltrimonium chloride (STAC), stearoylamidopropyldimethyl amine (SAPDMA), and distearyldimethylammonium chloride.

Example 11

Shampoo Compositions

| | Formulation | | | |
|---|---|---|---|---|
| Component | A (%) | B (%) | C (%) | D (%) |
| 10-Methyldodecylsulfate, sodium or ammonium salt | 12 | 6 | — | — |
| 11-Methyldodecylsulfate, sodium or ammonium salt* | — | 6 | — | — |
| 10-Methyldodecylsulfate-ethoxylated, sodium or ammonium salt | — | — | 12 | 6 |
| 11-Methyldodecylsulfate-1-ethoxylated, sodium or ammonium salt | — | — | — | 6 |
| Cocobetaine (CocoB) | 1-1.5 | 1-1.5 | 1-1.5 | 1-1.5 |
| Cationic polymer (e.g., AM:TRI, cationic guar gum) | 0.25 | 0.25 | 0.25 | 0.25 |
| Silicone | 1.0 | 1.0 | 1.0 | 1.0 |
| Ethylene glycol distearate (EGDS) | 1.25 | 1.25 | 1.25 | 1.25 |
| Sodium Lauryl Sulfate (SLS) | 1.5 | 1.5 | 1.5 | 1.5 |
| Finishing Agents (e.g., perfume, pH adjusters, water) | To 100 | To 100 | To 100 | To 100 |

*Derivable via methathesis of oleyl-based oil and 3-methyl-1-butene.

Example 12

The following compositions are useful for clarifying shampoos.

| | Formulation | | | |
|---|---|---|---|---|
| Component | A (%) | B (%) | C (%) | D (%) |
| 10-Methyldodecylsulfate, sodium or ammonium salt | 12 | 6 | — | — |
| 11-Methyldodecylsulfate, sodium or ammonium salt* | — | 6 | — | — |
| 10-Methyldodecylsulfate-ethoxylated, sodium or ammonium salt | — | — | 12 | 6 |
| 11-Methyldodecylsulfate-1-ethoxylated, sodium or ammonium salt | — | — | — | 6 |
| Cocobetaine (CocoB) | 1-1.5 | 1-1.5 | 1-1.5 | 1-1.5 |
| Cationic polymer (e.g., AM:TRI, cationic guar gum) | 0.25 | 0.25 | 0.25 | 0.25 |
| Finishing Agents (e.g., perfume, pH adjusters, water) | To 100 | To 100 | To 100 | To 100 |

The mixtures of near terminal-branched sulfates (the sodium or ammonium salts of 10-methyldodecylsulfate, 11-methyldodecylsulfate, 10-methyldodecylsulfate-1-ethoxylated, and 11-methyldodecylsulfate-1-ethoxylated) can be substituted with any mixture of near terminal-branched anionic surfactants with 13 to 18 carbon atoms, as described herein. For example, the mixture in the above shampoo compositions can include at two iso sulfates, two anteiso sulfates, or one iso sulfate and one anteiso sulfate.

Nonlimiting examples of near terminal-branched anionic surfactants that can be substituted for the sodium or ammonium salts of 10-methyldodecylsulfate, 11-methyldodecylsulfate, 10-methyldodecylsulfate-1-ethoxylated, and 11-methyldodecylsulfate-1-ethoxylated in the above conditioning compositions are Compounds 11-42 in Table A, Compounds 1-16 in Table B, and Compounds 1-19 in Table C, where Z is carboxylate, sulfate, disulfate, sulfonate, disulfonate, glycerol ester sulfonate, a phosphate ester, glycerol sulfonate, polygluconate, a polyphosphate ester, phosphonate, sulfosuccinate, sulfosuccaminate, taurinate, sarcosinate, glycinate, isethionate, monoalkanolamide sulfate, diglycolamide sulfate, a glycerol ester sulfate, a glycerol ether sulfate, a polyglycerol ether sulfate, ammonioalkanesulfonate, alken-2-ylsuccinate, and a sulfonated fatty acid. In one embodiment herein, the foregoing selections for Z do not include carboxylate.

Zinc pyridinethione (ZPT) can be added to any of compositions A-D in Example 3 to result in an anti-dandruff shampoo.

One or more additional co-surfactants can be added to any of the above shampoo compositions such as, for example, CAPB (cocoamidopropyl betaine), Cocobetaine (CocoB), sodium lauroylamphoacetate (NaLAA), laurylhydroxysultaine (LHS), and cocomonoethanol amide (CMEA).

Example 13

Compact Shampoo Compositions

| Component | A (%) | B (%) | C (%) | D (%) | E (%) | F (%) |
|---|---|---|---|---|---|---|
| 10-Methyldodecylsulfate, sodium or ammonium salt | 6 | 3 | — | — | — | — |
| 11-Methyldodecylsulfate, sodium or ammonium salt | — | 3 | 6 | — | — | — |
| 10-Methyldodecylsulfate-1-ethoxylated, sodium or ammonium salt | — | — | — | 20 | 10 | — |
| 11-Methyldodecylsulfate-1-ethoxylated, sodium or ammonium salt | — | — | — | — | 10 | 20 |
| Sodium Lauryl Sulfate (SLS) | 1.5 | 1.5 | 1.5 | 1.5 | 1.5 | 1.5 |
| Sodium Laureth Sulfate, 1-ethoxylated (SLE(1)S) | 16 | 16 | 16 | 0 | 0 | 0 |
| Cocobetaine (CocoB) | 1.9 | 1.9 | 1.9 | 1.9 | 1.9 | 1.9 |
| Cationic polymer (e.g., AM:TRI, cationic guar gum) | 0.1 | 0.1 | 0.1 | 0.1 | 0.1 | 0.1 |
| LP-Silicone | 2.5 | 2.5 | 2.5 | 2.5 | 2.5 | 2.5 |
| Perfume | 1.5 | 1.5 | 1.5 | 1.5 | 1.5 | 1.5 |
| Ethylene glycol distearate (EGDS) | 1.25 | 1.25 | 1.25 | 1.25 | 1.25 | 1.25 |
| Finishing Agents | To 100 | To 100 | To 100 | To 100 | To 100 | To 100 |

The mixtures of near terminal-branched sulfates (the sodium or ammonium salts of 10-methyldodecylsulfate, 11-methyldodecylsulfate, 10-methyldodecylsulfate-1-ethoxylated, and 11-methyldodecylsulfate-1-ethoxylated) can be substituted with any mixture of near terminal-branched anionic surfactants with 13 to 18 carbon atoms, as described herein. For example, the mixture in the above compact shampoo compositions can include at two iso sulfates, two anteiso sulfates, or one iso sulfate and one anteiso sulfate.

Nonlimiting examples of near terminal-branched anionic surfactants that can be substituted for the sodium or ammonium salts of 10-methyldodecylsulfate, 11-methyldodecylsulfate, 10-methyldodecylsulfate-1-ethoxylated, and 11-methyldodecylsulfate-1-ethoxylated in the above conditioning compositions are Compounds 11-42 in Table A, Compounds 1-16 in Table B, and Compounds 1-19 in Table C, where Z is carboxylate, sulfate, disulfate, sulfonate, disulfonate, glycerol ester sulfonate, a phosphate ester, glycerol sulfonate, polygluconate, a polyphosphate ester, phosphonate, sulfosuccinate, sulfosuccaminate, taurinate, sarcosinate, glycinate, isethionate, monoalkanolamide sulfate, diglycolamide sulfate, a glycerol ester sulfate, a glycerol ether sulfate, a polyglycerol ether sulfate, ammonioalkanesulfonate, alken-2-yl-succinate, and a sulfonated fatty acid. In one embodiment herein, the foregoing selections for Z do not include carboxylate.

Zinc pyridinethione (ZPT) can be added to any of compositions A-F in Example 4 to result in an anti-dandruff shampoo. Silicone, SLS, and EGDS are removed from any of compositions A-F in Example 4 to result in a clarifying shampoo.

One or more additional co-surfactants can be added to any of the above shampoo compositions such as, for example, CAPB (cocoamidopropyl betaine), Cocobetaine (CocoB), sodium lauroylamphoacetate (NaLAA), laurylhydroxysultaine (LHS), and cocomonoethanol amide (CMEA).

Example 14

Silicone Free Conditioning Compositions

| Component | A (%) | B (%) | C (%) |
|---|---|---|---|
| Water | To 100 | To 100 | To 100 |
| 14-Methylhexadecylpalmitate* | 0.5-3 | — | 0.25-1.5 |
| Wax ester* | — | 0.5-3 | 0.25-1.5 |
| Catonic Guar[1] | 0.25 | 0.25 | 0.25 |
| Sodium Laureth Sulfate[2] | 8.5 | 8.5 | 8.5 |
| Sodium Lauryl Sulfate[3] | 6.5 | 6.5 | 6.5 |
| CMEA[4] | 0.8 | 0.8 | 0.8 |
| Cocoamidopropyl Betaine[5] | 2.0 | 2.0 | 2.0 |
| Fragrance | 0.70 | 0.70 | 0.70 |
| Preservatives, pH, viscosity adjustment | Up to 3% | Up to 3% | Up to 3% |

[1]Jaguar Excel, from Rhodia
[2]Sodium Laureth Sulfate, from P&G
[3]Sodium Lauryl Sulfate, from P&G
[4]Ninol Comf, from Stepan
[5]Amphosol HCA-B, from Stepan
*The wax ester can include compounds of the invention having a methyl branch on the fatty acid portion of the wax ester, on the fatty alcohol portion of the wax ester, or compounds having a methyl branch on both hydrophobic carbon chains of the wax ester.

The mixtures of near terminal-branched wax esters can include any near terminal-branched wax ester with with 13 to 18 carbon atoms in the fatty acid portion and 14 to 18 carbon atoms in the ester portion. For example, the wax ester can include 13-methylhexadecylpalmitate, 15-methylhexadecylstearate, and 16-methylhexadecylstearate. Wax esters can be prepared by transesterification or via reaction of the fatty acid chloride component with the fatty alcohol or in accordance with other methods also well known in the art. They can also be prepared by metathesis of an existing unsaturated wax ester resulting in a near terminal branched unsaturated wax ester of the invention. Hydrogenation by conventional means will yield a near terminal branched saturated wax ester of the invention.

The cationic compound in the above table can be substituted with any appropriate cationic compound such as, for example, cetyltrimonium chloride (CTAC), stearyltrimonium chloride (STAC), stearoylamidopropyldimethyl amine (SAPDMA), and distearyldimethylammonium chloride.

The composition in Example 5 can be used in conditioning shampoos, conditioners, and compact shampoos.

Wax Ester Emulsion Preparation

Wax ester emulsions can be prepared by typical emulsion preparation procedures and typically have a 1 micron emulsion droplet size. On the small scale for laboratory samples a solid sample is weighed into Flack Tek Speedmixer cup at a level to represent 50% of the final mixture. NEODOL® 1-5 is added at a level to represent 5% of the final mixture. This combination is heated until the wax ester material has liquefied. The mixture is allowed to mix for 0.5 min on the speedmixer at 2000 rpm. Ammonium lauryl sulfate solution (28% active) is added at a level to represent about 10% of the final preparation any additional water required is added at this point, and the mixture re-heated to insure the wax ester material is again liquefied. The preparation in then mixed on the speed mixer for 5 minutes at 3450 rpm. The particle size of the resulting emulsion is checked by simple light microscopy to insure it is in the right domain, e.g. about 1 micron.

On a larger scale the ammonium lauryl sulfate can be added to the de-ionized water amount required and the mixture heated to about 80 C. The wax ester material is combined with the NEODOL® 1-5 and the mixture heated until liquefied. This mixture is added in a controlled manor to aqueous ammonium lauryl sulfate solution with high speed mixing, e.g. a Divtech Eurostar with Turbine. The particle size is verified by light microscopy.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising at least about 50 wt % of a mixture of at least two compounds selected from the group consisting of:

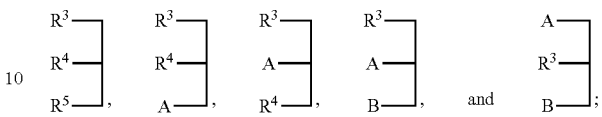

wherein A and B are each independently OH or O(C=O)R$^7$;

R$^1$ is hydrogen, methyl, or ethyl;

R$^2$ is $(C_1\text{-}C_n)$alkyl or $(C_1\text{-}C_n)$alkenyl having 0, 1, 2, or 3 $(C_1\text{-}C_3)$alkyl branches, wherein when R$^1$ is H, R$^2$ has 1, 2, or 3 $(C_1\text{-}C_3)$alkyl branches, and when R$^1$ is methyl or ethyl, R$^2$ has 0, 1, or 2 $(C_1\text{-}C_3)$alkyl branches, and wherein branching occurs on carbon atoms that are within 40% of the nonfunctionalized terminus of the longest carbon chain;

R$^3$, R$^4$, and R$^5$ are each independently

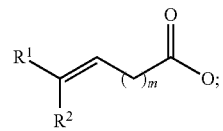

R$^7$ is $(C_1\text{-}C_{26})$alkyl; and, m is 5-37 and n is 1-33, wherein m+n is 6-38; and, wherein the composition contains less than about 2 wt % of secondary hydroxy compounds.

2. The composition of claim 1, herein m is 7-27 and n is 1-23, wherein m+n is 8-28.

3. The composition of claim 2, wherein the mixture is present in an amount of at least about 75 wt %, based on the total weight of the composition.

4. The composition of claim 2, wherein R$^1$ is hydrogen, methyl, or ethyl, and R$^2$ is $(C_1\text{-}C_5)$alkyl or $(C_1\text{-}C_5)$alkenyl with 1, 2, or 3 methyl and/or ethyl branches.

5. The composition of claim 2, wherein the omega-1 branched compounds are present in an amount of about 1 wt % to about 40 wt %, based on the total weight of near terminal-branched compounds.

6. The composition of claim 2, wherein the composition is free of secondary hydroxy compounds.

7. The composition of claim 2, further comprising a linear fatty acid, a linear fatty alcohol, a mid-chain branched fatty acid, a mid-chain branched fatty alcohol, or mixtures thereof in an amount of less than about 50 wt %, based on the total weight of the composition.

8. The composition of claim 7, wherein the linear fatty acid, the linear fatty alcohol, the mid-chain branched fatty acid, the mid-chain branched fatty alcohol, and mixtures thereof in an amount of less than about 10 wt %, based on the total weight of the composition.

9. The composition of claim 1, wherein the moiety
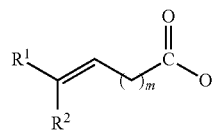
is fully or partially hydrogenated.
* * * * *